US006579869B1

(12) United States Patent
Robin et al.

(10) Patent No.: US 6,579,869 B1
(45) Date of Patent: Jun. 17, 2003

(54) CEPHALOTAXANES: THEIR METHOD OF PREPARATION AND THEIR USE IN TREATMENT OF CANCERS, LEUKEMIAS, PARASITES, INCLUDING THOSE RESISTANT TO USUAL CHEMOTHERAPEUTIC AGENTS, AND AS REVERSAL AGENTS

(75) Inventors: Jean-Pierre Robin, Trange (FR); Robert Dhal, Pruille le Chetif (FR); Freddy Drouye, Le Genest (FR); Jean-Pierre Marie, Sevres (FR); Nina Radosevic, Trange (FR); Julie Robin, Rouillon (FR); Karine Souchaud, Joue-les-Tours (FR); Patricia Bataille, Le Mans (FR)

(73) Assignee: Oncopharm Corporation, Houston, TX (US)

( * ) Notice: Subject to any disclaimer, the term of this patent is extended or adjusted under 35 U.S.C. 154(b) by 0 days.

(21) Appl. No.: 09/710,870

(22) Filed: Nov. 14, 2000

Related U.S. Application Data

(63) Continuation of application No. PCT/IB00/01593, filed on Oct. 17, 2000.

(51) Int. Cl.$^7$ .......................... A61K 31/55; A61P 35/02; C07D 223/14

(52) U.S. Cl. ................... 514/214.01; 540/543; 540/581

(58) Field of Search ................................ 540/543, 581; 514/214.01

(56) References Cited

FOREIGN PATENT DOCUMENTS

WO    WO 99/48894 A1    9/1999

OTHER PUBLICATIONS

Kano et al Blood 97(7) (2001) 1999–2007.*
O'Brien et al Blook 93(12) (1999) 4149–4153.*
Takano et al Bioorg. Med. Chem. Lett. 6(14) (1996) 1689–1690.*
Witte et al Invest. New Drugs 17(2) (1999) 173–177 (Medline abstract only).*
CAPLUS printout for Cheng et al., Stereospecific Synthesis of Deoxyharringtonine and Homoharringtonine, Yaoxue Xuebao, vol. 19, No. 3, pp. 178–183, 1984.*
He et al., Stability–Indicating LC Assay of and Impurity Identification in Homoharringtonine Samples, Journal of Pharmaceutical and Biomedical Analysis, vol. 22, No. 3, pp. 541–554, 2000.*
Jiachong Cheng et al, "Stereospecific synthesis of deoxyharringtonine and homoharringtonine", Chemical Abstracts, Accession No. 103:160738, XP002163590, Abstract; Figure 313, & Yoaxue Xuebao (1984) 19(3), 178–83.

Hiroshi Morita et al, "Cephalezomines A–F, potent cytotoxic alkaloids from Cephalotaxus harringtonia var. nana", *Tetrahedron* (2000), 56(19), 2929–2934, XP004198001.
Ichiro Takano et al, "New Cephalotaxus Alkaloids from Cephalotaxus harringtonia var. drupacea", *J. Nat. Prod.* (1996), 59(10), 965–967, XP002163587.
Yongkeng Wang et al, "Synthesis of homoharringtonine and separation of its stereomers", Database accession No. 103:71569, XP002163591, Abstract; Figure 315 & Huaxue Xuebao (1985), 43(2), 161–7.

(List continued on next page.)

*Primary Examiner*—Brenda Coleman
(74) *Attorney, Agent, or Firm*—Burns, Doane, Swecker & Mathis L.L.P.

(57)    ABSTRACT

The present invention concerns a compound of formula (I)

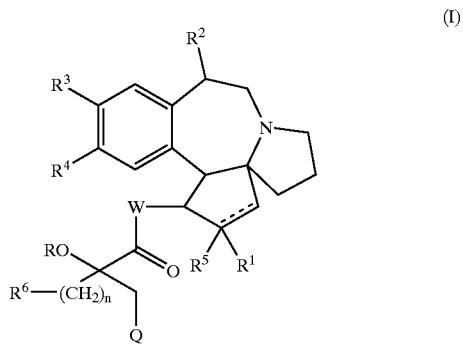

wherein:
  W represents O or NH,
  Q represents an unbranched or branched, saturated or unsaturated or aromatic, cyclic or acyclic or heterocyclic hydrocarbon radical containing 1 to 30 carbon atoms including or not heteroatom(s),
  $R^1$ is H, OH, or OMe, O-($C_1$–$C_{30}$)-alkyl, O-aryl-($C_1$–$C_{30}$)-alkyl, O-($C_2$–$C_{30}$)-alkenyl, O-($C_3$–$C_{30}$)-cycloalkyl or null, and
  $R^2$ is H or OH, or $R^1$ and $R^2$ form together —O—,
  $R^3$=$R^4$=OMe or $R^3$ and $R^4$ form together —OCH$_2$O—,
  R is H, $C_1$–$C_{30}$ alkyl or O-protecting group and $R^6$ represents an unbranched or branched, saturated or unsaturated or aromatic, cyclic or acyclic or heterocyclic hydrocarbon radical containing 1 to 30 carbon atoms including or not heteroatom(s), or R and $R^6$ form together —CMe$_2$—,
  n is 0 to 8,
  $R^5$ is H, OH, OMe, O-($C_1$–$C_{30}$)-alkyl, O-aryl-($C_1$–$C_{30}$)-alkyl, O-($C_2$–$C_{30}$)-alkenyl, O-($C_3$–$C_{30}$)-cycloalkyl or O-aryl,
  the dotted line is null or forms a double bond depending on the meaning of $R^1$.

It also concerns their methods of preparation and their use in treatment of cancers, leukemias, parasites and as reversal agents of harringtonines.

17 Claims, No Drawings

OTHER PUBLICATIONS

Sayoko Hiranuma et al, "Studies in Cephalotaxus Alkaloids, Stereospecific Total Synthesis of Homoharringtonine", *J. Org. Chem.* (1983), 48(26), 5321–6, XP002087582.

Puzhu Cong, "Mass spectroscopic study of cephalotaxine alkaloids", Chemical Abstracts, Database accession No. 99:54042, XP002163592, Abstract; Figure 318 & Yaoxue Xuebao (1983), 18(3), 215–226.

S. Hiranuma et al, "Synthesis of Hemoharringtonine and its Derivative by Partial Esterificaition of Cephalotaxine", *Tetrahedron Lett.* (1982), 23(34), 3431–4, XP002163588.

Yulin Li et al, "New synthetic method for harringtonine", Chemical Abstracts, Database accession No. 98:16906, XP002163593, Abstract; Figure 324 & Lanzhou Daxue Xuebao, Ziran Kexueban (1982), 18(3), 126.

Shu–Wen Li et al, "A study on the deoxyharringtonine and its analogs", Chemical Abstracts, Database accession No. 85:108857, XP002163594, Abstract; Figure 328 & Hua Hsueh Hsueh Pao (1975), 33(1), 75–8.

K. L. Mikolajczak et al, "Partial synthesis of harringtonine analogs", *J. Pharm. Sci.*, (1974), 63(8), 1280–3, XP002163589.

PCT/IB 00/01593 International Search Report, date of mailing: Apr. 12, 2001.

* cited by examiner

CEPHALOTAXANES: THEIR METHOD OF PREPARATION AND THEIR USE IN TREATMENT OF CANCERS, LEUKEMIAS, PARASITES, INCLUDING THOSE RESISTANT TO USUAL CHEMOTHERAPEUTIC AGENTS, AND AS REVERSAL AGENTS

This application is a continuation of PCT/IB00/01593, filed Oct. 17, 2000, which designates the United States.

The present invention concerns new cephalotaxanes, their methods of preparation and their use in treatment of cancers, leukemias, parasites including thus resistant to usual chemotherapeutic agents and as reversal agents of harringtonines.

Cephalotaxanes (CTX) are particular alkaloids today only extracted from the Cephalotaxaceae family which exhibiting the structural formula 1.

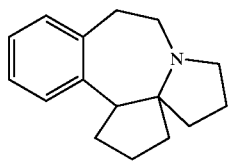

Several substituents may be encountered on this core: hydroxyl, ether, acyloxy etc. Some double bound or intramolecular bridge achieve to definite cephalotaxanes. Several dozen of cephalotaxanes have been isolated from various cephalotaxus species.

Cephalotaxoids include cephalotaxanes and unnatural analogs of cephalotaxanes.

Cephalotaxines 2 are cephalotaxanes without acyloxy side-chain.

Harringtonines (i.e. harringtonine=HA and homoharringtonine=HHT) are natural esters of cephalotaxines exhibiting generally a strong cytotoxic activity, Harringtonines are natural esters of cephalotaxines exhibiting generally a strong cytotoxic activity.

Harringtoids include harringtonines and unnatural analogs of harringtonines.

Two harringtonines are very promising drugs in the treatment of certain leukemia such as Chronic Myelogenous Leukemia (CML). Definite activity of HHT was observed in acute myelogenous leukemia (AML), acute promyelocytic leukemia (APL), and myelodysplastic syndrome (MDS) (Warrell Jr Rpet al, 3:617–621, 1985; Feldman E et al., Leukemia 6:1185–88, 1992; Feldman E J et al, Leukemia 10:40–42, 1996; Kantarjian H et al., Cancer 63:813–817, 1989; Kantarjian H et al., J Clin Oncol 18:3513–3521,2000). The present applicant have initiated in France compassionate use of HHT in CML patients resistant or not eligible to all existing therapies and several phase II and III clinical trials including in patient with CML and AML are ongoing in France and in the U.S. However, it should be pointed out that harringtonines pertain to the series of natural drugs exhibiting the multiresistance phenomenon which led to relapse of the cancer diseases. This situation is a serious limitation to the use of natural chemotherapeutic agents in the treatment of cancers and leukemia.

Harringtonine inhibit protein synthesis at the level of elongation, however ultimate mechanism of action of harringtonine remain unknown. The final result is the self-destruct of the cell. Clinically, harringtonines have a selective action in leukemia of the myeloid series. In addition, harringtonines interacts with P Glycoprotein (PGP) and Multiresistance Protein (MRP). PGP, MRP and other efflux pumps are complex molecular entities which are ubiquist in nature. Their role is to selectively efflux the environmental natural toxic agents, including agents of chemotherapy (anthracyclines, taxanes, epipodophyllotoxins, harringtonine, etc.) It was pointed out that no common structural feature of this natural cytotoxic may related to molecular recognizing by PGP.

A number of analogs all less active than harringtonines have been synthesized. The more active among these esters are about one magnitude less cytotoxic than harringtonines in vitro (i.e. HA, HHT neoharringtonine, have an activity= IC50 ranged from 10 to 30 ng per mL, whereas analog previously synthesized have an IC50 higher than 100 ng/mL). No relation structure activity relationship had been previously found since the discovering of harringtonines.

Therefore, there is the need of new analogs of harringtonines having the same magnitude of cytotoxicity than harringtonines in vitro.

Surprisingly, the present applicant have synthesized a series of CTX analogs exhibiting stronger in vitro inhibition of leukemic cell lines such as K562, than HHT used as reference.

The present invention provides cephalotaxanes having formula (I)

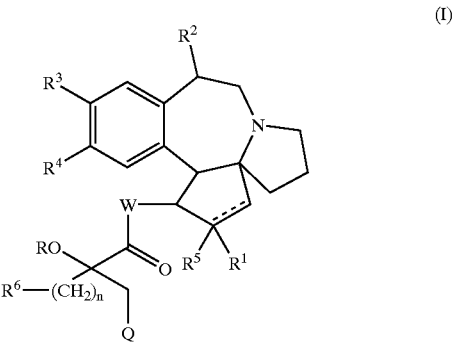

wherein

W represents O or NH

Q represents an unbranched or branched, saturated or unsaturated or aromatic, cyclic or acyclic or heterocyclic hydrocarboned radical containing 1 to 30 carbon atoms including or not heteroatom(s), $R^1$ is H, OH, OMe, O—($C_1$–$C_{30}$)alkyl, O-aryl($C_1$–$C_{30}$) alkyl, O—($C_2$–$C_{30}$)alkenyl, O—($C_3$–$C_{30}$)cycloalkyl or null and $R^2$ is H or OH, or $R^1$, $R^2$ form together —O—, $R^3$=$R^4$=OMe or $R^3$ and $R^4$ form together —OCH$_2$O—, R is H, $C_1$–$C_{30}$alkyl or O-protecting group and $R^6$ represents an unbranched or branched, saturated or unsaturated or aromatic, cyclic or acyclic or heterocyclic hydrocarboned radical containing 1 to 30 carbon atoms including or not heteroatom(s), or R and $R^6$ form together —CMe$_2$—, n is 0 to 8, $R^5$ is H, OH, OMe, O—($C_1$–$C_{30}$)alkyl, O-aryl($C_1$–$C_{30}$) alkyl, O—($C_2$–$C_{30}$)alkenyl, O—($C_3$–$C_{30}$)cycloalkyl or O-aryl, the doted line is null or forms a double bond depending on the meaning of $R^1$, except for compounds where W represents O, the doted line forms a double bond, $R^1$ is null, $R^2$ is H, $R^3$ and $R^4$ represent —O—CH$_2$—O—, $R^5$ is OMe, Q=CO$_2$$R^7$ and 1.) R=H, $R^6$=—(C—OH)Me$_2$, n=2 or 3, $R^7$=Me or H,
2.) R=H, $R^6$=—(C—H)Me$_2$, n=2 to 4, $R^7$=Me,
3.) R=H, $R^6$=—(C—H)Me$_2$, n=1 or 2, $R^7$=H,
4.) R=H, $R^6$=Ph, n=1 to 3, $R^7$=Me,
5.) R=H, $R^6$=—CH=CH—Ph, n=0, $R^7$=Me,
6.) R=H, $R^6$=CH$_3$, n=4, $R^7$=Me,
7.) R and $R^6$ form together —CMe$_2$—, n=2 or 3, $R^7$=Me, W represents O, the doted line forms a double bond, $R^1$ is null, $R^2$ is OH, $R^3$ and $R^4$ represent —O—CH2—O—, $R^5$ is OMe and R=H, $R^6$=—(C—H)Me$_2$, n=2 or 3, $R^7$=Me W represents O, the doted line is null, $R^1$ and $R^2$ represent —O—, $R^3$ and $R^4$ represent —O—CH$_2$—O—, $R^5$ is OMe and R=H, $R^6$=—(C—H)Me$_2$, n=2, $R^7$=Me.

The term "O-Protecting group" as used in the present invention refers to a substituent which protects hydroxyl groups against undesirable reactions during synthetic procedures such as those O-protecting groups disclosed in Greene, "Protective Groups In Organic synthesis", (John Wiley & Sons, New York (1981)). O-protecting groups comprise substituted methyl ethers, for example, methoxymethyl, benzyloxymethyl, 2-methoxyethoxymethyl, 2-(trimethylsilyl) ethoxymethyl, t-butyl, benzyl and triphenylmethyl, tetrahydropyranyl ethers, substituted ethyl ethers, for example, 2,2,2-trichloroethyl, silyl ethers, for example, trimethylsilyl, t-butyidimethylsilyl and t-butyldiphenylsilyl; and esters prepared by reacting the hydroxyl group with a carboxylic acid for example, acetate, propionate, benzoate and the like.

The term "$C_1$–$C_{30}$alkyl" as used in the present invention refers to straight or branched chain substituted or unsubstituted alkyl radicals containing from 1 to 30 carbon atoms including, but not limited to, methyl, ethyl, n-propyl, iso-propyl, n-butyl, iso-butyl, sec-butyl, t-butyl, n-pentyl, n-hexyl and the like.

The term "$C_2$–$C_{30}$alkenyl" as used in the present invention refers to straight or branched chain substituted or unsubstituted alkenyl radicals containing from 1 to 30 carbon atoms including, but not limited to, ethenyl, propenyl, butenyl, pentenyl, hexenyl and the like.

The term "aryl" as used in the present invention refers to a monocyclic or bicyclic carbocyclic ring system having one or more aromatic rings including, but not limited to, phenyl, naphthyl, tetrahydronaphthyl, indanyl and the like. Aryl groups can be unsubstituted or substituted with one or more substituents.

The term "aryl($C_1$–$C_{30}$)alkyl" as used in the present invention refers to an aryl group such as defined above appended to a $C_1$–$C_{30}$alkyl radical such as defined above, for example, benzyl and the like.

The term "$C_3$–$C_{30}$cycloalkyl" as used herein refers to a carbocyclic ring having 3 to 30 carbon atoms including, but not limited to, cyclopropyl, cyclopentyl, cyclohexyl and the like. Cycloalkyl groups can be unsubstituted or substituted with one or more substituents.

An advantageous embodiment provides compounds of formula (I) wherein
Q=COZ—$R^8$,
Z=O, S, or NH, and

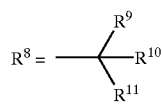

or Z—$R^8$ is $NR^{12}R^{13}$, $R^{12}$ and $R^{13}$ representing respectively $R^9$ and $R^{10}$, $R^9$, $R^{10}$, $R^{11}$ are independently H, $C_1$–$C_{30}$alkyl, $C_3$–$C_{30}$cycloalkyl, aryl, aryl-($C_1$–$C_{30}$)-alkyl, $C_2$–$C_{30}$alkenyl, $C_2$–$C_{30}$alkynyl, $C_1$–$C_{30}$trihalogenoalkyl, $C_1$–$C_{30}$alkylamino-($C_1$–$C_{30}$)-alkyl, $C_1$–$C_{30}$dialkylamino-($C_1$–$C_{30}$)-alkyl, or amino-($C_1$–$C_{30}$)-alkyl, or

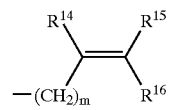

where $R^{14}$, $R^{15}$, $R^{16}$ are independently H, halogen, $C_1$–$C_{30}$ alkyl, $C_3$–$C_{30}$ cycloalkyl, aryl, aryl-($C_1$–$C_{30}$)-alkyl, $C_2$–$C_{30}$ alkenyl or $C_2$–$C_{30}$ alkynyl, $C_1$–$C_{30}$ trihalogenoalkyl, m is 0 to 4,
each of these groups including or not heteroatom(s), such as in particular S, N or O.

The term "$C_2$–$C_{30}$alkynyl" as used in the present invention refers to straight or branched chain substituted or unsubstituted alkynyl radicals containing from 1 to 30 carbon atoms including, but not limited to, ethynyl, propynyl, butynyl, pentynyl, hexynyl, heptynyl and the like.

The term "$C_1$–$C_{30}$trihalogenoalkyl" as used in the present invention refers to straight or branched chain alkyl radicals containing from 1 to 30 carbon atoms substituted by three halogen atoms.

The term "$C_1$–$C_{30}$alkylamino" as used in the present invention refers to $R^{18}$NH— wherein $R^{18}$ is a $C_1$–$C_{30}$alkyl group such as defined above.

The term "$C_1$–$C_{30}$dialkylamino" as used herein refers to $R^{19}R^{20}$N— wherein $R^{19}$ and $R^{20}$ are independently selected from $C_1$–$C_{30}$alkyl such as defined above.

The term "$C_1$–$C_{30}$aminoalkyl" as used herein refers to a $C_1$–$C_{30}$alkyl radical such as defined above to which is appended an amino group (—NH$_2$).

The term "$C_1$–$C_{30}$alkylamino-($C_1$–$C_{30}$)-alkyl" as used herein refers to a $C_1$–$C_{30}$alkyl radical such as defined above to which is appended an $C_1$–$C_{30}$alkylamino group such as defined above.

The term "$C_1$–$C_{30}$dialkylamino-($C_1$–$C_{30}$)-alkyl" as used herein refers to a $C_1$–$C_{30}$alkyl radical such as defined above to which is appended an $C_1$–$C_{30}$dialkylamino group such as defined above.

Another advantageous embodiment provides compounds of formula (I) wherein:

$R^6$=—(C—Y)Me$_2$, —CH=CMe$_2$, or an aryl group or R and $R^6$ form together —CMe$_2$—, Y=H, OH or halogen.

A further advantageous embodiment provides compounds of formula (I) wherein.

the doted line forms a double bond
$R^1$ is null
$R^2$ is H
$R^3$ and $R^4$ represent —O—CH$_2$—O—
$R^5$ is OMe.

A further aspect of the invention provides compounds of formula (I) wherein:

the doted line is null

R¹ and R² represent —O—

R³ and R⁴ represent —O—CH₂—O—

R⁵ is OMe.

Yet, a further preferred embodiment provides compounds of formula (I) wherein n=1 to 3.

Another further aspect of the invention provides compounds of formula (I) wherein W represents O.

Advantageously, a compound according to the present invention is selected from the group consisting of the following compounds 1 to 65:

1
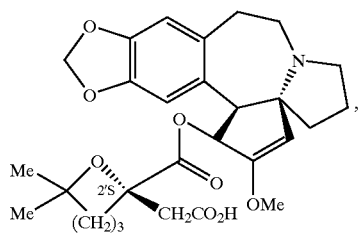

2
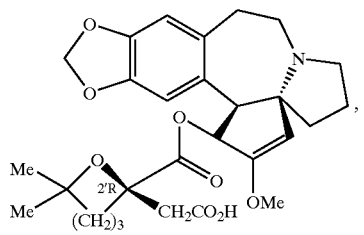

3
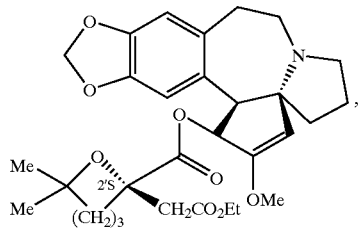

4
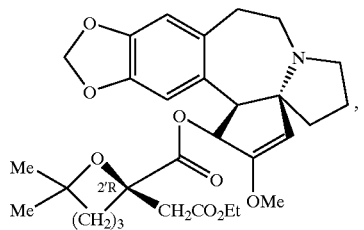

5
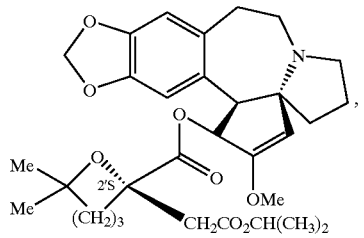

6
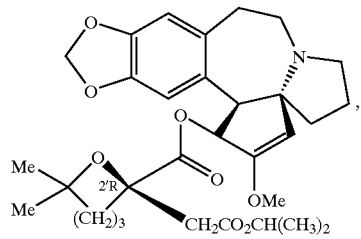

7
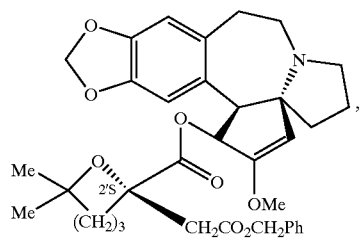

8
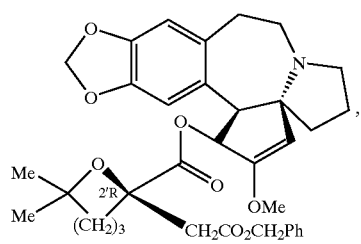

9
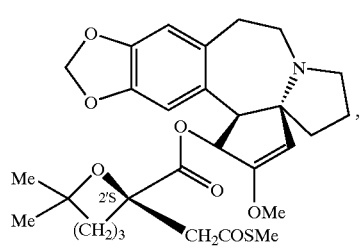

10
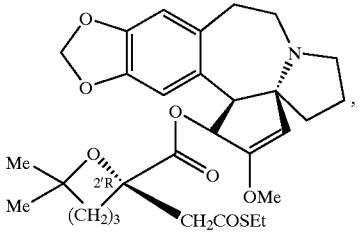

11
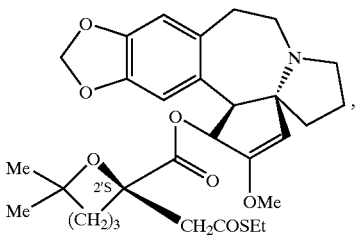

12
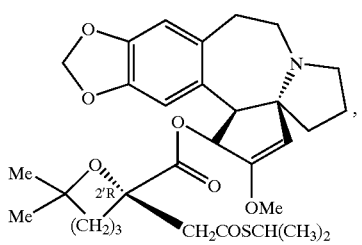
13
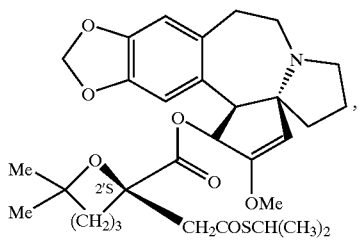
14
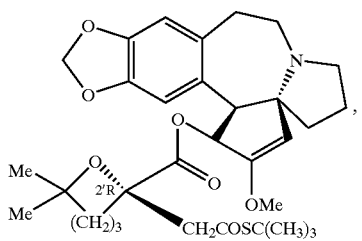
15
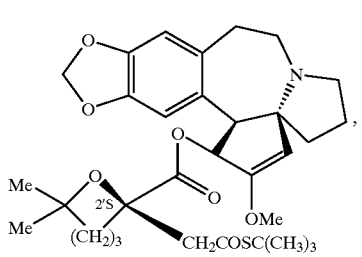
16
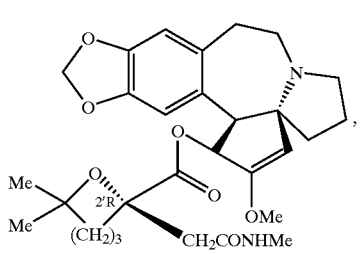
17
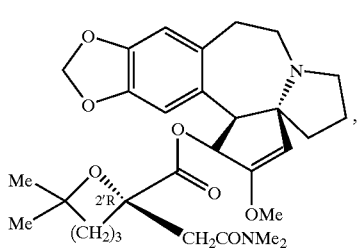
18
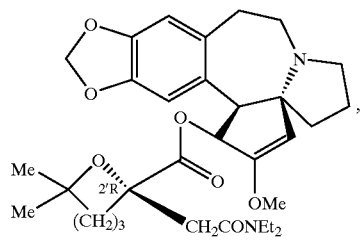
19
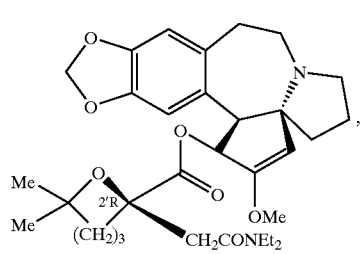
20
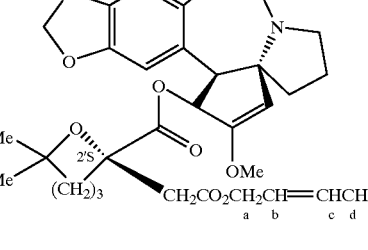
21
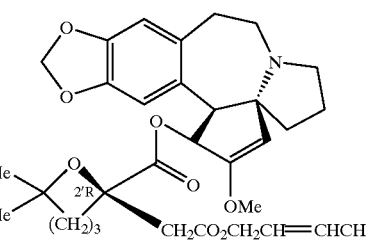
22
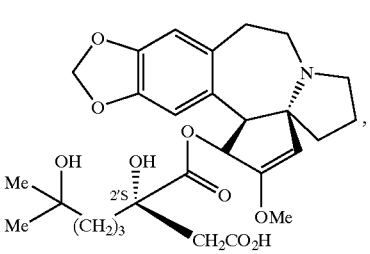
23
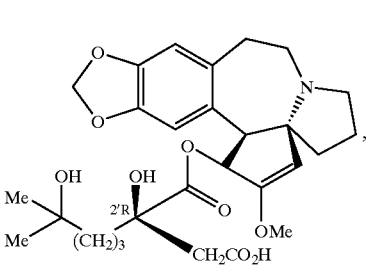

-continued
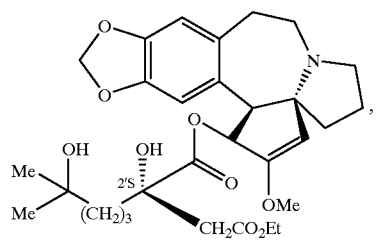
24
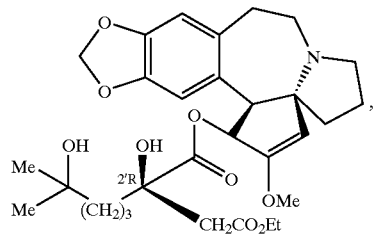
25
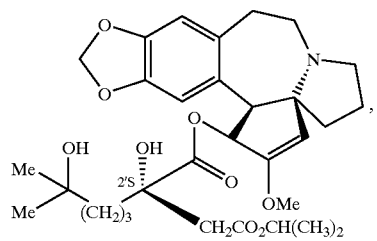
26
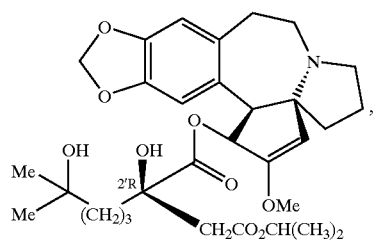
27
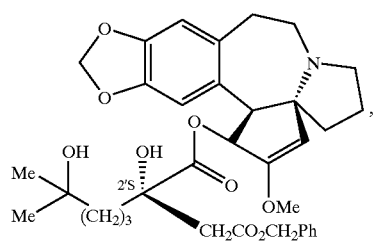
28
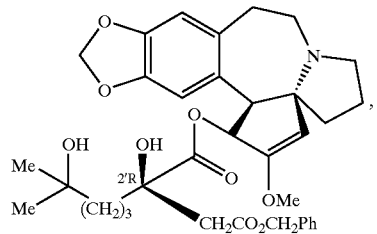
29
-continued
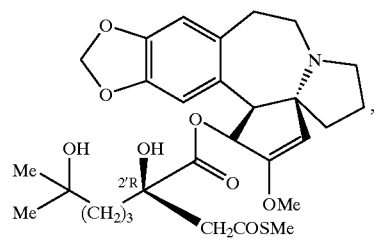
30
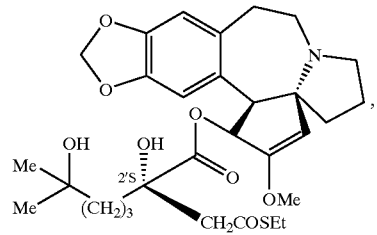
31
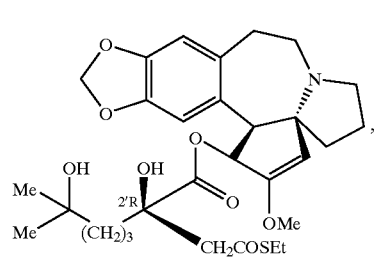
32
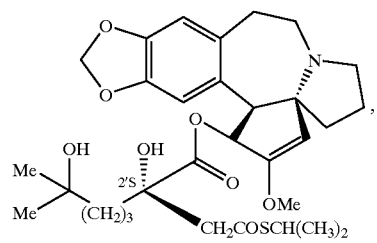
33
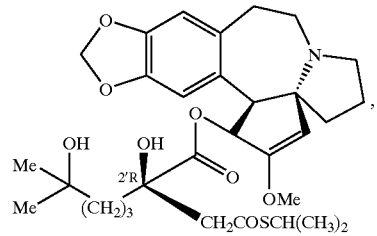
34
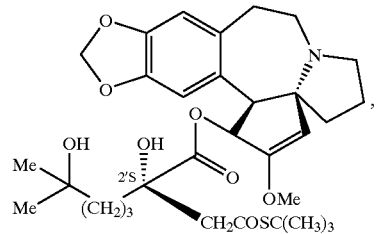
35

-continued

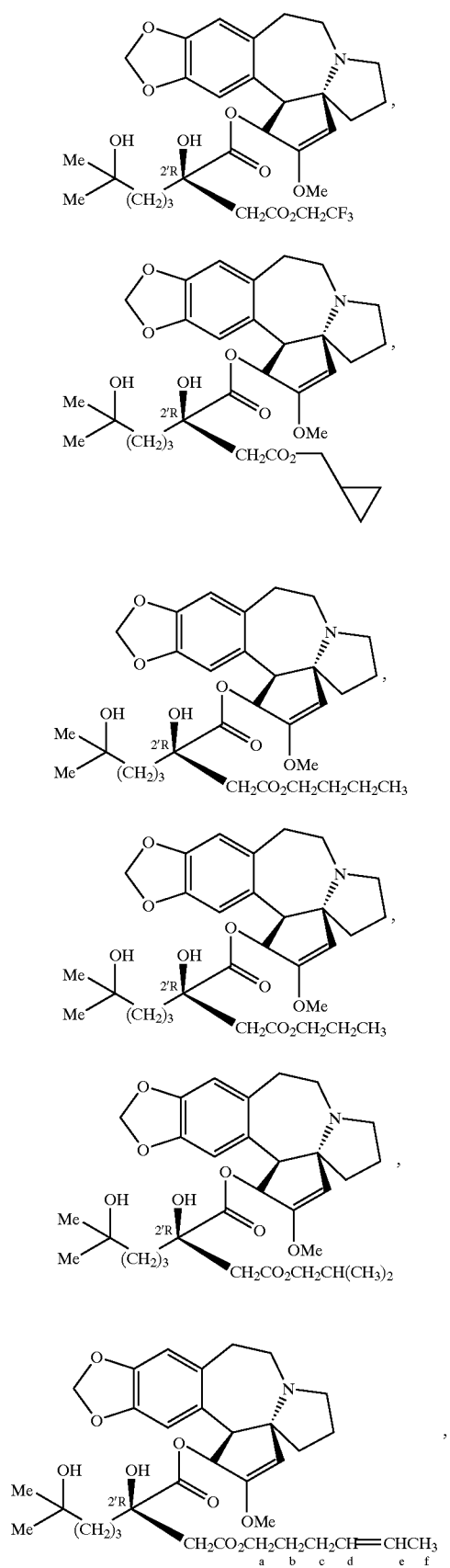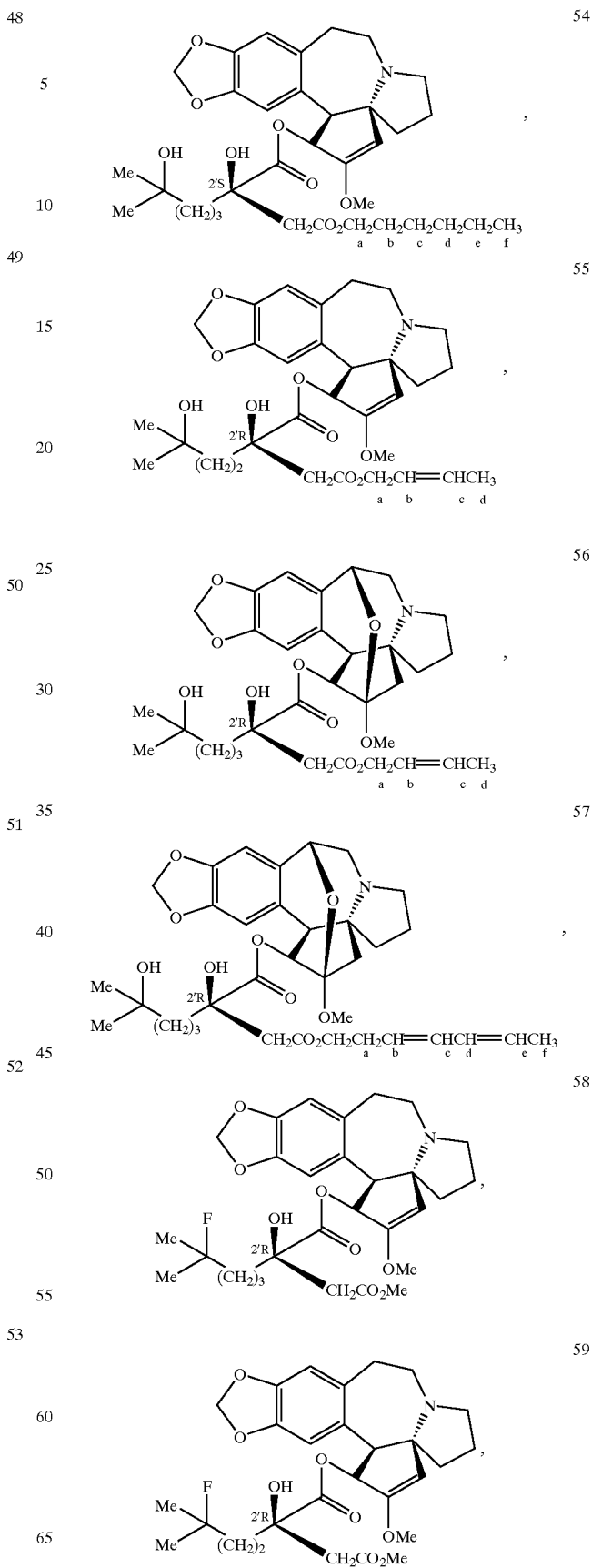

-continued

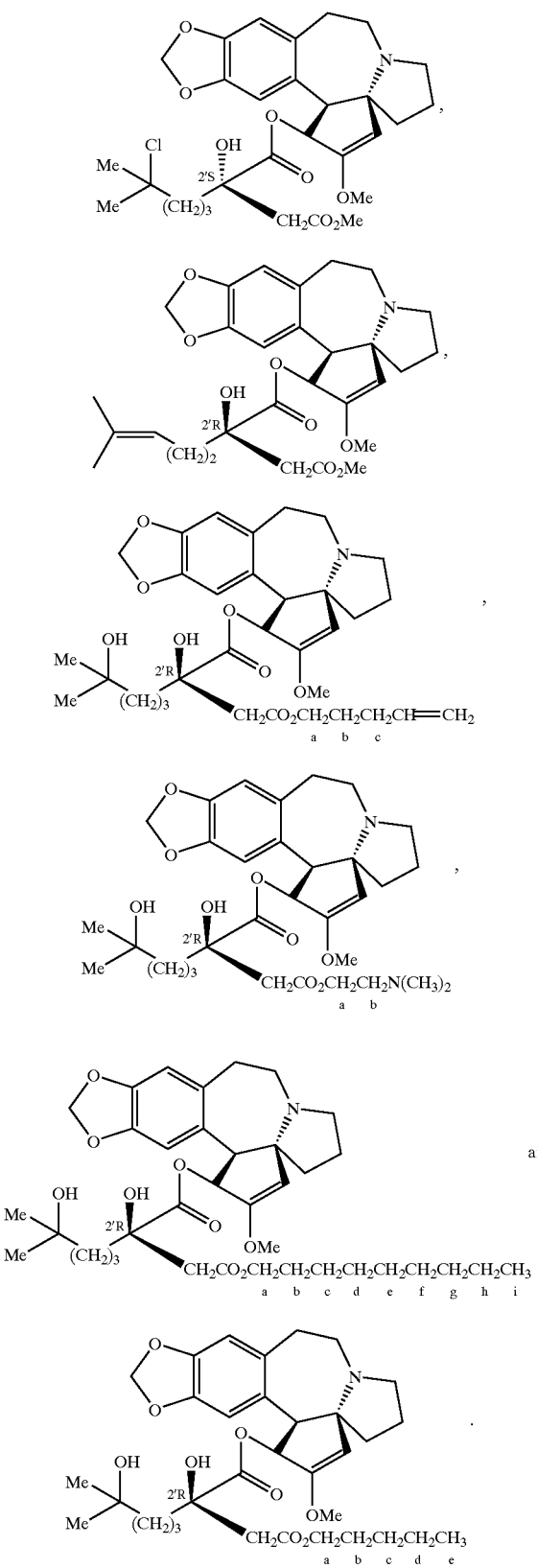

The advantageous compounds of the present invention are the one of formula (I) wherein Q represents COZR⁸, Z is such as described above and $R^8$ has 6 carbon atoms without any hydrophilic group.

Some of the compounds described herein contain one or more centers of asymmetry and may thus give rise to diastereoisomers and optical isomers. The present invention is meant to comprehend such possible isomers or diastereoisomers alone or in a mixture, such as for example their racemic mixture.

Some of the compounds described herein contain olefinic double bonds and are meant to include both E and Z geometric isomers.

Another aspect of the invention is a process for preparing a compound of formula (I).

A. In the case where W represents NH, it comprises the following steps A1 to A2:

A1: reacting cephalotaxines of formula V:

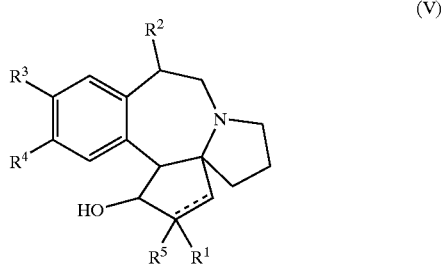

(V)

wherein
$R^1$ is H, OH, OMe, O—($C_1$–$C_{30}$)alkyl, O-aryl($C_1$–$C_{30}$) alkyl, O—($C_2$–$C_{30}$)alkenyl, O—($C_3$–$C_{30}$)cycloalkyl or null and $R^2$ is H or OH, or $R^1$, $R^2$ form together —O—,
$R^3$=$R^4$=OMe or $R^3$ and $R^4$ form together —OCH$_2$O—,
$R^5$ is H, OH, OMe, O—($C_1$–$C_{30}$)alkyl, O-aryl($C_1$–$C_{30}$) alkyl, O—($C_2$–$C_{30}$)alkenyl, O—($C_3$–$C_{30}$)cycloalkyl or O-aryl,
the doted line is null or forms a double bond depending on the meaning of $R^1$
by methods known by the one skilled in the art to obtain the compounds of formula VI

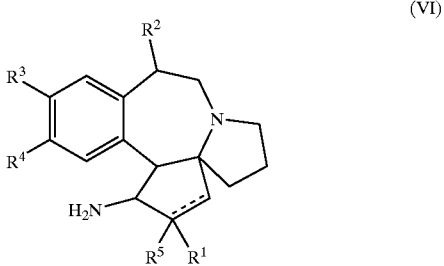

(VI)

wherein
$R^1$ is H, OH, OMe, O—($C_1$–$C_{30}$)alkyl, O-aryl ($C_1$–$C_{30}$)alkyl, O—($C_2$–$C_{30}$)alkenyl, O—($C_3$–$C_{30}$)cycloalkyl or null and $R^2$ is H or OH, or $R^1$, $R^2$ form together —O—,
$R^3$=$R^4$=OMe or $R^3$ and $R^4$ form together —OCH$_2$O—,
$R^5$ is H, OH, OMe, O—($C_1$–$C_{30}$)alkyl, O-aryl ($C_1$–$C_{30}$)alkyl, O—($C_2$–$C_{30}$)alkenyl, O—($C_3$–$C_{30}$)cycloalkyl or O-aryl,
the doted line is null or forms a double bond depending on the meaning of $R^1$ For example, such methods are the following:
substituting the hydroxyl group of the cephalotaxines of formula V by an halogen or a tosylate by methods known by the one skilled in the art (such as by using $SOCl_2$), then substituting the halogen or the tosylate by the group $NH_2$ by methods known by the one skilled in the art (such as 1) the use of gaseous ammoniac in methylene chloride at 0°C. and 1 atm or 2) the use of $NaN_3$ in DMF followed by $2_1$) a catalytic hydogenolysis with for example Pd/C as the catalyst or $2_2$) the use of $LiAlH_4$) to obtain the compounds of formula VI.

A2: reacting the compounds of formula VI by the methods disclosed in WO 99/48894.

B. In the case where W represents O, Q=$COR^8$ and $R^8$ is such as described above, it comprises the step of reacting harringtonines or homoharringtonines commercially available (by SIGMA) with organometallic compounds, advantageously organolithium or grignard reagent.

C. In the case where W represents O, Q=$CH_2ZR^8$ or $CH_2R^8$ and Z and $R^8$ are such as described above, it comprises the step of reducing harringtonines or homoharringtonines commercially available (by SIGMA) with an hydride, advantageously boron or aluminium hydride D. In the case where W represents O, Q=COZ—$R^8$ and Z and $R^8$ are such as described above, it comprises the following steps i) then ii),
i) hydrolyzing selectively the compound of formula (IV) which is available commercially

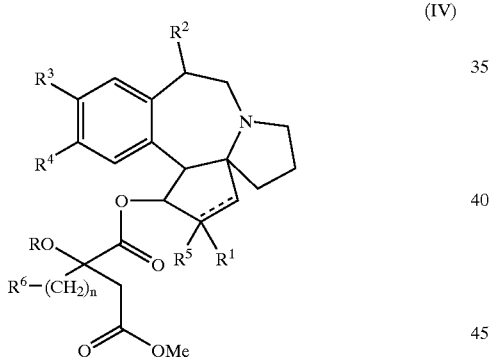

such as mineral hydroxide, advantageously lithium, potassium or sodium hydroxide, in hydro-organic solvent mixture to give as reaction product, amphoteric acid of formula (III)

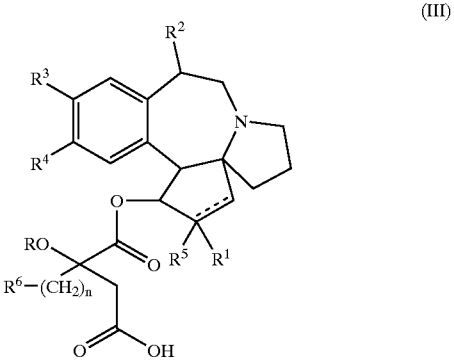

wherein $R^1$ to $R^5$, R and $R^6$ are defined as above,
ii) performing the esterification of the above obtained amphoteric acid of formula (III) with an esterification agent and a compound of formula $R^8$—ZH, $R^8$ and Z being defined as above
and wherein the steps i) and ii) are carried out successively or simultaneously.

Advantageously the compounds of the following formula (II):

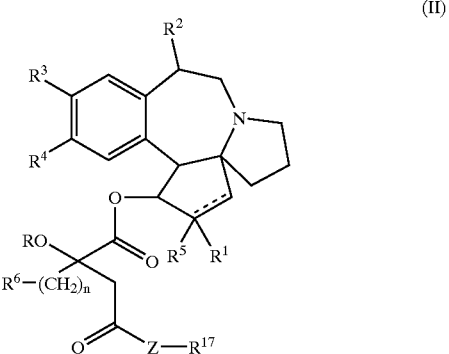

wherein
$R^1$ is H, OH, OMe, O—($C_1$-$C_{30}$)-alkyl, O-aryl-($C_1$-$C_{30}$)-alkyl, O—($C_2$-$C_{30}$)-alkenyl, O—($C_3$-$C_{30}$)-cycloalkyl or null and $R^2$ is H or OH, or $R^1$ and $R^2$ form together —O—
$R^3$=$R^4$=OMe or $R^3$ and $R^4$ form together —OCH$_2$O—
R is H, $C_1$-$C_{30}$alkyl or O-protecting group and $R^6$ represents an unbranched or branched, saturated or unsaturated or aromatic, cyclic or acyclic or heterocyclic hydrocarboned radical containing 1 to 30 carbon atoms, including or not heteroatom(s), or R and $R^6$ form together —CMe$_2$—
n is 0 to 8.
$R^5$ is H, OH, OMe, O—($C_1$-$C_{30}$)-alkyl, O-aryl-($C_1$-$C_{30}$)-alkyl, O—($C_2$-$C_{30}$)-alkenyl, O—($C_3$-$C_{30}$)-cycloalkyl or O-aryl.
the doted line is null or forms a double bond depending on the meaning of $R^1$, wherein
$R^1$ is H, OH, OMe, O—($C_1$-$C_{30}$)-alkyl, O-aryl-($C_1$-$C_{30}$)-alkyl, O—($C_2$-$C_{30}$)-alkenyl, O—($C_3$-$C_{30}$)-cycloalkyl or null and $R^2$ is H or OH, or $R^1$ and $R^2$ form together —O—
$R^3$=$R^4$=OMe or $R^3$ and $R^4$ form together —OCH$_2$O—
R is H, $C_1$-$C_{30}$alkyl or O-protecting group and $R^6$ represents an unbranched or branched, saturated or unsaturated or aromatic, cyclic or acyclic or heterocyclic hydrocarboned radical containing 1 to 30 carbon atoms, including or not heteroatom(s), or R and $R^6$ form together —CMe$_2$—
n is 0 to 8.
$R^5$ is H, OH, OMe, O—($C_1$-$C_{30}$)-alkyl, O-aryl-($C_1$-$C_{30}$)-alkyl, O—($C_2$-$C_{30}$)-alkenyl, O—($C_3$-$C_{30}$)-cycloalkyl or O-aryl.
the doted line is null or forms a double bond depending on the meaning of $R^1$, Z=O or S, and R$^{17}$ represents C$_1$–C$_{30}$alkyl, C$_2$–C$_{30}$alkenyl, C$_3$–C$_{30}$cycloalkyl, C$_2$–C$_{30}$alkynyl, aryl-(C$_1$–C$_{30}$)-alkyl or aryl and advantageously methyl or ethyl, can also be used instead of the compounds of formula IV to prepare, according to the process A, the product of formula (I).

Advantageously, the esterification agent in process A is a lewis acid or a protonic acid.

In an advantageous embodiment of the process A according to the present invention, the amphoteric acid of formula (III) is activated with an imide or by formation of a mixte anhydride or an acid chloride.

Advantageously, the imide is dicyclohexylcarbodiimide or diisopropylcarbodiimide More advantageously the mixte anhydride is formed with 2,4,6-trichlorobenzoic acid by contact with 2,4,6-trichlorobenzoyl chloride in the presence of a base.

In another advantageous embodiment of the process A according to the present invention, the steps i) and ii) are carried out simultaneously, without isolation of the amphoteric acid of formula (III), via a reaction of transesterification performed in presence of an acidic or basic catalyst.

Advantageously, the catalyst is a base, such as an alkaline hydride.

More advantageously, the catalyst is a lewis acid or a protonic acid.

Given their pharmacological properties, the compounds of the present invention may be used in human therapy in the treatment of cancer pathology.

This invention includes also a pharmaceutical composition which comprises a therapeutically effective amount of at least one compound according to the present invention with one or more pharmaceutically acceptable carriers, excipients or diluents.

These pharmaceutical compositions may be formulated for oral, intravenous or subcutaneous administration.

Another aspect of the invention is the use of at least one compound according to the present invention or of the pharmaceutical composition as described above as (i) chemotherapeutic agent, (ii) enhancer of other chemotherapeutic agents (iii) for inhibiting tumors growth, (iv) for inhibiting mammalian parasites, Yet, another aspect of the invention is the use of at least one compound according to the present invention for the preparation of a pharmaceutical composition as (i) chemotherapeutic agent, (ii) enhancer of other chemotherapeutic agents (iii) for inhibiting tumors growth, (iv) for inhibiting mammalian parasites, or (v) as reversal agents in particular of harringtonines. (a reversal agent is an agent able to reverse the cell multiresistance phenomenon).

Finally, the present invention describes a method for treating mammalian tumors which comprises administering to a mammal a therapeutically effective amount of at least one compound according to the present invention.

Another advantages of the compounds according to the present invention, is its activity on leukemic cell lines exhibiting resistance to other agents including harringtonines.

The following examples, which are given without implied limitation, illustrates the present invention.

EXAMPLE 1

Preparation of (−)-Cephalotaxyl(2'S)-2-carboxymethyl-6,6-dimethyl-2-tetrahydropyranecarboxylate or 4'-Demethyl-anhydro-epi-homoharringtonine

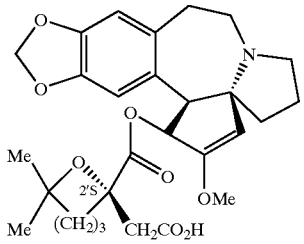

To a stirred solution of anhydro-epi-homoharringtonine (5 g, 9.48 mmol) in ethanol (162.5 ml) was added potassium hydroxide (5.35mg, 94.8 mmol) and water (50 ml). After stirring 7 hours at ambient temperature and evaporation of ethanol under reduced pressure, the residual aqueous layer is saturated with sodium chloride and extracted with dichloromethane (3×100 ml). The combined organic layers were dried over magnesium sulfate, and evaporated to dryness. The resulting crude product was purified by column chromatography (silica 15–40 μm (50 g), dichloromethane then dichloromethane/methanol, 90:10 to 75:25) to provide the expected compound (4.6 g, 95%). The product thus obtained showed the following characteristics:

$^1$H NMR 400 MHz (CDCl$_3$) (δ ppm, J Hz): 6.61 (1H, s, H-14*), 6.58 (1H, s, H-17*), 5.85 (3H, m, H-3+OCH$_2$O), 5.06 (1H, s, H-1), 3.80 (1H, d, J$_{4-3}$=9.6), H-4), 3.68 (3H, s, OCH$_3$), 3.09 (2H, m, H-11β+H-8α), 2.94 (1H, m, H-10α), 2.60 (2H, m, H-8β+H-10β), 2.37 (1H, dd, J$_{AB}$=14.0, J=6.7, H-11α), 2.16 and 1.90 (2H, 2d, J$_{AB}$=12.3, CH$_2$CO$_2$), 2.02 (1H, m, H-6$_A$), 1.90 (1H, m, H-6$_B$), 1.76 (2H, m, CH$_2$-7), 1.5–1.2 (6H, m, 3×CH$_2$), 1.26 (3H, s, CH$_3$), 1.05 (3H, s, CH$_3$).

EXAMPLE 2

Preparation of (−)-Cephalotaxyl(2'R)-2-carboxymethyl-6,6-dimethyl-2-tetrahydropyranecarboxylate or 4'-Demethyl-anhydro-homoharringtonine

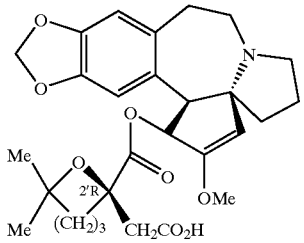

To a stirred solution of anhydro-homoharringtonine (1 g, 1.9 mmol) in ethanol (32.5 ml) was added potassium hydroxide (1,07 g, 19 mmol) and water (10 ml). After stirring 6 hours at ambient temperature and evaporation of ethanol under reduced pressure, the residual aqueous layer is saturated with sodium chloride and extracted with dichloromethane (3×25 ml). The combined organic layers were dried over magnesium sulfate, and evaporated to dryness.

The resulting crude product was purified by column chromatography (silica 15–40 μm (10 g), dichloromethane then dichloromethane/methanol, 98:2 to 80:20) to provide the expected compound (678 mg, 69.5%). The product thus obtained showed the following characteristics:

$^1$H NMR 400 MHz (CDCl$_3$) (δ ppm, J Hz): 6.64 (1H, s, H-17), 6.56 (1H, s, H-14), 5.90 (3H, br, s, H-3+OCH$_2$O), 5.07 (1H, s, H-1), 3.80 (1H, d, $J_{4-3}$=9.6, H-4), 3.71 (3H, s, OCH$_3$), 3.09 (2H, m, H-11β+H-8α), 2.95 (1H, dd, $J_{AB}$=11.6, J=6.9, H-10α), 2.59 (2H, m, H-8β+H-10α), 2.37 (1H, dd, $J_{AB}$=14.0, J=6.7, H-11α), 2.07 and 2.02 (2H, 2d, $J_{AB}$=9.6, CH$_2$CO$_2$), 1.91 (1H, m, H-6$_A$), 1.75 (3H, m, H-6B+CH$_2$-7), 1.6–1.0 (6H, m,×CH$_2$), 1.22 (3H, s, CH$_3$), 1.09 (3H, s, CH$_3$).

EXAMPLE 3

Preparation of (−)-Cephalotaxyl(2'S)-2-ethoxycarbonylmethyl-6,6-dimethyl-2-tetrahydropyranecarboxylate or 4'-Ethyl-4'-demethyl-anhydro-epi-homoharringtonine

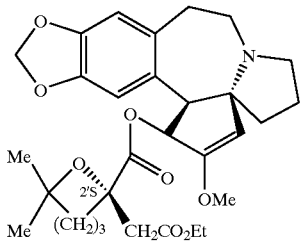

1.) Method A

A mixture of 4'-demethyl-anhydro-epi-homoharringtonine resulting from Example 1 (100 mg, 0.195 mmol) and a solution of boron trifluoride-etherate in ethanol 1.5 M (1.12 ml, 0.973 mmol) was stirred at ambient temperature for 15 hours and at 50° C. for 5 hours. After cooling of the reaction mixture, sodium hydroxide 2N was added to pH 10 and the resulting layer was extracted with dichloromethane (3×10 ml). The combined organic layers were washed with brine (50 ml), dried over magnesium sulfate and evaporated to dryness to provide the expected compound (80 mg crude, 76%). The crude product thus obtained showed the following characteristics:

$^1$H NMR 400 MHz (CDCl$_3$) (δ ppm, J Hz): 6.62 (1H, s, H-14*), 6.58 (1H, s, H-17*), 5.85 (3H, m, H-3+OCH$_2$O), 5.02 (1H, s, H-1), 4.05 (2H, m, OCH$_2$CH$_3$), 3.79 (1H, d, $J_{4-3}$=9.6, H-4), 3.65 (3H, s, OCH$_3$), 3.26 (1H, m, H-11β), 3.13 (1H, m, H-8α), 2.99 (1H, m, H-10α), 2.66 (2H, m, H-8β+H-10β), 2.43 (1H, dd, JAB=14.5, J=6.7, H-11α), 2.12 and 1.78 (2H, 2d, $J_{AB}$=14.2, CH$_2$CO2), 2.04 (1H, m, H-6$_A$), 1.88 (1H, m, H-6$_B$), 1.78 (2H, m, CH$_2$-7), 1.5–0.9 (6H, m, 3×CH$_2$), 1.22 (3H, t, J=7.2, OCH$_2$CH$_3$), 1.16 (3H, s, CH3), 1.02 (3H, s, CH$_3$).

2.) Method B

Sodium hydride 60% (0.5 mg, 0.037 mmol) was added to a solution of anhydro-epi-homoharringtonine (39 mg, 0.074 mmol) resulting from Example 1 in dry ethanol (1 ml) and the resulting mixture was stirred at ambient temperature for 48 hours. After addition of water (5 ml) the resulting aqueous layer was extracted with ether (2×5 ml). The combined organic layers were washed with brine (2×100 ml), dried over magnesium sulfate and evaporated to dryness to provide the expected product (24 mg crude, 60%). The product thus obtained showed identical characteristics to this obtained with method A.

3.) Method C

To a stirred mixture of 4'-demethyl-anhydro-epi-homoharringtonine (50 mg, 0097 mmol) resulting from Example 1 in dry dichloromethane (0.35 ml) was added at 0° C. triethylamine (dried over potassium hydroxide) (13 μl, 0.097 mmol) and 2,4,6-trichlorobenzoyl chloride (15 μl, 0.097 mmol) over a period of 10 minutes. After stirring at ambient temperature for 2 hours a solution of 4-dimethylaminopyridine (23.8 mg, 0.195 mmol) and ethanol (10 μl, 0.175 mmol) in dry dichloromethane (0.15ml) was added. After stirring at ambient temperature for 2.5 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product thus obtained (44 mg crude, 85%) showed identical characteristics to this obtained with method A.

EXAMPLE 4

Preparation of (−)-Cephalotaxyl(2'R)-2-ethoxycarbonylmethyl-6,6-dimethyl-2-tetrahydropyranecarboxylate or 4'-Ethyl-4'-demethyl-anhydro-homoharringtonine

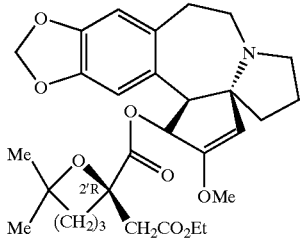

To a stirred mixture of 4'-demethyl-anhydro-homoharringtonine (256 mg, 0.498 mmol) resulting from Example 2 in dry dichloromethane (1.8 ml) was added at 0° C. triethylamine (dried over potassium hydroxide) (69 μl, 0.498 mmol) and 2,4,6-trichlorobenzoyl chloride (78 μl, 0.498 mmol) over a period of 10 minutes. After stirring at ambient temperature for 2.5 hours a solution of 4-dimethylaminopyridine (121 mg, 0.996 mmol) and ethanol (58 μl, 0.996 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (5 ml). After a last extraction of the combined aqueous layers with dichloromethane (10 ml) the combined organic layers were dried over magnesium sulfate and evaporated to dryness. The resulting crude product was purified by column chromatography (silica 15–40 μm (8 g), dichloromethane then dichloromethane/methanol, 99:1 to 97:3) to provide the expected compound (241 mg, 89%). The product thus obtained showed the following characteristics:

IR (film) (cm-1): 1735 (CO2), 1657 (C=C—O), 1504 (Ar), 1221 (C—O), 1141 (C—O), 1080 (C—O), 1034 (C—O), 930. $^1$H NMR 400 MHz (CDCl$_3$) (δ ppm, J Hz): 6.62 (1H, s, H-14*), 6.58 (1H, s, H-17*), 5.92 (1H, d, $J_{3-4}$=9.5, H-3), 5.89 and 5.81 (2H, 2s, OCH$_2$O), 5.06 (1H, s, H-1), 4.06 (2H, m, OCH$_2$CH$_3$), 3.78 (1H, d, H-4), 3.72 (3H, s, OCH₃), 3.20 (2H, m, H-11β+H-8α), 3.01 (1H, m, H-10α), 2.67 (2H, m, H-8β+H-10β), 2.41 (1H, m, H-11α), 2.14 and 1.66 (2H, 2d, JAB=14.4, C$\underline{\text{H}}$₂CO₂), 2.06 (1H, m, H-6$_A$), 1.80 (1H, m, H-6$_B$), 1.68 (2H, m, CH₂-7), 1.65–1.2 (6H, m, 3×CH₂), 1.21 (3H, t, J=7.1, OCH₂C$\underline{\text{H}}$₃), 1.10 (3H, s, CH₃), 1.01 (3H, s, CH₃).

EXAMPLE 5

Preparation of (–)-Cephalotaxyl(2'S)-2-isopropyloxycarbonylmethyl-6,6-dimethyl-2-tetrahydropyranecarboxylate or 4'-Isopropyl-4-demethyl-anhydro-epi-homoharringtonine

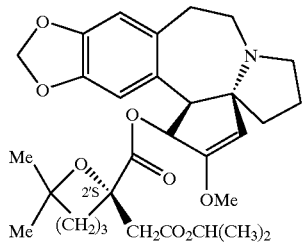

A mixture of 4'-demethyl-anhydro-epi-homoharringtonine resulting from Example 1 (100 mg, 0.195 mmol) and a solution of boron trifluoride-etherate in isopropanol 6 M (1.5 ml, 3.9 mmol) was stirred at ambient temperature for 15 hours. The reaction mixture was alkalinized to pH 10 with sodium hydroxide 2N (6 ml) and the resulting layer was extracted with dichloromethane (3×10 ml). The combined organic layers were washed with brine (10 ml), dried over magnesium sulfate and evaporated to dryness. The resulting crude product was purified by column chromatography (silica 15–40 μm (2.4 g), dichloromethane then dichloromethane/methanol, 99:1) to provide the expected compound (56 mg, 52%). %). The product thus obtained showed the following characteristics:

¹H NMR 400 MHz (CDCl₃) (δ ppm, J Hz): 6.61 (1H, s, H-14*), 6.58 (1H, s, H-17*), 5.84 (3H, m, H-3+OCH₂O), 5.02 (1H, s, H-1), 4.92 (1H, m, J=6.2, C$\underline{\text{H}}$(CH₃)₂), 3.78 (1H, d, J$_{4-3}$=9.6, H-4), 3.65 (3H, s, OCH₃), 3.24 (1H, m, H-11β), 3.09 (1H, m, H-8α), 2.94 (1H, m, H-10α), 2.60 (2H, m, H-8β+H-10β), 2.40 (1H, dd, JAB=14.4, J=6.6, H-11α), 2.08 and 1.71 (2H, 2d, J$_{AB}$=13.8, C$\underline{\text{H}}$₂CO₂), 2.01 (1H, m, H-6$_A$), 1.9–1.0 (6H, m, 3×CH₂), 1.86 (1H, m, H-6$_B$), 1.75 (2H, m, CH₂-7), 1.20 (6H, d, J=6.2, CH(C$\underline{\text{H}}$₃)₂), 1.12 (3H, s, CH₃), 1.01 (3H, s, CH₃).

EXAMPLE 6

Preparation of (–)-Cephalotaxyl(2'R)-2-isopropyloxycarbonylmethyl-6,6-dimethyl-2-tetrahydropyranecarboxylate or 4'-Isopropyl-4'-demethyl-anhydro-homoharringtonine

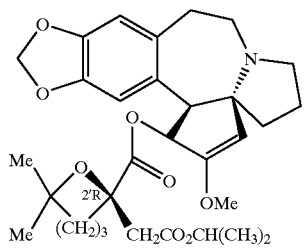

To a stirred mixture of 4'-demethyl-anhydro-homoharringtonine (255 mg, 0.498 mmol) resulting from Example 2 in dry dichloromethane (1.8 ml) was added at 0° C. triethylamine (dried over potassium hydroxide) (69 μl, 0.498 mmol) and 2,4,6-trichlorobenzoyl chloride (78 μl, 0.498 mmol) over a period of 10 minutes. After stirring at ambient temperature for 2.5 hours a solution of 4-dimethylaminopyridine (121 mg, 0.996 mmol) and isopropanol (76 μl, 0.996 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15–40 μm (8), dichloromethane then dichloromethane/methanol, 99:1 to 98:2) to provide the expected compound (216 mg, 78%). The product thus obtained showed the following characteristics:

IR (film) (cm⁻¹): 1731 (CO₂), 1656 (C=C—O), 1504 (Ar), 1223 (C—O), 1142 (C—O), 1108 (C—O), 1036 (C—O), 914. ¹H NMR 400 MHz (CDCl₃) (δ ppm, J Hz): 6.62 (1H, s, H-14*), 6.59 (1H, s, H-17*), 5.91 (1H, d, J$_{3-4}$=9.6, H-3), 5.88 and 5.79 (2H, 2s, OCH₂O), 5.04 (1H, s, H-1), 4.93 (1H, m, J=6.3, C$\underline{\text{H}}$(CH₃)₂), 3.79 (1H, d, J$_{4-3}$=9.3, H-4), 3.72 (3H, s, OCH₃), 3.19 (2H, m, H-11β+H-8α), 2.99 (1H, m, H-10α), 2.62 (2H, m, H-8β+H-10β), 2.41 (1H, m, H-11α), 2.09 and 1.70 (2H, 2d, J$_{AB}$=14.1, C$\underline{\text{H}}$₂CO2), 2.04 (1H, m, H-6$_A$), 1.91 (1H, m, H-6$_B$), 1.77 (2H, m, CH₂-7), 1.65–1.2 (6H, m, 3×CH₂), 1.19 (6H, d, J=6.3, CH(C$\underline{\text{H}}$₃)₂), 1.11 (3H, s, CH₃), 1.02 (3H, s, CH₃).

EXAMPLE 7

Preparation of (–)-Cephalotaxyl(2'S)-2-benzyloxycarbonylmethyl-6,6-dimthyl-2-tetrahydropyranecarboxylate or 4'-Benzyl-4'-demethyl-anhydro-epi-homoharringtonine

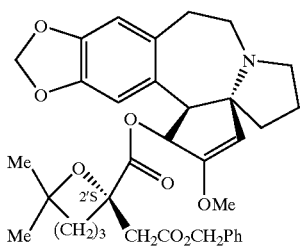

To a stirred mixture of 4'-demethyl-anhydro-epi-homoharringtonine (62 mg, 0.12 mmol) resulting from Example 1 in dry dichloromethane (0.43 ml) was added at 0° C. triethylamine (dried over potassium hydroxide) (17 μl, 0.12 mmol) and 2,4,6-trichlorobenzoyl chloride (19 μl, 0.12 mmol) over a period of 10 minutes. After stirring at ambient temperature for 2.5 hours a solution of 4-dimethylaminopyridine (29 mg, 0.14 mmol) and benzylic alcohol (25 μl, 0.24 mmol) in dry dichloromethane (0.19 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 μm (3 g), dichloromethane then dichloromethane/methanol, 99.5:0.5 to 98.5:1.5) to provide the expected compound (40 mg, 55%). The product thus obtained showed the following characteristics:

$^1$H NMR 400 MHz (CDCl$_3$) (δ ppm, J Hz): 7.35 (5H, m, Ph), 6.58 (1H, s, H-17), 6.47(1H, s, H-14), 5.81 and 5.71 (2H, 2d, J$_{AB}$=1.4, OCH$_2$O), 5.81 (1H, d, J=9.2, H-3), 5.08 and 4.99 (2H, 2d, J$_{AB}$=12.4, OC$\underline{H}_2$Ph), 5.0 (1H, s, H-1), 3.70 (1H, d, J$_{4-3}$=9.7, H-4), 3.63 (3H, s, OC$\underline{H}_3$), 3.23 (1H, m, H-11β), 3.08 (1H, m, H-8α), 2.93 (1H, m, H-10α), 2.59 (2H, m, H-8β+H-10β), 2.37 (1H, dd, J$_{AB}$=14.3, J=7.0, H-11α), 2.16 and 1.80 (2H, 2d, J$_{AB}$=14.3, C$\underline{H}_2$CO$_2$), 2.0 (1H, m, H-6$_A$), 1.90 (1H, m, H-6$_B$), 1.75 (2H, m, CH$_2$-7), 1.6–0.8 (6H, m, 3×CH$_2$), 1.07 (3H, s, CH$_3$), 1.02 (3H, s, CH$_3$).

EXAMPLE 8

Preparation of (−)-Cephalotaxyl(2'R)-2-benzyloxycarbonylmethyl-6,6-dimethyl-2-tetrahydropyranecarboxylate or 4'-Benzyl-4'-demethyl-anhydro-homoharringtonine

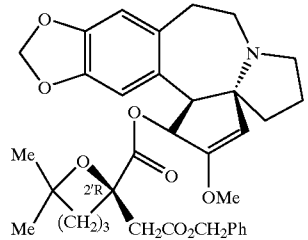

To a stirred mixture of 4'-demethyl-anhydro-homoharringtonine (255 mg, 0.496 mmol) resulting from Example 2 in dry dichloromethane (1.8 ml) was added at 0° C. triethylamine (dried over potassium hydroxide) (69 □l, 0.496 mmol) and 2,4,6-trichlorobenzoyl chloride (78 μl, 0.496 mmol) over a period of 10 minutes. After stirring at ambient temperature for 2.5 hours a solution of 4-dimethylaminopyridine (121 mg, 0.992 mmol) and benzylic alcohol (102 μl, 0.992 mmol) in dry dichloromethane (0.8 ml) was added. After stirring at ambient temperature for 15 hours, the reaction mixture was diluted with dichloromethane (0.8 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 μm (8 g), dichloromethane then dichloromethane/methanol, 99:1 to 98:2) to provide the expected compound (278 mg, 93%). The product thus obtained showed the following characteristics:

IR (film) (cm$^{-1}$): 1737 (CO$_2$), 1656 (C=C—O), 1504 (Ar), 1222 (C—O), 1141 (C—O), 1081 (C—O), 1036 (C—O), 911. $^1$H NMR 400 MHz (CDCl$_3$) (δ ppm, J Hz): 7.34 (5H, m, Ph), 6.60 (1H, s, H-17), 6.52 (1H, s, H-14), 5.91 (1H, d, J=9.8, H-3), 5.77 and 5.61 (2H, 2s, OCH$_2$O), 5.05 (2H, s, OC$\underline{H}_2$Ph), 5.03 (1H, s, H-1), 3.75 (1H, d, J$_{4-3}$=9.7, H-4), 3.67 (3H, s, OCH$_3$), 3.11 (2H, m, H-11β+H-8α), 2.93 (1H, m, H-10α), 2.59 (2H, m, H-8β+H-10β), 2.36 (1H, dd, J$_{AB}$=14.0, J=6.6, H-11α), 2.18 and 1.66 (2H, 2d, J$_{AB}$=14.5, C$\underline{H}_2$CO$_2$), 2.0 (1H, m, H-6$_A$), 1.89 (1H, m, H-6$_B$), 1.75 (2H, m, CH$_2$-7), 1.7–1.2 (6H, m, 3×CH$_2$), 1.06 (3H, s, CH$_3$), 1.04 (3H, s, CH$_3$).

EXAMPLE 9

Preparation of (−)-Cephalotaxyl(2'R)-2-methylthiocarbonylmethyl-6,6-dimethyl-2-tetrahydropyranecarboxylate or 4'-Methylthio-4'-demethoxy-anhydro-homoharringtonine

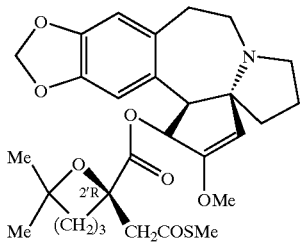

To a stirred mixture of 4'-demethyl-anhydro-homoharringtonine (404 mg, 0.786 mmol) resulting from Example 2 in dry dichloromethane (2.75 ml) was added at 0° C. triethylamine (dried over potassium hydroxide) (105 μl, 0.786 mmol) and 2,4,6-trichlorobenzoyl chloride (123 μl, 0.786 mmol) over a period of 10 minutes. After stirring at ambient temperature for 2.5 hours a solution of 4-dimethylaminopyridine (192 mg, 1.57 mmol) in dry dichloromethane (0.8 ml) and methanethiol (218 μl, 1.57 mmol) were added. After stirring at ambient temperature for 15 hours, the reaction mixture was diluted with dichloromethane (10 ml). The resulting organic layer was successively washed with water (14 ml), with saturated sodium hydrogen carbonate solution (14 ml), with brine (14 ml). The resulting aqueous layer was extracted with dichloromethane (20 ml), then the combined organic layers after drying over magnesium sulfate were evaporated to dryness. The resulting crude product was purified by column chromatography (silica 15–40 μl (12 g), dichloromethane then dichloromethane/methanol, 99:1 to 96:4) to provide the expected compound (228 mg, 53%). The product thus obtained showed the following characteristics:

IR (film) (cm$^{-1}$): 1741 (CO$_2$), 1690 (COS), 1656 (C=C—O), 1504 (Ar), 1222 (C—O), 1142 (C—O), 1078 (C—O), 1035 (C—O), 913. $^1$H NMR 400 MHz (CDCl$_3$) (δ ppm, J Hz): 6.64 (1H, s, H-14*), 6.58 (1H, s, H-17*), 5.91 (1H, d, J$_{3-4}$=9.7, H-3), 5.88 and 5.84 (2H, 2s, OCH$_2$O), 5.04 (1H, s, H-1), 3.79 (1H, H-4), 3.70 (3H, s, OCH$_3$), 3.10 (2H, m, H-11β+H-8α), 2.95 (1H, m, H-10α), 2.60 (2H, m, H-8β+H-10β), 2.35 (1H, d, J$_{AB}$=14.5, C$\underline{H}_A$COS) and (1H, m, H-11α), 2.23 (3H, s, SCH$_3$), 2.03 (1H, m, H-6$_A$), 1.90 (1H, m, H-6$_B$), 1.75 (2H, m, CH$_2$-7), 1.8–1.2 (7H, m, 3×CH$_2$+C$\underline{H}_B$COS), 1.14 (3H, s, CH$_3$), 1.03 (3H, s, CH$_3$).

EXAMPLE 10

Preparation of (−)-Cephalotaxyl(2'S)-2-ethylthiocarbonylmethyl-6,6-dimethyl-2-tetrahydropyranecarboxylate or 4'-Ethylthio-4'-demethoxy-anhydro-epi-homoharringtonine

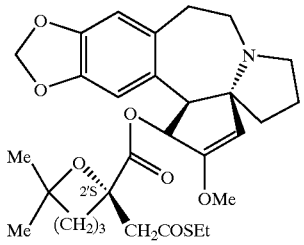

To a stirred mixture of 4'-demethyl-anhydro-epi-homoharringtonine (70 mg, 0.136 mmol) resulting from Example 1 in dry dichloromethane (0.49 ml) was added at 0° C. triethylamine (dried over potassium hydroxide) (19 μl, 0.136 mmol) and 2,4,6-trichlorobenzoyl chloride (21 μl, 0.136 mmol) over a period of 10 minutes. After stirring at ambient temperature for 2.5 hours a solution of 4-dimethylaminopyridine (33 mg, 0.272 mmol) and ethanethiol (20 μl, 0.272 mmol) in dry dichloromethane (0.25 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 μm (2 g), dichloromethane/methanol, 99:1) to provide the expected compound (40 mg, 53%). The product thus obtained showed the following characteristics:

$^1$H NMR 400 MHz (CDCl$_3$) (δ ppm, J Hz): 6.64 (1H, s, H-14*), 6.56 (1H, s, H-17*), 5.87 and 5.83 (3H, 2d, J$_{AB}$=1.5, OCH$_2$O+H-3), 5.02 (1H, s, H-1), 3.78 (1H, d, J$_{4-3}$=9.7, H-4), 3.65 (3H, s, OCH$_3$), 3.24 (1H, m, H-11β), 3.09 (1H, m, H-8α), 2.95 (1H, m, H-10α), 2.79 (2H, m, SC$\underline{H}_2$CH$_3$), 2.60 (2H, m, H-8β+H-10β), 2.41 (1H, dd, J$_{AB}$=14.2, J=7.0, H-11α), 2.28 and 1.83 (2H, 2d, J$_{AB}$=14.4, C$\underline{H}_2$COS), 2.01 (1H, m, H-6$_A$), 1.91 (1H, m, H-6$_B$), 1.75 (2H, m, CH$_2$-7), 1.5–0.85 (6H, m, 3×CH$_2$), 1.20 (3H, t, J=7.4, SCH$_2$C$\underline{H}_3$), 1.14 (3H, s, CH$_3$), 1.01 (3H, s, CH$_3$).

EXAMPLE 11

Preparation of (−)-Cephalotaxyl(2'R)-2-ethylthiocarbonylmethyl-6,6-dimethyl-2-tetrahydropyranecarboxylate or 4'-Ethylthio-4'-demethoxy-anhydro-homoharringtonine

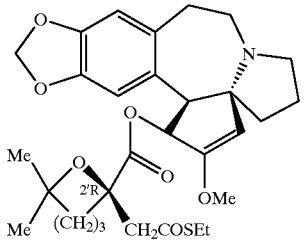

To a stirred mixture of 4'-demethyl-anhydro-homoharringtonine (250 mg, 0.486 mmol) resulting from Example 2 in dry dichloromethane (1.8 ml) was added at 0° C. triethylamine (dried over potassium hydroxide) (68 μl, 0.486 mmol) and 2,4,6-trichlorobenzoyl chloride (76 μl, 0.486 mmol) over a period of 10 minutes. After stirring at ambient temperature for 2.5 hours a solution of 4-dimethylaminopyridine (119 mg, 0.973 mmol) and ethanethiol (72 μl, 0.973 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15–40 μm (7 g), dichloromethane then dichloromethane/methanol, 99:1 to 98:2) to provide the expected compound (251 mg, 93%). The product thus obtained showed the following characteristics:

IR (film) (cm$^{-1}$): 1740 (CO$_2$), 1688 (COS), 1657 (C=C—O), 1504 (Ar), 1223 (C—O), 1142 (C—O), 1078 (C—O), 1037 (C—O), 910. $^1$H NMR 400 MHz (CDCl$_3$) (δ ppm, J Hz): 6.64 (1H, s, H-14*), 6.59 (1H, s, H-17*), 5.91 (1H, H-3), 5.90 and 5.85 (2H, 2s, OCH$_2$O), 5.03 (1H, s, H-1), 3.80 (1H, H-4), 3.71 (3H, s, OCH$_3$), 3.14 (2H, m, H-11β+H-8α), 2.88 (1H, m, H-10α), 2.81 (2H, m, SC$\underline{H}_2$CH3), 2.61 (2H, m, H-8☐+H-10β), 2.38 (1H, m, H-11☐), 2.35 (1H, d, JAB=14.8, C$\underline{H}_A$COS), 2.02 (1H, m, H-6$_A$), 1.91 (1H, m, H-6$_B$), 1.77 (2H, m, CH$_2$-7), 1.65–1.1 (7H, m, 3×CH$_2$+C$\underline{H}_B$COS), 1.20 (3H, t, J=7.4, SCH$_2$C$\underline{H}_3$), 1.14 (3H, s, CH3), 1.02 (3H, s, CH3).

EXAMPLE 12

Preparation of (−)-Cephalotaxyl(2'S)-2-isopropylthiocarbonylmethyl-6,6-dimethyl-2-tetrahydropyranecarboxylate or 4'-Isopropylthio-4'-demethoxy-anhydro-epi-homoharringtonine

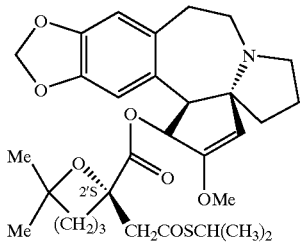

To a stirred mixture of 4'-demethyl-anhydro-epi-homoharringtonine (49 mg, 0.095 mmol) resulting from Example 1 in dry dichloromethane (0.34 ml) was added at 0° C. triethylamine (dried over potassium hydroxide) (13 μl, 0.095 mmol) and 2,4,6-trichlorobenzoyl chloride (15 μl, 0.095 mmol) over a period of 10 minutes. After stirring at ambient temperature for 2.5 hours a solution of 4-dimethylaminopyridine (23 mg, 0.19 mmol) and isopropanethiol (18 μl, 0.19 mmol) 20 in dichloromethane (0.2 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 □m (1 g), dichloromethane/methanol, 99:1) to provide the expected compound (40 mg, 74%). The product thus obtained showed the following characteristics:

$^1$H NMR 400 MHz (CDCl$_3$) (δ ppm, J Hz): 6.64 (1H, s, H-14*), 6.57 (1H, s, H-17*), 5.87 (3H, 2d, J$_{AB}$=1.4, OCH$_2$O+H-3), 5.02 (1H, s, H-1), 3.78 (1H, d, J$_{4-3}$=9.7, H-4), 3.65 (3H, s, OCH$_3$), 3.55 (1H, m, J=6.9, CH(CH$_3$)$_2$), 3.23 (1H, m, H-11β), 3.09 (1H, m, H-8α), 2.94 (1H, m, H-10α), 2.60 (2H, m, H-8β+H-10β), 2.42 (1H, dd, J$_{AB}$=13.9, J=6.8, H-11α), 2.25 and 1.79 (2H, 2d, J$_{AB}$=14.3, C$\underline{H}_2$COS), 2.04 (1H, m, H-6$_A$), 1.90 (1H, m, H-6$_B$), 1.75 (2H, m, CH$_2$-7), 1.45–0.85 (6H, m, 3×CH$_2$), 1.25 (6H, d, J=6.9, CH(C$\underline{H}_3$)$_2$), 1.14 (3H, s, CH$_3$), 1.01 (3H, s, CH$_3$).

EXAMPLE 13

Preparation of (−)-Cephalotaxyl(2'R)-2-isopropylthiocarbonylmethyl-6,6-dimethyl-2-tetrahydropyranecarboxylate or 4-Isopropylthio-4'-demethoxy-anhydro-homoharringtonine

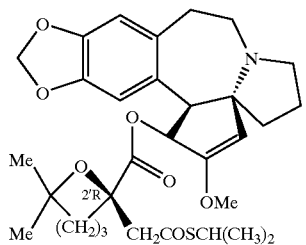

To a stirred mixture of 4'-demethyl-anhydro-homoharringtonine (248 mg, 0.483 mmol) resulting from Example 2 in dry dichloromethane (1.8 ml) was added at 0° C. triethylamine (dried over potassium hydroxide) (67 μl, 0.483 mmol) and 2,4,6-trichlorobenzoyl chloride (76 μl, 0.483 mmol) over a period of 10 minutes. After stirring at ambient temperature for 2.5 hours a solution of 4-dimethylaminopyridine (120 mg, 0.965 mmol) and iso-propanethiol (90 μl, 0.965 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15–40 □m (8 g), dichloromethane then dichloromethane/methanol, 99:1 to 98:2) to provide the expected compound (267 mg, 97%). The product thus obtained showed the following characteristics:

IR (film) (cm$^{-1}$): 1740 (CO$_2$), 1687 (COS), 1656 (C=C—O), 1504 (Ar), 1223 (C—O), 1142 (C—O), 1078 (C—O), 1036 (C—O), 912. $^1$H NMR 400 MHz (CDCl$_3$) (δ ppm, J Hz): 6.64 (1H, s, H-14*), 6.58 (1H, s, H-17*), 5.91 (1H, d, J$_{3-4}$=9.7, H-3), 5.89 and 5.85 (2H, 2s, OCH$_2$O), 5.04 (1H, s, H-1), 3.79 (1H, d, H-4), 3.71 (3H, s, OCH$_3$), 3.56 (1H, m, J=6.9, C$\underline{H}$(CH$_3$)$_2$), 3.18 (2H, m, H-11β+H-8α), 2.99 (1H, m, H-10α), 2.61 (2H, m, H-8β+H-10β), 2.39 (1H, m, H-11α), 2.31 (1H, d, J$_{AB}$=14.3, C$\underline{H}_A$COS), 2.04 (1H, m, H-6$_A$), 1.92 (1H, m, H-6$_B$), 1.78 (2H, m, CH2-7), 1.7–1.2 (7H, m, 3×CH2+C$\underline{H}_B$COS), 1.25 and 1.24 (6H, 2d, J=6.8, CH(C$\underline{H}_3$)$_2$), 1.13 (3H, s, CH3), 1.0 (3H, s, CH3).

EXAMPLE 14

Preparation of (−)-Cephalotaxyl(2'S)-2-tert-butylthiocarbonylmethyl-6,6-dimethyl-2-tetrahydropyranecarboxylate or 4'-tert-Butylthio-4'-demethoxy-anhydro-epi-homoharringtonine

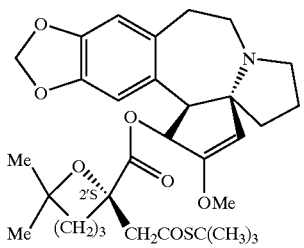

To a stirred mixture of 4'-demethyl-anhydro-epi-homoharringtonine (70 mg, 0.136 mmol) resulting from Example 1 in dry dichloromethane (0.49 ml) was added at 0° C. triethylamine (dried over potassium hydroxide) (19 μl, 0.136 mmol) and 2,4,6-trichlorobenzoyl chloride (21 μl, 0.136 mmol) over a period of 10 minutes. After stirring at ambient temperature for 2.5 hours a solution of 4-dimethylaminopyridine (33 mg, 0.272 mmol) and tert-butanethiol (31 μl, 0.272 mmol) in dry dichloromethane (0.3 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 μm (1.5 g), dichloromethane/methanol, 99:1) to provide the expected compound (46 mg, 58%). The product thus obtained showed the following characteristics:

$^1$H NMR 400 MHz (CDCl3) (δ ppm, J Hz): 6.65 (1H, s, H-14*), 6.56 (1H, s, H-17*), 5.87 and 5.84 (2H, 2d, J$_{AB}$=1.5, OCH$_2$O), 5.84 (1H, d, J$_{3-4}$=10.0, H-3), 5.02 (1H, s, H-1), 3.78 (1H, d, J$_{4-3}$=9.6, H-4), 3.64 (3H, s, OCH$_3$), 3.24 (1H, m, H-11β), 3.09 (1H, m, H-8α), 2.96 (1H, m, H-10α), 2.60 (2H, m, H-8β+H-10β), 2.42 (1H, dd, J$_{AB}$=14.3, J=7.0, H-11α), 2.20 and 1.71 (2H, 2d, J$_{AB}$=14.1, C$\underline{H}_2$COS), 2.01 (1H, m, H-6$_A$), 1.88 (1H, m, H-6$_B$), 1.75 (2H, m, CH$_2$-7), 1.6–0.85 (6H, m, 3×CH$_2$), 1.41 (9H, s, C(CH3)3), 1.13 (3H, s, C$\underline{H}_3$), 1.01 (3H, s, CH$_3$).

EXAMPLE 15

Preparation of (−)-Cephalotaxyl(2'R)-2-tert-butylthiocarbonylmethyl-6,6-dimethyl-2-tetrahydropyranecarboxylate or 4'-tert-Butylthio-4'-demethoxy-anhydro-homoharringtonine

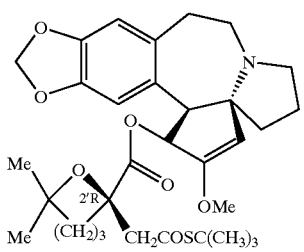

To a stirred mixture of 4'-demethyl-anhydro-homoharringtonine (234 mg, 0.455 mmol) resulting from Example 2 in dry dichloromethane (1.8 ml) was added at 0° C. triethylamine (dried over potassium hydroxide) (63 µl, 0.455 mmol) and 2,4,6-trichlorobenzoyl chloride (72 µl, 0.455 mmol) over a period of 10 minutes. After stirring at ambient temperature for 2.5 hours a solution of 4-dimethylaminopyridine (111 mg, 0.911 mmol) and tert-butanethiol (102 µl, 0.911 mmol) in dry dichloromethane (0.8 ml) was added. After stirring at ambient temperature for 15 hours, the reaction mixture was diluted with dichloromethane (5 ml). The resulting organic layer was successively washed with water (7 ml), with saturated sodium hydrogen carbonate solution (7 ml), with brine (7 ml). The resulting aqueous layer was extracted with dichloromethane (10 ml), then the combined organic layers after drying over magnesium sulfate were evaporated to dryness. The resulting crude product was purified by column chromatography (silica 15–40 µm (6 g), dichloromethane then dichloromethane/methanol, 99:1 to 98:2) to provide the expected compound (212 mg, 81%). The product thus obtained showed the following characteristics:

IR (film) (cm$^{-1}$): 1738 (CO$_2$), 1681 (COS), 1659 (C=C—O), 1504 (Ar), 1222 (C—O), 1141 (C—O), 1077 (C—O), 1037 (C—O), 911. $^1$H NMR 400 MHz (CDCl$_3$) (δ ppm, J Hz): 6.65 (1H, s, H-14*), 6.59 (1H, s, H-17*), 5.89 (3H, m, OCH$_2$O +H-3), 5.03 (1H, s, H-1), 3.76 (1H, H-4), 3.72 (3H, s, OCH$_3$), 3.13 (2H, m, H-11β+H-8α), 3.0 (1H, m, H-10α), 2.63 (2H, m, H-8β+H-10β), 2.40 (1H, m, H-11α), 2.23 (1H, d, J$_{AB}$=12.2, C$\underline{H}_A$COS), 2.01 (1H, m, H-6A), 1.93 (1H, m, H-6B), 1.78 (2H, m, CH2-7), 1.7–1.2 (6H, m, 3×CH2+C$\underline{H}_B$COS), 1.41 (9H, s, C(C$\underline{H}_3$)$_3$), 1.12 (3H, s, CH$_3$), 0.99 (3H, s, CH$_3$).

EXAMPLE 16

Preparation of (−)-Cephalotaxyl(2'S)-2-(methylamino)carbonylmethyl-6,6-dimethyl-2-tetrahydropyranecarboxylate or 4'-Methylamino-4'-demethoxy-anhydro-epi-homoharringtonine

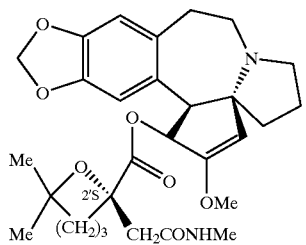

To a stirred mixture of 4'-demethyl-anhydro-epi-homoharringtonine (52 mg, 0.10 mmol) resulting from Example 1 in dry dichloromethane (0.34 ml) was added at 0° C. triethylamine (dried over potassium hydroxide) (14 µl, 0.10 mmol) and 2,4,6-trichlorobenzoyl chloride (15.5 µl, 0.10 mmol) over a period of 10 minutes. After stirring at ambient temperature for 2.5 hours a solution of 4-dimethylaminopyridine (49 mg, 0.40 mmol) in dry dichloromethane (0.3 ml) and methylamine hydrochloride (13.5 mg, 0.20 mmol) were added. After stirring at ambient temperature for 15 hours, the reaction mixture was diluted with dichloromethane (5 ml). The resulting organic layer was successively washed with water (5 ml), with saturated sodium hydrogen carbonate solution (5 ml). The resulting aqueous layer was extracted with dichloromethane (10 ml), then the combined organic layers after drying over magnesium sulfate were evaporated to dryness. The resulting crude product was purified by column chromatography (silica 15–40 µm (2 g), dichloromethane then dichloromethane/methanol, 98:2) to provide the expected compound (47 mg, 89%). The product thus obtained showed the following characteristics:

$^1$H NMR 400 MHz (CDCl$_3$) (δ ppm, J Hz): 6.61 (1H, s, H-14*), 6.59 (1H, s, H-17*), 6.48 (1H, m, NH), 5.85 (3H, m, OCH$_2$O+H-3), 5.03 (1H, s, H-1), 3.79 (1H, d, J$_{4-3}$=9.7, H-4), 3.67 (3H, s, OCH$_3$), 3.17 (1H, m, H-11β), 3.09 (1H, m, H-8α), 2.93 (1H, m, H-10α), 2.74 (3H, d, J=4.9, NHC$\underline{H}_3$), 2.59 (2H, m, H-8β+H-10β), 2.37 (1H, dd, J$_{AB}$=14.2, J=7.0, H-11α), 2.11 and 1.84 (2H, 2d, J$_{AB}$=14.5, C$\underline{H}_2$CON), 2.02 (1H, m, H-6$_A$), 1.89 (2H, m, H-6$_B$+CH), 1.75 (2H, m, CH$_2$-7), 1.4–1.1 (5H, m, CH+2×CH$_2$), 1.18 (3H, s, CH$_3$), 0.96 (3H, s, CH$_3$).

EXAMPLE 17

Preparation of (−)-Cephalotaxyl(2'S)-2-(dimethylamino)carbonylmethyl-6,6-dimethyl-2-tetrahydropyranecarboxylate or 4'-Dimethylamino-4'-demethoxy-anhydro-epi-homoharringtonine

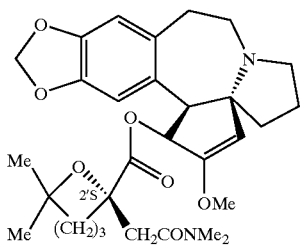

To a stirred mixture of 4'-demethyl-anhydro-epi-homoharringtonine (60 mg, 0.117 mmol) resulting from Example 1 in dry dichloromethane (0.4 ml) was added at 0° C. triethylamine (dried over potassium hydroxide) (16.2 µl, 0.111 mmol) and 2,4,6-trichlorobenzoyl chloride (18 µl, 0.117 mmol) over a period of 10 minutes. After stirring at ambient temperature for 2.5 hours a solution of 4-dimethylaminopyridine (28.6 mg, 0.234 mmol) in dry dichloromethane (0.16 ml) and dimethylamine (in excess) were added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 µm (1.5 g), dichloromethane then dichloromethane/methanol, 99:1 to 98:2) to provide the expected compound (11 mg, 17.4%). The product thus obtained showed the following characteristics:

$^1$H NMR 400 MHz (CDCl$_3$) (δ ppm, J Hz): 6.59 (2H, s, H-17+H-14), 5.88 (1H, d, J3–4=9.7, H-3), 5.84 (2H, s, OCH$_2$O), 5.01 (1H, s, H-1), 3.80 (1H, d, J$_{4-3}$=9.9, H-4), 3.66 (3H, s, OCH$_3$), 3.23 (1H, m, H-11β), 3.09 (1H, m, H-8α), 2.95 (1H, m, H-10α) and (3H, s, NCH$_3$), 2.88 (3H, s, NCH$_3$), 2.60 (2H, m, H-8□+H-10β), 2.37 (1H, m, H-11α), 2.35 and 1.73 (2H, 2d, J$_{AB}$=13.5, C$\underline{H}_2$CON), 2.01 (2H, m, CH$_2$-6), 1.95–1.10 (8H, m, CH2-7+3×CH$_2$), 1.08 (3H, s, CH$_3$), 0.96 (3H, s, CH$_3$).

EXAMPLE 18

Preparation of (−)-Cephalotaxyl(2'S)-2-(diethylamino)carbonylmethyl-6,6-dimethyl-2-tetrahydropyranecarboxylate or 4-Diethylamino-4-demethoxy-anhydro-epi-homoharringtonine

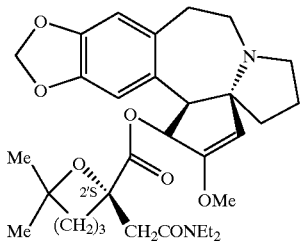

To a stirred mixture of 4'-demethyl-anhydro-epi-homoharringtonine (57 mg, 0.11 mmol) resulting from Example 1 in dry dichloromethane (0.34 ml) was added at 0° C. triethylamine (dried over potassium hydroxide) (15.3 μl, 0.11 mmol) and 2,4,6-trichlorobenzoyl chloride (17.1 μl, 0.11 mmol) over a period of 10 minutes. After stirring at ambient temperature for 2.5 hours a solution of 4-dimethylaminopyridine (27.4 mg, 0.22 mmol) and diethylamine (23 μl, 0.22 mmol) in dry dichloromethane (0.16 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness.

The resulting crude product was purified by column chromatography (silica 15–40 μm (1.5 g), dichmoromethane then dichloromethane/methanol, 99:1 to 98:2) to provide the expected compound (50 mg, 80%). The product thus obtained showed the following characteristics:

$^1$H NMR 400 MHz (CDCl$_3$) (δ ppm, J Hz): 6.60 (1H, s, H-14*), 6.58 (1H, s, H-17*), 5.84 (3H, m, OCH$_2$O+H-3), 5.02 (1H, s, H-1), 3.81 (1H, d, J$_{4-3}$=9.6, H-4), 3.69 (2H, m, NC$\underline{H}_2$CH$_3$), 3.66 (3H, s, OCH$_3$), 3.21 (1H, m, H-11β), 3.08 (1H, m, H-8α), 2.95 (3H, m, H-10α+NC$\underline{H}_2$CH$_3$), 2.60 (2H, m, H-8β+H-10β), 2.41 and 1.71 (2H, 2d, J$_{AB}$=13.3, C$\underline{H}_2$COn), 2.37 (1H, dd, J$_{AB}$=14.2, J=7.0, H-11α), 2.01 (1H, m, H-6$_A$), 2.0–1.0 (6H, m, 3×CH$_2$), 1.89 (1H, m, H-6$_B$), 1.75 (2H, m, CH$_2$-7), 1.10 (9H, m, N(CH$_2$C$\underline{H}_3$)$_2$+CH$_3$), 0.92 (3H, s, CH$_3$).

EXAMPLE 19

Preparation of (−)-Cephalotaxyl(2'R)-2-(diethylamino)carbonylmethyl-6,6-dimethyl-2-tetrahydropyranecarboxylate or 4'-Diethylamino-4'-demethoxy-anhydro-homoharringtonine

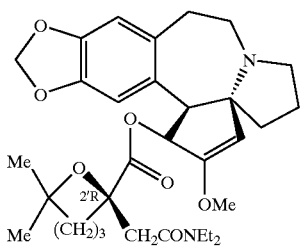

To a stirred mixture of 4'-demethyl-anhydro-homoharringtonine (250 mg, 0.487 mmol) resulting from Example 2 in dry dichloromethane (1.8 ml) was added at 0° C. triethylamine (dried over potassium hydroxide) (65 μl, 1, 0.487 mmol) and 2,4,6-trichlorobenzoyl chloride (76 μl, 0.487 mmol) over a period of 10 minutes. After stirring at ambient temperature for 2.5 hours a solution of 4-dimethylaminopyridine (119 mg, 0.974 mmol) and diethylamine (105 μl, 0.974 mmol) in dry dichloromethane (0.8 ml) was added. After stirring at ambient temperature for 15 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 □m (8 g), dichloromethane then dichloromethane/methanol, 99:1 to 97:3) to provide the expected compound (226 mg, 82%). The product thus obtained showed the following characteristics:

$^1$H NMR 400 MHz (CDCl$_3$) (δ ppm, J Hz): 6.63 (1H, s, H-14*), 6.59 (1H, s, H-17*), 5.86 (1H, d, J$_{3-4}$=9.6, H-3), 5.82 and 5.78 (2H, 2s, OCH$_2$O), 5.04 (1H, s, H-1), 3.81 and 3.72 (2H, 2m, NC$\underline{H}_2$CH$_3$), 3.80 (1H, d, H-4), 3.70 (3H, s, OCH$_3$), 3.12 (2H, m, H-11β+H-8α), 2.90 (3H, m, H-10α+NC$\underline{H}_2$CH$_3$), 2.59 (2H, m, H-8β+H-10β), 2.38 (1H, dd, J$_{AB}$=14.2, J=6.7, H-11α), 2.24 (1H, d, J$_{AB}$=13.1, C$\underline{H}_A$CON), 2.02 (1H, m, H-6$_A$), 1.95–1.15 (10H, m, H-6$_B$+CH$_2$-7+ C$\underline{H}_B$CON+3×CH$_2$), 1.06 and 1.03 (6H, 2t, J=7.1, N(CH$_2$C$\underline{H}_3$)$_2$), 1.04 (3H, s, CH$_3$), 0.92 (3H, s, CH$_3$).

EXAMPLE 20

Preparation of (−)-Cephalotaxyl(2'S)-2-(but-2-enyl)oxycarbonylmethyl-6,6-dimethyl-2-tetrahydropyranecarboxylate or 4'-(but-2-Enyl)-4'-demethyl-anhydro-epi-homoharringtonine

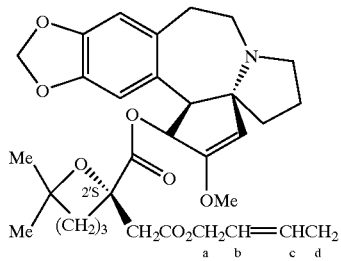

1.) Method A

To a stirred mixture of 4'-demethyl-anhydro-epi-homoharringtonine (60 mg, 0.12 mmol) resulting from Example 1 in dry dichloromethane (0.35 ml) was added at 0° C. triethylamine (dried over potassium hydroxide) (17 μl, 0.12 mmol) and 2,4,6-trichlorobenzoyl chloride (19 μl, 0.12 mmol) over a period of 10 minutes. After stirring at ambient temperature for 2.5 hours a solution of 4-dimethylaminopyridine (29 mg, 0.14 mmol) and crotyl alcohol (17 μl, 0.24 mmol) in dry dichloromethane (0.19 ml) was added. After stirring at ambient temperature for 72 hours, the reaction mixture was diluted with dichloromethane (5 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by, column chromatography (silica 15–40 μm (1 g), dichloromethane then dichloromethane/methanol, 99:1 to 97:3) to provide the expected compound (36 mg, 55%). The product thus obtained showed the following characteristics:

$^1$H NMR 400 MHz (CDCl3) (δ ppm, J Hz): 6.61 (1H, s, H-17*), 6.57 (1H, s, H-14*), 5.85 and 5.81 (2H, 2d, $J_{AB}$=1.4, OCH$_2$O), 5.83 (1H, d, $J_{3-2}$=9.6, H-3), 5.75 (1H, dq, $J_{c-b'}$=15.2, $J_{c-d'}$=6.5, H-c), 5.55 (1H, m, $J_{b-c}$=15.3, H-b), 5.02 (1H, s, H-1), 4.46 and 4.38 (2H, 2dd, $J_{AB}$=12.3, $J_{a-b'}$=6.5, CH$_2$-a), 3.77 (1H, d, $J_{4-3}$=9.7, H-4), 3.65 (3H, s, OCH$_3$), 3.23 (1H, m, H-11β), 3.09 (1H, m, H-8α), 2.95 (1H, m, H-10α), 2.61 (2H, m, H-8β+H-10β), 2.40 (1H, dd, $J_{AB}$=14.2, J=6.6, H-11α), 2.13 and 1.78 (2H, 2d, $J_{AB}$=14.3, $\underline{CH_2}$CO$_2$), 2.01 (1H, m, H-6$_A$), 1.90 (1H, m, H-6$_B$), 1.76 (2H, m, CH$_2$-7), 1.71 (3H, dd, $J_{d-c}$=6.5, $J_{d-b}$=1.1, CH$_3$d), 1.55–1.2 (6H, m, 3×CH$_2$), 1.11 (3H, s, CH$_3$), 1.01 (3H, s, CH$_3$).

2.) Method B

Sodium hydride 60% (10 mg, 0.228 mmol) was added to a solution of anhydro-epi-homoharringtonine (100 mg, 0.18 mmol) resulting from Example 1 in crotyl alcohol (1 ml) and the resulting mixture was stirred at ambient temperature for 72 hours. After neutralization by addition of hydrochloric acid 1N, dilution with water (5 ml) and saturation with sodium chloride, the resulting aqueous layer was extracted with dichloromethane (3×5 ml). The combined organic layers were dried over magnesium sulfate and evaporated to dryness. The resulting crude product was purified by column chromatography (silica 15–40 μm (2 g), dichloromethane then dichloromethane/methanol, 99:1) to provide the expected product (66 mg, 62%). The product thus obtained showed identical characteristics to this obtained with method A.

EXAMPLE 21

Preparation of (−)-Cephalotaxyl(2'R)-2-(but-2-enyl) oxycarbonylmethyl-6,6-dimethyl-2-tetrahydropyranecarboxylate or 4'-(but-2-Enyl)-4'-demethyl-anhydro-homoharringtonine

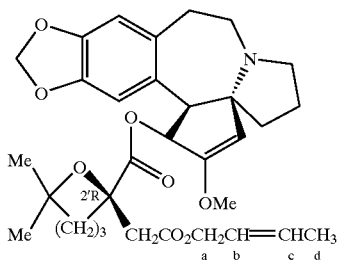

Sodium hydride 60% (21.9 mg, 0.9 mmol) was added to a solution of anhydro-homoharringtonine (400 mg, 0.767 mmol) in 3-methyl-2-butenol (4 ml) and the resulting mixture was stirred at ambient temperature for 36 hours under argon. After dilution with water (50 ml) the aqueous layer was extracted with dichloromethane (3×20 ml). The combined organic layers were diluted with dichloromethane (150 ml), washed with water (50 ml), dried over magnesium sulfate and evaporated to dryness (350 mg crude, 81%). The crude product thus obtained was purified by column chromatography (silica 15–40 μm (5 g), dichloromethane then dichloromethane/methanol, 95:5) to provide the expected product (105 mg, 24.5%). The product thus obtained showed the following characteristics:

$^1$H NMR 400 MHz (CDCl$_3$) (δ ppm, J Hz): 6.61 (1H, s, H-17*), 6.57 (1H, s, H-14*), 5.91 (1H, d, $J_{3-2}$=9.4, H-3), 5.86 and 5.78 (2H, 2d, JAB=1.4, OCH$_2$O), 5.72 (1H, m, H-c), 5.55 (1H, m, H-b), 5.03 (1H, s, H-1), 4.43 (2H, m, CH$_2$-a), 3.78 (1H, d, $J_{4-3}$=9.7, H-4), 3.69 (3H, s, OCH$_3$), 3.11 (2H, m, H-11β+H-8α), 2.94 (1H, m, H-10α), 2.59 (2H, m, H-8β+H-10β), 2.36 (1H, dd, $J_{AB}$=14.1, J=6.9, H-11α), 2.13 and 1.60 (2H, 2d, $J_{AB}$=14.43, $\underline{CH_2}$CO$_2$), 2.0 (1H, m, H-6$_A$), 1.89 (1H, m, H-6$_B$), 1.75 (2H, m, CH$_2$-7), 1.71 (3H, dd, $J_{d-c}$=5.5, $J_{d-b}$=1.1, CH$_3$-d), 1.7–1.2 (6H, m, 3×CH$_2$), 1.10 (3H, s, CH$_3$), 1.04 (3H, s, CH$_3$).

EXAMPLE 22

Preparation of 4'-Demethyl-epi-homoharringtonine from Epi-homoharringtonine

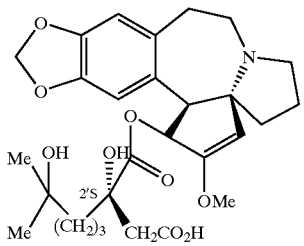

To a stirred solution of epi-homoharringtonine (266 mg, 0.488 mmol) in methanol (6.7 ml) was added lithium hydroxide (119 mg, 0.488 mmol) and water (2.2 ml). After stirring 5 hours at ambient temperature 1N hydrochloric acid was added to pH 7 and ethanol was evaporated under reduced pressure. After addition of dichloromethane (10 ml), the residual aqueous layer is exhausted by trituration with magnesium sulfate. The solid removed by filtration was washed with dichloromethane (4×2 ml) and the combined organic layers were dried over magnesium sulfate and evaporated to dryness to provide the expected compound (128 mg crude, 49%). The crude product thus obtained showed the following characteristics:

$^1$H NMR 400 MHz (DMSO-d$_6$) (δ ppm, J Hz) 6.64 (1H, s, H17*), 6.57 (1H, s, H14*), 5.90 (2H, s, OCH$_2$O), 5.75 (1H, d, $J_{3-4}$=9.5, H-3), 5.11 (1H, s, H-1), 3.95 (1H, s, 2'-OH), 3.78 (1H, d, $J_{4-3}$=9.7, H-4), 3.58 (3H, s, OCH$_3$), 3.06 (1H, m, H-11β), 2.81 (1H, m, H-8α), 2.68 (1H, m, H-10α), 2.52 (2H, m, H-8β+H-10β), 2.33 (1H, dd, $J_{AB}$=13.4, J=6.3, H-11α), 2.0 (2H, m, $\underline{CH_2}$CO$_2$), 1.9–0.6 (10H, m, CH$_2$-6+CH$_2$-7+3×CH$_2$), 0.99 (3H, s, CH$_3$), 0.97 (3H, s, CH$_3$).

EXAMPLE 23

Preparation of 4'-Demethyl-homoharringtonine from Homoharringtonine

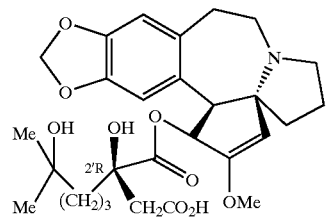

To a stirred solution of homoharringtonine (60 mg, 0.11 mmol) in methanol (1.5 ml) was added lithium hydroxide (27 mg, 1.1 mmol) and water (0.5 ml). After stirring 15 hours at ambient temperature 1N hydrochloric acid was added to pH 7–8 and ethanol was evaporated under reduced pressure. After addition of dichloromethane (5 ml), the residual aqueous layer is exhausted by trituration with magnesium sulfate. The solid removed by filtration was washed with dichloromethane (4×2 ml) and the combined organic layers were dried over magnesium sulfate and evaporated to dryness to provide the expected compound (28 mg crude, 48%). The crude product thus obtained showed the following characteristics:

IR (film) (cm$^{-1}$): 3600–2800 (CO$_2$H, OH), 1738 (CO$_2$), 1657 (C=C—O), 1505 (Ar), 1223 (C—O), 1166 (C—O), 1080 (C—O), 1041 (C—O), 912. $^1$H NMR 400 MHz (DMSO-d$_6$) (δ ppm, J Hz): 6.63 (1H, s, H-17*), 6.54 (1H, s, H-14*), 5.89+5.86 (2H, 2s, OCH$_2$O), 5.70 (1H, d, J$_{3-4}$= 9.6, H-3), 5.13 (1H, s, H-1), 4.02 (1H, s, 2'-OH), 3.77 (1H, d, J$_{4-3}$=9.6, H-4), 3.59 (3H, s, OCH$_3$), 3.04 (1H, m, H-11β), 2.81 (1H, td, J=8.7 and 3.6), H-8α), 2.69 (1H, m, H-10α), 2.52 (2H, m, H-8β+H-10β), 2.33 (1H, dd, J$_{AB}$=14.0, J=7.0, H-11α), 1.86 (1H, m, H-6$_A$), 1.81 (1H, m, H-6$_B$), 1.68+1.57 (4H, 2m, CH$_2$-7+C$\underline{H}_2$CO$_2$), 1.16 (6H, m, 3×CH$_2$), 1.02 (3H, s, CH$_3$), 1.01 (3H, s, CH$_3$).

EXAMPLE 24

Preparation of (2'S)-4'-Ethyl-4'-demethyl-epi-homoharringtonine

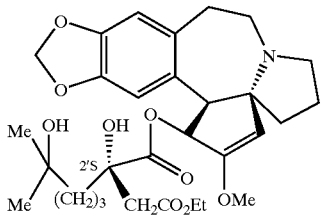

1.) Method A

To a stirred solution of 4'-ethyl-4'-demethyl-anhydro-epi-homoharringtonine (59 mg, 0.109 mmol) resulting from Example 3 in dry dichloromethane (0.3 ml) under nitrogen was added at −10° C. a commercial solution of hydrobromic acid in acetic acid (0.195 ml, 0.98 mmol, HBr 30% w/w). After stirring at −10° C. for 3 hours, was added water (2.8 ml) and the temperature was raised to 20° C. After stirring at 20° C. for 3 hours, was added a sodium carbonate solution (0.76 M, 6 ml) up to pH 8. The resulting aqueous layer, after saturation with sodium chloride, was extracted with dichloromethane (3×10 ml) and the combined organic layers were dried over magnesium sulfate and evaporated to dryness to provide the expected compound (46 mg crude, 76%). The crude product thus obtained showed the following characteristics:

$^1$H NMR 400 MHz (CDCl$_3$) (δ ppm, J Hz): 6.64 (1H, s, H-17*), 6.59 (1H, s, H-14*), 5.95 and 5.85 (2H, 2d, J$_{AB}$=1.3, OCH$_2$O), 5.94 (1H, d, J$_{3-4}$=9.3, H-3), 5.03 (1H, s, H-1), 4.11 (2H, m, OC$\underline{H}_2$CH$_3$), 3.78 (1H, d, J$_{4-3}$=9.8, H-4), 3.65 (3H, s, OCH$_3$), 3.52 (1H, s, 2'-OH), 3.09 (2H, m, H-11β+H-8α), 2.93 (1H, m, H-10α), 2.59 and 2.51 (2H, 2d, J$_{AB}$=16.6, CH$_2$CO$_2$), 2.57 (2H, m, H-8β+H-10β), 2.38 (1H, dd, J$_{AB}$= 14.2, J=6.8, H-11α), 2.02 (1H, m, H-6$_A$), 1.89 (1H, m, H-6$_B$), 1.71 (2H, m, CH$_2$-7), 1.5–0.6 (6H, m, 3×CH$_2$), 1.24 (3H, t, J=7.2, OCH$_2$CH$_3$), 1.16 (3H, s, C$\underline{H}_3$), 1.15 (3H, s, CH$_3$).

2.) Method B

To a stirred mixture of 4'-demethyl-epi-homoharringtonine (40 mg, 0.075 mmol) resulting from Example 22 in dry dichloromethane (0.26 ml) was added at 0° C. triethylamine (dried over potassium hydroxide) (10 μl, 0.075 mmol) and 2,4,6-trichlorobenzoyl chloride (12 μl, 0.075 mmol) over a period of 10 minutes. After stirring at ambient temperature for 2.5 hours a solution of 4-dimethylaminopyridine (18.4 mg, 0.15 mmol) and ethanol (8 μl, 0, 138 mmol) in dry dichloromethane (0.16 ml) was added. After stirring at ambient temperature for 15 hours, the reaction mixture was diluted with dichloromethane (10 ml). The resulting organic layer was successively washed with water (5 ml), with saturated sodium hydrogen carbonate solution (5 ml), with brine (5 ml). The resulting aqueous layer was extracted with dichloromethane (10 ml), then the combined organic layers after drying over magnesium sulfate were evaporated to dryness. The resulting crude product was purified by column chromatography (silica 15–40 □m (1 g), dichloromethane then dichloromethane/methanol, 99:1 to 98:2) to provide the expected compound (11 mg, 26%). The product thus obtained showed identical characteristics to this obtained with method A.

EXAMPLE 25

Preparation of (2'R)-4'-Ethyl-4'-demethyl-homoharringtonine

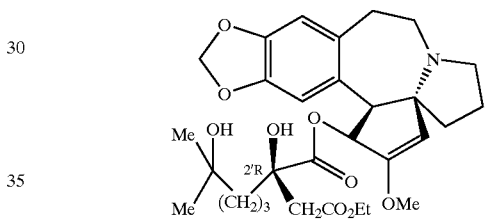

1.) Method A

To a stirred solution of 4'-ethyl-4'-demethyl-anhydro-homoharringtonine (220 mg, 0.406 mmol) resulting from Example 4 in dry dichloromethane (1.1 ml) under nitrogen was added at −10° C. a commercial solution of hydrobromic acid in acetic acid (0.728 ml, 3.6 mmol, HBr 30% w/w). After stirring at −10° C. for 3 hours, was added water (10 ml) and the temperature was raised to 20° C. After stirring at 20° C. for 3 hours, was added a sodium carbonate solution (0.76 M, 31.5 ml) up to pH 8–9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15–40 μm (8 g), dichloromethane then dichloromethane/methanol, 99:1 to 98:2) to provide the expected compound (125 mg, 55%). The product thus obtained showed the following characteristics:

HRMS calcd for C$_{30}$H$_{42}$NO$_9$ [M+H]$^+$ 560.2860, obsd 560.2863; IR (film) (cm$^{-1}$): 3516 (OH), 3427 (OH), 1741 (CO$_2$), 1656 (C=C—O), 1504 (Ar), 1224 (C—O), 1183 (C—O), 1114 (C—O), 1083 (C—O), 1035 (C—O), 911. $^1$H NMR 400 MHz (CDCl$_3$) (δ ppm, J Hz): 6.62 (1H, s, H-17*), 6.55 (1H, s, H-14*), 5.98 (1H, d, J$_{3-4}$=9.7, H-3), 5.86 (2H, m, OCH$_2$O), 5.05 (1H, s, H-1), 4.02 (2H, m, OC$\underline{H}_2$CH$_3$), 3.78 (1H, d, J$_{4-3}$=9.7, H-4), 3.68 (3H, s, OCH$_3$), 3.53 (1H, s, 2'-OH), 3.10 (2H, m, H-11β+H-8α), 2.96 (1H, m, H-10α), 2.60 (2H, m, H-8β+H-10β), 2.38 (1H, m, H-11α), 2.24 and 1.90 (2H, 2d, J$_{AB}$=16.2, C$\underline{H}_2$CO$_2$), 2.02 (1H, m, H-6$_A$), 1.90

(1H, m, H-6$_B$), 1.76 (2H, m, CH$_2$-7), 1.5–1.15 (6H, m, 3×CH$_2$), 1.21 (3H, t, J=7.2, OCH$_2$C$\underline{H}_3$), 1.19 (6H, 2s, 2×CH$_3$).

2.) Method B

Sodium hydride 60% (2.4 mg, 0.1 mmol) was added to a solution of homoharringtonine (300 mg, 0.55 mmol) in dry ethanol (30 ml) and the resulting mixture was stirred at ambient temperature for 27 hours. After addition of water (10 ml) the resulting aqueous layer was saturated with sodium chloride and extracted with dichloromethane (3×20 ml). The combined organic layers were dried over magnesium sulfate and evaporated to dryness. The crude product thus obtained was purified by phase-reversed chromatography (octadecylsilane 12 μm (65 g), buffer NH$_4$Cl—HCl/ methanol, 82:18). After removal of methanol in vacuo the resulting aqueous layer was alkalinized to pH 8–9 and extracted with dichloromethane (3×50 ml). The combined organic layers were dried over magnesium sulfate and evaporated to dryness to provide the expected compound (298 mg; 97%). The product thus obtained showed identical characteristics to this obtained with method A.

EXAMPLE 26

Preparation of (2'S)-4'-Isopropyl-4'-demethyl-epi-homoharringtonine

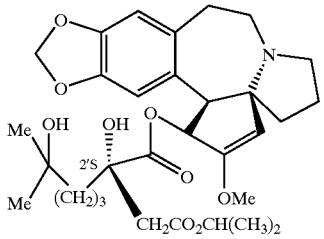

To a stirred solution of 4'-isopropyl-4'-demethyl-anhydro-epi-homoharringtonine (46 mg, 0.083 mmol) resulting from Example 5 in dry dichloromethane (0.23 ml) under nitrogen was added at –10° C. a commercial solution of hydrobromic acid in acetic acid (0.148 ml, 0.745 mmol, HBr 30% w/w). After stirring at –10° C. for 3 hours, was added water (2.2 ml) and the temperature was raised to 20° C. After stirring at 20° C. for 3 hours, was added a sodium carbonate solution (0.76 M, 4 ml) up to pH 8. The resulting aqueous layer, after saturation with sodium chloride, was extracted with dichloromethane (3×5 ml) and the combined organic layers were dried over magnesium sulfate and evaporated to dryness to provide the expected compound (30 mg crude, 64%). The crude product thus obtained showed the following characteristics:

$^1$H NMR 400 MHz (CDCl$_3$) (δ ppm, J Hz): 6.64 (1H, s, H-17*), 6.59 (1H, s, H-14*), 5.94 and 5.85 (2H, 2d, J$_{AB}$=1.3, OCH$_2$O), 5.93 (1H, d, J$_{3-4}$=9.8, H-3), 5.03 (1H, s, H-1), 4.98 (1H, m, J=6.2, OC$\underline{H}$(CH$_3$)$_2$), 3.78 (1H, d, J$_{4-3}$=9.7, H-4), 3.65 (3H, s, OCH$_3$), 3.54 (1H, s, 2'-OH), 3.09 (2H, m, H-11β+H-8α), 2.94 (1H, m, H-10α), 2.57 and 2.49 (2H, 2d, J$_{AB}$=16.6, C$\underline{H}_2$CO$_2$), 2.56 (2H, m, H-8β+H-10β), 2.38 (1H, dd, J$_{AB}$=14.0, J=7.0, H-11α), 2.02 (1H, m, H-6$_A$), 1.89 (1H, m, H-6$_B$), 1.71 (2H, m, CH$_2$-7), 1.5–0.6 (6H, m, 3×CH$_2$), 1.22 and 1.21 (6H, 2d, J=6.2, OCH(C$\underline{H}_3$)$_2$), 1.16 (3H, s, CH$_3$), 1.15 (3H, s, CH$_3$).

EXAMPLE 27

Preparation of (2'R)-4'-Isopropyl-4'-demethyl-homoharringtonine

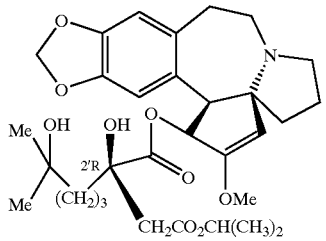

1.) Method A

To a stirred solution of 4'-isopropyl-4'-demethyl-anhydro-homoharringtonine (220 mg, 0.36 mmol) resulting from Example 6 in dry dichloromethane (1 ml) under nitrogen was added at –10° C. a commercial solution of hydrobromic acid in acetic acid (0.64 ml, 3.24 mmol, HBr 30% w/w). After stirring at –10° C. for 3 hours, was added water (9.5 ml) and the temperature was raised to 20° C. After stirring at 20° C. for 3 hours, was added a sodium carbonate solution (0.76 M, 17.4 ml) up to pH 8–9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15–40 μm (6 g), dichloromethane then dichloromethane/methanol, 99:1 to 97:3) to provide the expected compound (103 mg, 50%). The product thus obtained showed the following characteristics:

HRMS calcd for C$_{31}$H$_{44}$NO$_9$ [M+H]$^+$ 574.3016, obsd 574.3012; IR (film) (cm$^{-1}$): 3519 (OH), 3430 (OH), 1735 (CO$_2$), 1655 (C=C—O), 1504 (Ar), 1224 (C—O), 1182 (C—O), 1109 (C—O), 1039 (C—O), 910. $^1$H NMR 400 MHz (CDCl$_3$) (δ ppm, J Hz): 6.63 (1H, s, H-17*), 6.56 (1H, s, H-14*), 5.96 (1H, d, J$_{3-4}$=9.8, H-3), 5.86 (2H, s, OCH$_2$O), 5.05 (1H, s, H-1), 4.88 (1H, m, J=6.2, OC$\underline{H}$(CH$_3$)$_2$), 3.78 (1H, d, J$_{4-3}$=9.8, H-4), 3.68 (3H, s, OCH$_3$), 3.54 (1H, s, 2'-OH), 3.10 (2H, m, H-11β+H-8α), 2.95 (1H, m, H-10α), 2.60 (2H, m, H-8β+H-10β), 2.38 (1H, dd, J$_{AB}$=14.0, J=6.7, H-11α), 2.19 and 1.87 (2H, 2d, J$_{AB}$=16.0, C$\underline{H}_2$CO$_2$), 2.02 (1H, m, H-6$_A$), 1.91 H, m, H-6$_B$), 1.76 (2H, m, CH$_{2-7}$), 1.5–1.16 (6H, m, 3×CH$_2$), 1.18 (12H, m, CH(C$\underline{H}_3$)2+2×CH$_3$).

2.) Method B

Sodium hydride 60% (13 mg, 0.325 mmol) was added (in 2 parts, at t=0 and t=16 hours) to a solution of homoharringtonine (440 mg, 0.807 mmol) in isopropanol (6 ml) with stirring at ambient temperature under argon. 4 hours after the last addition the mixture was adjusted to pH 1.9 by addition of hydrochloric acid 0.1N (157 ml) and the aqueous layer was washed with ether (3×8 ml). The resulting aqueous layer was alkalinized with ammonia 25% (0.3 ml) and was extracted with dichloromethane (8×8 ml). The combined organic layers were dried over magnesium sulfate and evaporated to dryness (311 mg crude, 67%). The crude product thus obtained was purified by phase-reversed chromatography (octadecylsilane 12 μm (100 g), buffer pH3/ methanol, 61:39). After removal of methanol in vacuo the resulting aqueous layer was alkalinized to pH 10 with ammonia 25% and extracted with dichloromethane (6×8 ml). The combined organic layers were dried over magnesium sulfate and evaporated to dryness to provide the expected compound (143 mg; 31%). The product thus obtained showed identical characteristics to this obtained with method A.

EXAMPLE 28

Preparation of (2'S)-4'-Benzyl-4'-demethyl-epi-homoharringtonine

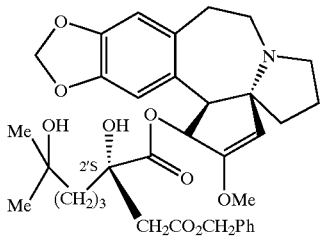

To a stirred solution of 4'-benzyl-4'-demethyl-anhydro-epi-homoharringtonine (28 mg, 0.046 mmol) resulting from Example 7 in dry dichloromethane (0.14 ml) under nitrogen was added at −10° C. a commercial solution of hydrobromic acid in acetic acid (83 μl, 0.417 mmol, HBr 30% w/w). After stirring at −10° C. for 3 hours, was added water (2 ml) and the temperature was raised to 20° C. After stirring at 20° C. for 3 hours, was added a sodium carbonate solution (0.76 M, 4 ml) up to pH 8. The resulting aqueous layer, after saturation with sodium chloride, was extracted with dichloromethane (3×3 ml) and the combined organic layers were dried over magnesium sulfate and evaporated to dryness to provide the expected compound (30 mg crude, 100%). The crude product thus obtained showed the following characteristics:

$^1$H NMR 400 MHz (CDCl$_3$) (δ ppm, J Hz): 7.34 (5H, m, Ph), 6.64 (1H, s, H-17), 6.60 (1H, s, H-14), 5.90 (3H, m, OCH$_2$O+H-3), 5.12 and 5.07 (2H, 2d, J$_{AB}$=12.4, OCH$_2$Ph), 5.01 (1H, s, H-1), 3.78 (1H, d, H-4), 3.60 (3H, s, OCH$_3$), 3.13 (2H, m, H-11β+H-8α), 2.96 (1H, m, H-10α), 2.66 and 2.57 (2H, 2d, J$_{AB}$=16.7, CH$_2$CO$_2$), 2.60 (2H, m, H-8β+H-10β), 2.40 (1H, m, H-11α), 2.04 (1H, m, H-6$_A$), 1.92 (1H, m, H-6$_B$), 1.78 (2H, m, CH$_2$-7), 1.6–0.8 (6H, m, 3×CH$_2$), 1.16 (3H, s, CH$_3$), 1.15 (3H, s, CH$_3$).

EXAMPLE 29

Preparation of (2'R)-4'-Benzyl-4'-demethyl-homoharringtonine

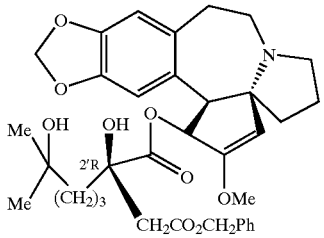

1.) Method A

To a stirred solution of 4'-benzyl-4'-demethyl-anhydro-homoharringtonine (261 mg, 0.432 mmol) resulting from Example 8 in dry dichloromethane (1.3 ml) under nitrogen was added at −10° C. a commercial solution of hydrobromic acid in acetic acid (0.775 ml, 3.89 mmol, HBr 30% w/w). After stirring at −10° C. for 3 hours, was added water (18.6 ml) and the temperature was raised to 20° C. After stirring at 20° C. for 3 hours, was added a sodium carbonate solution (0.76 M, 37 ml) up to pH 8. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15–40 μm (8 g), dichloromethane then dichloromethane/methanol, 99:1 to 95:5) to provide the expected compound (80 mg, 30%). The crude product thus obtained showed the following characteristics:

IR (film) (cm$^{-1}$): 3520 (OH), 3401 (OH), 1744 (CO2), 1655 (C=C—O), 1504 (Ar), 1224 (C—O), 1173 (C—O), 1082 (C—O), 1037 (C—O), 910. $^1$H NMR 400 MHz (CDCl$_3$) (δ ppm, J Hz): 7.33 (5H, m, Ph), 6.62 (1H, s, H-17), 6.44 (1H, s, H-14), 5.96 (1H, d, J$_{3-4}$=9.7, H-3), 5.77 and 5.65 (2H, 2s, OCH$_2$O), 5.09 and 4.94 (2H, 2d, J$_{AB}$=12.4, OCH$_2$Ph), 5.05 (1H, s, H-1), 3.70 (1H, d, J$_{4-3}$=10, H-4), 3.68 (3H, s, OCH$_3$), 3.52 (1H, s, 2'-OH), 3.10 (2H, m, H-11β+H-8α), 2.93 (1H, m, H-10α), 2.59 (2H, m, H-8β+H-10β), 2.40 (1H, dd, J$_{AB}$=14, J=6.7, H-11α), 2.31 and 1.92 (2H, 2d, J$_{AB}$=16.3, CH$_2$CO$_2$), 2.0 (1H, m, H-6$_A$), 1.90 (1H, m, H-6$_B$), 1.75 (2H, m, CH$_2$-7), 1.6–11 (6H, m, 3×CH$_2$), 1.25 (1H, s, OH), 1.19 (3H, s, CH$_3$), 1.18 (3H, s, CH$_3$).

2.) Method B

Sodium hydride 60% (10 mg, 0.275 mmol) was added to a solution of homoharringtonine (300 mg, 0.55 mmol) in benzylic alcool (4 ml) and the resulting mixture was stirred at ambient temperature for 1.5 hours under argon. After adjusting to pH 2.5 by addition of hydrochloric acid 0.1N (15 ml) the aqueous layer was washed with ether (3×15 ml). The resulting aqueous layer was alkalinized with ammonia 25% (1.5 ml) and was extracted with dichloromethane (6×15 ml). The combined organic layers were dried over magnesium sulfate and evaporated to dryness. The crude product thus obtained was purified by phase-reversed chromatography (octadecylsilane 12 μm (100 g), buffer pH 3/methanol, 47:53). After removal of methanol in vacuo the resulting aqueous layer was alkalinized to pH 9 with ammonia 25% and extracted with dichloromethane (3×5 ml). The combined organic layers were dried over magnesium sulfate and evaporated to dryness to provide the expected compound (154 mg, 45%). The product thus obtained showed the following characteristics.

EXAMPLE 30

Preparation of (2'R)-4-Methylthio-4'-demethoxy-homoharringtonine

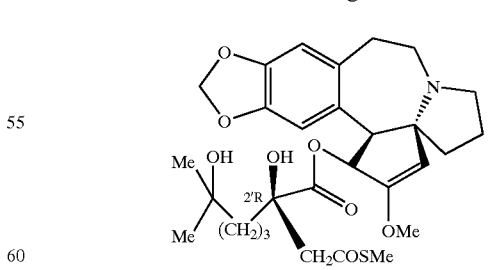

To a stirred solution of 4'-methylthio-4'-demethoxy-anhydro-homoharringtonine (209 mg, 0.384 mmol) resulting from Example 9 in dry dichloromethane (1 ml) under nitrogen was added at −10° C. a commercial solution of hydrobromic acid in acetic acid (0.608 ml, 3.46 mmol, HBr 30% w/w). After stirring at −10° C. for 3 hours, was added water (12.2 ml) and the temperature was raised to 20° C. After stirring at 20° C. for 3 hours, was added a sodium carbonate solution (0.76 M, 29 ml) up to pH 8–9. The resulting aqueous layer, after saturation with sodium chloride, was extracted with dichloromethane (3×20 ml) and the combined organic layers were dried over magnesium sulfate and evaporated to dryness. The resulting crude product was purified by reversed-phase column chromatography (n-octadecylsilane, 15 μm (20 g), methanol/buffer pH 3, 32:68) and the retained fractions were combined. After removal of methanol in vacuo the residual aqueous layer (250 ml) was adjusted to pH 8, extracted with dichloromethane (3×80 ml) and the combined organic layers were dried over magnesium sulfate and evaporated to dryness to provide the expected compound (100 mg, 46.5%). The crude product thus obtained showed the following characteristics:

HRMS calcd for $C_{29}H_{40}NO_8S$ $[M+H]^+$ 562.2475, obsd 562.2477; IR (film) ($cm^{-1}$): 3513 (OH), 3369 (OH), 1744 (CO2), 1688 (COS), 1655 (C=C—O), 1503 (Ar), 1223 (C—O), 1150 (C—O), 1081 (C—O), 1035 (C—O), 911. $^1$H NMR 400 MHz (CDCl$_3$) (δ ppm, J Hz): 6.62 (1H, s, H-17*), 6.54 (1H, s, H-14*), 6.01 (1H, d, $J_{3-4}$=9.7, H-3), 5.87 (2H, s, OCH$_2$O), 5.05 (1H, s, H-1), 3.78 (1H, d, $J_{4-3}$=9.6, H-4), 3.68 (3H, s, OCH$_3$), 3.42 (1H, s, 2'-OH), 3.09 (2H, m, H-11β+H-8α), 2.94 (1H, m, H-10α), 2.59 (2H, m, H-8β+H-10β), 2.50 and 2.03 (2H, 2d, $J_{AB}$=15.8, CH$_2$COS), 2.40 (1H, m, H-11α), 2.23 (3H, s, SCH$_3$), 2.03 (1H, m, H-6$_A$), 1.91 (1H, m, H-6$_B$), 1.76 (2H, m, CH$_2$-7), 1.6–1.2 (6H, m, 3×CH$_2$), 1.19 (3H, s, CH$_3$), 1.18 (3H, s, CH$_3$).

EXAMPLE 31

Preparation of (2'S)-4'-Ethylthio-4'-demethoxy-epi-homoharringtonine

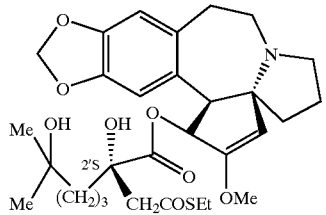

To a stirred solution of 4'-ethylthio-4'-demethoxy-anhydro-epi-homoharringtonine (18 mg, 0.032 mmol) resulting from Example 10 in dry dichloromethane (90 □l) under nitrogen was added at −10° C. a commercial solution of hydrobromic acid in acetic acid (58 μl, 0.29 mmol, HBr 30% w/w). After stirring at −10° C. for 3 hours, was added water (2 ml) and the temperature was raised to 20° C. After stirring at 20° C. for 3 hours, was added a sodium carbonate solution (0.76 M, 2 ml) up to pH 8. The resulting aqueous layer, after saturation with sodium chloride, was extracted with dichloromethane (3×2 ml) and the combined organic layers were dried over magnesium sulfate and evaporated to dryness to provide the expected compound (18 mg crude, 76%). The crude product thus obtained showed the following characteristics:

$^1$H NMR 400 MHz (CDCl$_3$) (δ ppm, J Hz): 6.66 (1H, s, H-17*), 6.59 (1H, s, H-14*), 5.95 and 5.85 (2H, 2d, $J_{AB}$=1.2, OCH$_2$O), 5.95 (1H, d, $J_{3-4}$=9.7, H-3), 5.03 (1H, s, H-1), 3.78 (1H, d, $J_{4-3}$=9.7, H-4), 3.66 (3H, s, OCH$_3$), 3.43 (1H, s, 2'-OH), 3.12 (2H, m, H-11β+H-8α), 2.94 (1H, m, H-10α), 2.89 (2H, m, SCH$_2$CH$_3$), 2.79 (2H, m, CH$_2$COS), 2.58 (2H, m, H-8β+H-10β), 2.40 (1H, dd, $J_{AB}$=14.2, J=6.9, H-11α), 2.02 (1H, m, H-6$_A$), 1.90 (1H, m, H-6$_B$), 1.76 (2H, m, CH$_2$-7), 1.5–0.6 (6H, m, 3×CH$_2$), 1.24 (3H, t, J=7.4, SCH$_2$CH$_3$), 1.16 (3H, s, CH$_3$), 1.15 (3H, s, CH$_3$).

EXAMPLE 32

Preparation of (2'R)-4'-Ethylthio-4-demethoxy-homoharringtonine

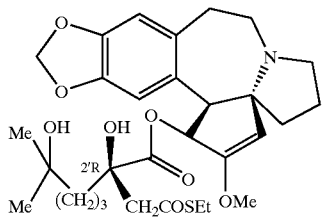

To a stirred solution of 4'-ethylthio-4'-demethoxy-anhydro-homoharringtonine (251 mg, 0.45 mmol) resulting from Example 11 in dry dichloromethane (1.1 ml) under nitrogen was added at −10° C. a commercial solution of hydrobromic acid in acetic acid (0.803 ml, 4.05 mmol, HBr 30% w/w). After stirring at −10° C. for 3 hours, was added water (14.6 ml) and the temperature was raised to 20° C. After stirring at 20° C. for 3 hours, was added a sodium carbonate solution (0.76 M, 35.9 ml) up to pH 8–9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15–40 μm (8 g), dichloromethane then dichloromethane/methanol, 99.5:0.5 to 95:5) to provide the expected compound (120 mg, 46%). The product thus obtained showed the following characteristics:

HRMS calcd for $C_{30}H_{42}NO_8S$ $[M+H]^+$ 576.2631, obsd 576.2624; IR (film) ($cm^{-1}$): 3514 (OH), 3391 (OH), 1744 (CO2), 1687 (COS), 1656 (C=C—O), 1504 (Ar), 1223 (C—O), 1159 (C—O), 1081 (C—O), 1035 (C—O), 911. $^1$H NMR 400 MHz (CDCl$_3$) (δ ppm, J Hz): 6.63 (1H, s, H-17*), 6.54 (1H, s, H-14*), 5.99 (1H, d, $J_{3-4}$=9.8, H-3), 5.97 (2H, s, OCH$_2$O), 5.05 (1H, s, H-1), 3.78 (1H, d, $J_{4-3}$=9.8, H-4), 3.67 (3H, s, OCH$_3$), 3.43 (1H, s, 2'-OH), 3.09 (2H, m, H-11β+H-8α), 2.94 (1H, m, H-10α), 2.84 (2H, m, SCH$_2$CH$_3$), 2.59 (2H, m, H-8β+H-10β), 2.46 and 1.98 (2H, 2d, $J_{AB}$=15.8, CH$_2$COS), 2.38 (1H, dd, $J_{AB}$=14.0, J=6.9, H-11α), 2.02 (1H, m, H-6$_A$), 1.90 (1H, m, H-6$_B$), 1.75 (2H, m, CH$_2$-7), 1.5–1.1 (6H, m, 3×CH$_2$), 1.21 (3H, t, J=7.5, SCH$_2$CH$_3$), 1.19 (3H, s, CH$_3$), 1.18 (3H, s, CH$_3$).

EXAMPLE 33

Preparation of (2'S)-4'-Isopropylthio-4'-demethoxy-epi-homoharringtonine

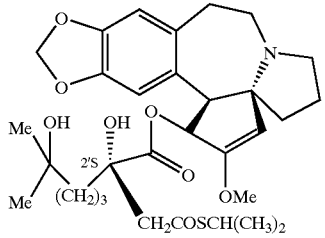

To a stirred solution of 4'-isopropylthio-4'-demethoxy-anhydro-epi-homoharringtonine (28 mg, 0.049 mmol) resulting from Example 12 in dry dichloromethane (0.14 ml) under nitrogen was added at −10° C. a commercial solution of hydrobromic acid in acetic acid (88 μl, 0.44 mmol, HBr 30% w/w). After stirring at −10° C. for 3 hours, was added water (2 ml) and the temperature was raised to 20° C. After stirring at 20° C. for 3 hours, was added a sodium carbonate solution (0.76 M, 4 ml) up to pH 8–9. The resulting aqueous layer, after saturation with sodium chloride, was extracted with dichloromethane (3×3 ml) and the combined organic layers were dried over magnesium sulfate and evaporated to dryness to provide the expected compound (19 mg crude, 66%). The crude product thus obtained showed the following characteristics:

$^1$H NMR 400 MHz (CDCl$_3$) (δ ppm, J Hz): 6.65 (1H, s, H-17), 6.59 (1H, s, H-14), 5.94 (1H, d, J3–4=10.0, H-3), 5.94 and 5.88 (2H, 2d, $J_{AB}$=1.4, OCH$_2$O), 5.03 (1H, s, H-1), 3.78 (1H, d, $J_{4-3}$=9.7, H-4), 3.66 (3H, s, OCH$_3$), 3.64 (1H, m, C$\underline{H}$(CH$_3$)$_2$), 3.41 (1H, s, OH), 3.11 (2H, m, H-11β+H-8α), 2.96 (1H, m, H-10α), 2.77 (2H, m, C$\underline{H}_2$COS), 2.59 (2H, m, H-8β+H-10β), 2.40 (1H, dd, $J_{AB}$=14.2, J=6.9, H-11α), 2.04 (1H, m, H-6$_A$), 1.90 (1H, m, H-6$_B$), 1.76 (2H, m, CH$_2$-7), 1.7–0.6 (6H, m, 3×CH$_2$), 1.29 and 1.27 (6H, 2d, J=6.8, CH(C$\underline{H}_3$)$_2$), 1.16 (3H, s, CH$_3$), 1.15 (3H, s, CH$_3$).

EXAMPLE 34

Preparation of (2'R)-4'-Isopropylthio-4'-demethoxy-homoharringtonine

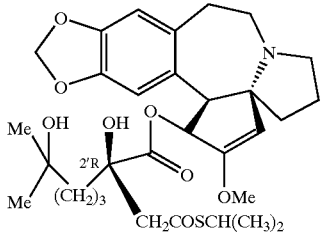

To a stirred solution of 4'-isopropylthio-4'-demethoxy-anhydro-homoharringtonine (267 mg, 0.467 mmol) resulting from Example 13 in dry dichloromethane (1.1 ml) under nitrogen was added at −10° C. a commercial solution of hydrobromic acid in acetic acid (0.839 ml, 4.2 mmol, HBr 30% w/w). After stirring at −10° C. for 3 hours, was added water (15.6 ml) and the temperature was raised to 20° C. After stirring at 20° C. for 3 hours, was added a sodium carbonate solution (0.76 M, 38.2 ml) up to pH 8–9. The resulting aqueous layer, after saturation with sodium chloride, was extracted with dichloromethane (3×20 ml) and the combined organic layers were dried over magnesium sulfate and evaporated to dryness. The resulting crude product was purified by column chromatography (silica 15–40 μm (8 g), dichloromethane then dichloromethane/methanol, 99:1) to provide the expected compound (118 mg, 43%). The product thus obtained showed the following characteristics:

HRMS calcd for C$_{31}$H$_{44}$NO$_8$S [M+H]$^+$ 590.2788, obsd 590.2789 IR (film) (cm$^{-1}$): 3521 (OH), 3385 (OH), 1743 (CO2), 1681 (COS), 1656 (C=C—O), 1504 (Ar), 1223 (C—O), 1159 (C—O), 1082 (C—O), 1039 (C—O), 910. $^1$H NMR 400 MHz (CDCl3) (δ ppm, J Hz): 6.64 (1H, s, H-17), 6.55 (1H, s, H-14), 5.97 (1H, d, $J_{3-4}$=9.8, H-3), 5.88 (2H, s, OCH$_2$O), 5.05 (1H, s, H-1), 3.79 (1H, d, $J_{4-3}$=9.8, H-4), 3.67 (3H, s, OCH$_3$), 3.56 (1H, m, J=6.9, C$\underline{H}$(CH$_3$)$_2$), 3.44 (1H, s, 2'-OH), 3.10 (2H, m, H-11β+H-8α), 2.95 (1H, td, J=11.1 and 6.8, H-10α), 2.59 (2H, m, H-8β+H-10β), 2.40 and 1.92 (2H, 2d, $J_{AB}$=15.6, C$\underline{H}_2$COS), 2.38 (1H, dd, $J_{AB}$=13.9, J=6.7, H-11α), 2.02 (1H, m, H-6$_A$), 1.90 (1H, m, H-6$_B$), 1.76 (2H, m, CH$_2$-7), 1.6–1.1 (6H, m, 3×CH$_2$): 1.27 and 1.25 (6H, 2d, J=6.9, CH(C$\underline{H}_3$)$_2$), 1.18 (6H, 2s, 2×CH$_3$).

EXAMPLE 35

Preparation of (2'S)-4'-tert-Butylthio-4'-demethoxy-epi-homoharringtonine

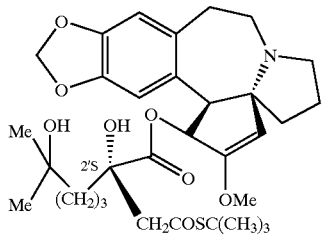

To a stirred solution of 4'-tert-butylthio-4'-demethoxy-anhydro-epi-homoharringtonine (60 mg, 0.102 mmol) resulting from Example 14 in dry dichloromethane (0.3 ml) under nitrogen was added at −10° C. a commercial solution of hydrobromic acid in acetic acid (0.183 ml, 0.44 mmol, HBr 30% w/w). After stirring at −10° C. for 3 hours, was added water (3 ml) and the temperature was raised to 20° C. After stirring at 20° C. for 3 hours, was added a sodium carbonate solution (0.76 M, 8.6 ml) up to pH 8–9. The resulting aqueous layer, after saturation with sodium chloride, was extracted with dichloromethane (3×8 ml) and the combined organic layers were dried over magnesium sulfate and evaporated to dryness to provide the expected compound (30 mg crude, 48%). The crude product thus obtained showed the following characteristics:

$^1$H NMR 400 MHz (CDCl$_3$) (δ ppm, J Hz): 6.65 (1H, s, H-17), 6.59 (1H, s, H-14), 5.96 and 5.89 (2H, 2d, J=1.3, OCH$_2$O), 5.96 (1H, d, $J_{3-4}$=9.9, H-3), 5.03 (1H, s, H-1), 3.78 (1H, d, $J_{4-3}$=9.7, H-4), 3.66 (3H, s, OCH$_3$), 3.39 (1H, s, 2'-OH), 3.13 (2H, m, H-11β+H-8α), 2.96 (1H, m, H-10α), 2.74 (2H, m, C$\underline{H}_2$COS), 2.62 (2H, m, H-8β+H-10β), 2.41 (1H, dd, $J_{AB}$=14.0, J=6.7, H-11α), 2.04 (1H, m, H-6$_A$), 1.91 (1H, m, H-6$_B$), 1.71 (2H, m, CH$_2$-7), 1.6–0.8 (6H, m, 3×CH$_2$), 1.44 (9H, s, C(CH$_3$)$_3$), 1.16 (3H, s, CH$_3$), 1.15 (3H, s, CH$_3$).

EXAMPLE 36

Preparation of (2'R)-4'-tert-Butylthio-4'-demethoxy-homoharringtonine

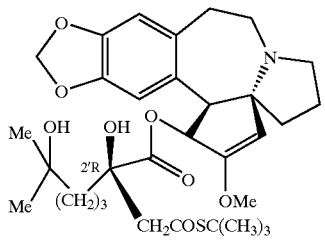

To a stirred solution of 4'-tert-butylthio-4'-demethoxy-anhydro-homoharringtonine (216 mg, 0.37 mmol) resulting from Example 15 in dry dichloromethane (1.1 ml) under nitrogen was added at −10° C. a commercial solution of hydrobromic acid in acetic acid (0.658 ml, 3.33 mmol, HBr 30% w/w). After stirring at −10° C. for 3 hours, was added water (12.6 ml) and the temperature was raised to 20° C. After stirring at 20° C. for 3 hours, was added a sodium carbonate solution (0.76 M, 31.5 ml) up to pH 8–9. The resulting aqueous layer, after saturation with sodium chloride, was extracted with dichloromethane (3×30 ml) and the combined organic layers were dried over magnesium sulfate and evaporated to dryness. The resulting crude product was purified by column chromatography (silica 15–40 □m (8 g), dichloromethane then dichloromethane/methanol, 99:1 to 95:5) to provide the expected compound (70 mg, 31.5%). The crude product thus obtained showed the following characteristics:

HRMS calcd for $C_{32}H_{46}NO_8S$ $[M+H]^+$ 604.2944, obsd 604.2940; IR (film) (cm$^{-1}$): 3514 (OH), 3369 (OH), 1744 (CO2), 1679 (COS), 1655 (C=C—O), 1504 (Ar), 1223 (C—O), 1159 (C—O), 1081 (C—O), 1035 (C—O), 910. $^1$H NMR 400 MHz (CDCl$_3$) (δ ppm, J Hz): 6.65 (1H, s, H-17), 6.54 (1H, s, H-14), 5.96 (1H, d, $J_{3-4}$=9.7, H-3), 5.89 (2H, s, OCH$_2$O), 5.05 (1H, s, H-1), 3.78 (1H, d, $J_{4-3}$=9.9, H-4), 3.67 (3H, s, OCH$_3$), 3.46 (1H, s, 2'-OH), 3.09 (2H, m, H-11β+H-8α), 2.95 (1H, m, H-10α), 2.59 (2H, m, H-8□+H-10β), 2.32 and 1.81 (2H, 2d, $J_{AB}$=15.5, $\underline{CH_2}$COS), 2.38 (1H, m, H-11α), 2.03 (1H, m, H-6$_A$), 1.91 (1H, m, H-6$_B$), 1.76 (2H, m, CH$_2$-7), 1.6–1.1 (6H, m, 3×CH$_2$), 1.42 (9H, s, C(C$\underline{H}_3$)$_3$), 1.18 (3H, s, CH$_3$), 1.175 (3H, s, CH$_3$).

EXAMPLE 37

Preparation of (2'R)-4'-(but-2-Enyl)-4'-demethyl-homoharringtonine

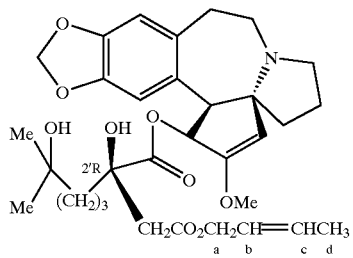

Sodium hydride 60% (15 mg, 0.366 mmol) was added to a solution of homoharringtonine (500 mg, 0.917 mmol) in crotyl alcohol (1 ml) and the resulting mixture was stirred at ambient temperature for 2.5 hours. After adjusting to pH 4 by addition of hydrochloric acid 1N the aqueous layer was washed with ether (3×10 ml). The resulting aqueous layer was alkalinized with ammonia 25% and was extracted with dichloromethane (3×10 ml). The combined organic layers were dried over magnesium sulfate and evaporated to dryness (454 mg crude, 70%). The crude product thus obtained was purified by phase-reversed chromatography (octadecylsilane 12 μm (100 g), buffer pH 3/methanol, 55:45). After removal of methanol in vacuo the resulting aqueous layer was alkalinized to pH 9.2 with ammonia 25% and extracted with dichloromethane (6×10 ml). The combined organic layers were dried over magnesium sulfate and evaporated to dryness to provide the expected compound (122 mg; 30%). The product thus obtained showed the following characteristics:

$^1$H NMR 400 MHz (CDCl$_3$) (δ ppm, J Hz): 6.62 (1H, s, H-17*), 6.54 (1H, s, H-14*), 5.98 (1H, d, $J_{3-4}$=9.8, H-3), 5.86 and 5.85 (2H, 2d, $J_{AB}$=1.5, OCH$_2$O), 5.74 (1H, m, H-c), 5.53 (1H, m, H-b), 5.05 (1H, s, H-1), 4.46 and 4.35 (2H, 2dd, $J_{AB}$=12.3, $J_{a-b}$=6.5, CH$_2$-a), 3.77 (1H, d, $J_{4-3}$=9.8, H-4), 3.68 (3H, s, OCH$_3$), 3.55 (1H, s, 2'-OH), 3.10 (2H, m, H-11β+H-8α), 2.94 (1H, m, H-10α), 2.58 (2H, m, H-8β+H-10β), 2.38 (1H, m, H-11α), 2.25 and 1.90 (2H, 2d, $J_{AB}$=16.4, $\underline{CH_2}$CO$_2$), 2.02 (1H, m, H-6$_A$), 1.90 (1H, m, H-6$_B$), 1.76 (2H, m, CH$_2$-7), 1.72 (3H, dd, $J_{d-c}$=6.6, $J_{d-b}$=1.2, CH$_{3-d}$), 1.39 (6H, m, 3×CH$_2$), 1.18 (6H, 2s, 2×CH$_3$).

EXAMPLE 38

Preparation of (2'S)-4'-(but-2-Enyl)-4'-demethyl-epi-homoharringtonine

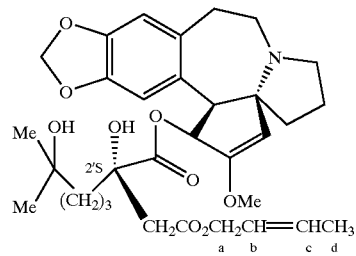

Sodium hydride 60% (15 mg, 0.366 mmol) was added to a solution of homoharringtonine (500 mg, 0.917 mmol) in crotyl alcohol 0 ml) and the resulting mixture was stirred at ambient temperature for 2 hours. After adjusting to pH 4 by addition of hydrochloric acid 1 N the aqueous layer was washed with ether (3×10 ml) and diluted with water (50 ml). The resulting aqueous layer was alkalinized to pH 10.6 with ammonia 25% and was extracted with dichloromethane (5×15 ml). The combined organic layers were dried over magnesium sulfate and evaporated to dryness (456 mg crude, 78%). The crude product thus obtained was purified by phase-reversed chromatography (octadecylsilane 12 μm (100 g), buffer pH 3/methanol, 65:35). After removal of methanol in vacuo the resulting aqueous layer was alkalinized to pH 9.5 with ammonia 25% and extracted with dichloromethane (56×10 ml). The combined organic layers were dried over magnesium sulfate and evaporated to dryness to provide the expected compound (188 mg; 32%). The product thus obtained showed the following characteristics:

$^1$H NMR 400 MHz (CDCl$_3$) (δ ppm, J Hz): 6.64 (1H, s, H-17*), 6.60 (1H, s, H-14*), 5.94 (1H, d, $J_{3-4}$=9.7, H-3), 5.94 and 5.85 (2H, 2d, $J_{AB}$=1.2, OCH$_2$O), 5.76 (1H, m, H-c), 5.54 (1H, m, H-b), 5.03 (1H, s, H-1), 4.49 (2H, m, CH$_2$-a), 3.78 (1H, d, $J_{4-3}$=9.7, H-4), 3.66 (3H, s, OCH$_3$), 3.53 (1H, s, 2'-OH), 3.10 (2H, m, H-11β+H-8α), 2.94 (1H, m, H-10α), 2.61 and 2.52 (2H, 2d, $J_{AB}$=16.7, $\underline{CH_2}$CO$_2$), 2.59 (2H, m, H-8β+H-10β), 2.39 (1H, dd, J=14.1 and 6.8, H-11α), 2.02 (1H, m, H-6$_A$), 1.90 (1H, m, H-6$_B$), 1.72 (2H, m, CH$_2$-7) and (3H, dd, $J_{d-c}$=6.5, $J_{d-b}$=0.9, CH$_{3-d}$), 1.20 (3H, m, CH$_2$), 1.16 (3H, s, C$\underline{H}_3$), 1.15 (3H, s, CH$_3$), 1.06 (1H, m, C$\underline{H}_2$), 0.93 (1H, m, CH$_2$), 0.736 (1H, m, C$\underline{H}_2$),

EXAMPLE 39

Preparation of (2'R)-4'-(3-Methyl-2-butenyl)-4'-demethyl-homoharringtonine

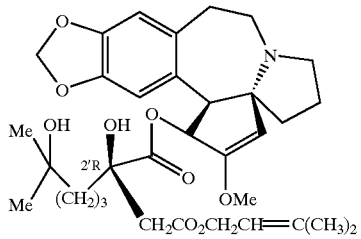

Sodium hydride 60% (29.4 mg, 0.735 mmol) was added to a solution of homoharringtonine (500 mg, 0.917 mmol) in 3-methyl-2-butenol (4 ml) and the resulting mixture was stirred at ambient temperature for 1.5 hours under argon. After adjusting to pH 2.5 by addition of hydrochloric acid 0.1N (15 ml) the aqueous layer was washed with ether (3×15 ml). The resulting aqueous layer was alkalinized with ammonia 25% (1.5 ml) and was extracted with dichloromethane (6×15 ml). The combined organic layers were dried over magnesium sulfate and evaporated to dryness (464 mg crude, 85%). The crude product thus obtained was purified by phase-reversed chromatography (octadecylsilane 12 μm (100 g), buffer pH 3/methanol, 47:53). After removal of methanol in vacuo the resulting aqueous layer was alkalinized to pH 9 with ammonia 25% and extracted with dichloromethane (3×5 ml). The combined organic layers were dried over magnesium sulfate and evaporated to dryness to provide the expected compound (266 mg; 48%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.86 and 5.84 (2H, 2d, J=1.5, OCH$_2$O), 5.28 (1H, m, H—C=), 5.05 (1H, s, H-1), 4.54 and 4.42 (2H, 2dd, J$_{AB}$=12.4, J=7.1, OCH$_2$), 3.77 (1H, d, J$_{4-3}$=9.8, H-4), 3.68 (3H, s, OCH$_3$), 3.54 (1H, s, 2'-OH), 3.10 (2H, m, H-11β+H-8α), 2.94 (1H, dt, J=11.5 and 7.0, H-10α), 2.58 (2H, m, H-8β+H-10β), 2.38 (1H, dd, J$_{AB}$=14.0, J=6.7, H-11α), 2.24 and 1.89 (2H, 2d, J$_{AB}$=16.4, CH$_2$CO$_2$), 2.04 (1H, m, H-6$_A$), 1.90 (1H, m, H-6$_B$), 1.77 (2H, m, CH$_2$-7), 1.75 (3H, s, CH$_3$—C=), 1.68 (3H, s, CH$_3$—C=) 1.39 (6H, m, 3×CH$_2$), 1.19 (3H, s, CH$_3$), 1.18 (3H, s, CH$_3$).

EXAMPLE 40

Preparation of (2'R)-4'-(2-Propenyl)-4'-demethyl-homoharringtonine

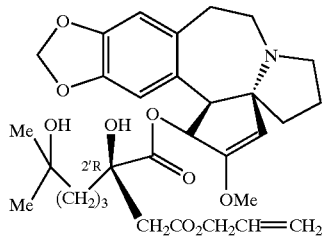

Sodium hydride 60% (29.8 mg, 0.745 mmol) was added to a solution of homoharringtonine (508 mg, 0.932 mmol) in 2-propenol (5 ml) and the resulting mixture was stirred at ambient temperature for 2 hours under argon. After adjusting to pH 2.1 by addition of hydrochloric acid 0.1N (17 ml) the aqueous layer was washed with ether (3×15 ml). The resulting aqueous layer was alkalinized with ammonia 25% (1.5 ml) and was extracted with dichloromethane (6×15 ml). The combined organic layers were dried over magnesium sulfate and evaporated to dryness (417 mg crude, 78%). The crude product thus obtained was purified by phase-reversed chromatography (octadecylsilane 12 μm (100 g), buffer pH 3/methanol, 61.5:38.5). After removal of methanol in vacuo the resulting aqueous layer was alkalinized to pH 10 with ammonia 25% and extracted with dichloromethane (5×10 ml). The combined organic layers were dried over magnesium sulfate and evaporated to dryness to provide the expected compound (289 mg; 54%). The product thus obtained showed the following characteristics:

$^1$H NMR 400 MHz (CDCl$_3$) (δ ppm, J Hz): 6.62 (1H, s, H-17), 6.54 (1H, s, H-14), 5.99 (1H, d, J$_{3-4}$=9.8, H-3), 5.87 (1H, m, HC=), 5.85 (2H, m, OCH$_2$O), 5.30 (1H, m, J=17.2, =CH$_2$), 5.22 (1H, m, J=10.4, =CH$_2$), 5.05 (1H, s, H-1), 4.53 and 4.42 (2H, 2m, J$_{AB}$=13.3, J=5.6, OCH$_2$), 3.77 (1H, d, J$_{4-3}$=9.8, H-4), 3.68 (3H, s, OCH$_3$), 3.52 (1H, s, 2'-OH), 3.10 (2H, m, H-11β+H-8α), 2.94 (1H, dt, J=11.0 and 6.9, H-10α), 2.59 (2H, m, H-8β+H-10β), 2.38 (1H, dd, J$_{AB}$=14.0, J=6.7, H-11α), 2.28 and 1.90 (2H, 2d, J$_{AB}$=16.5, CH$_2$CO$_2$), 2.05 (1H, m, H-6$_A$), 1.90 (1H, m, H-6$_B$), 1.75 (2H, m, CH$_2$-7), 1.5–1.1 (6H, m, 3×CH$_2$), 1.29 (1H, s, 4"-OH), 1.19 (6H, 2s, 2×CH$_3$).

EXAMPLE 41

Preparation of (2'R)-4'-(2-Methyl-2-propenyl)-4'-demethyl-homoharringtonine

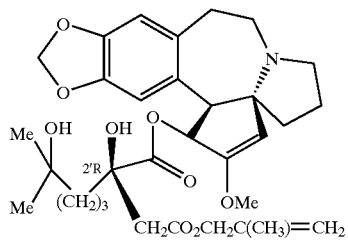

Sodium hydride 60% (23.5 mg, 0.470 mmol) was added to a solution of homoharringtonine (400 mg, 0.734 mmol) in 2-methyl-2-propenol (4 ml) and the resulting mixture was stirred at ambient temperature for 2 hours under argon. After adjusting to pH 2 by addition of hydrochloric acid 0.1N (15 ml) the aqueous layer was washed with ether (3×8 ml). The resulting aqueous layer was alkalinized with ammonia 25% (0.3 ml) and was extracted with dichloromethane (4×8 ml). The combined organic layers were dried over magnesium sulfate and evaporated to dryness (302 mg crude, 70%). The crude product thus obtained was purified by phase-reversed chromatography (octadecylsilane 12 μm (100 g), buffer pH 3/methanol, 55:45). After removal of methanol in vacuo the resulting aqueous layer was alkalinized to pH 9.8 with ammonia 25% (0.9 ml) and extracted with dichloromethane (5×10 ml). The combined organic layers were dried over magnesium sulfate and evaporated to dryness to provide the expected compound (183 mg; 43%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.85 (2H, s, OCH$_2$O), 5.05 (1H, s, H-1), 4.96 and 4.91 (2H, 2s, =CH$_2$), 4.47 and 4.33 (2H, 2d, J$_{AB}$=13.3, OCH$_2$), 3.77 (1H, d, J$_{4-3}$=9.8, H-4), 3.68 (3H, s, OCH$_3$), 3.51 (1H, s, 2'-OH), 3.09 (2H, m, H-11β+H-8α), 2.94 (1H, dt, J=11.0 and 6.8, H-10α), 2.59 (2H, m, H-8β+H-10β), 2.38 (1H, dd, J$_{AB}$=14.0, J=6.7, H-11α), 2.30 and 1.92 (2H, 2d, J$_{AB}$=16.5, C$\underline{H}_2$CO$_2$), 2.02 (1H, m, H-6$_A$), 1.90 (1H, m, H-6$_B$), 1.75 (2H, m, CH$_2$-7), 1.73 (3H, s, CH$_3$—C≡), 1.5–1.1 (6H, m, 3×CH$_2$), 1.19 (6H, 2s, 2×CH$_3$).

EXAMPLE 42

Preparation of (2'R)-4'-(2-Butynyl)-4'-demethyl-homoharringtonine

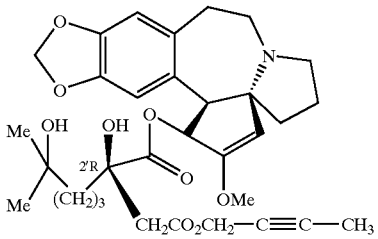

Sodium hydride 60% (30 mg, 0.75 mmol) was added (in 5 parts, at t=0, t=1.5, t=3.5, t=5 and t=24 hours) to a solution of homoharringtonine (510 mg, 0.936 mmol) in 2-butynol (2.9 ml) with stirring at ambient temperature under argon. 2 hours after the last addition the mixture was adjusted to pH 2.1 by addition of hydrochloric acid 0.1 N (17 ml) and the aqueous layer was washed with ether (3×10 ml). The resulting aqueous layer was alkalinized with ammonia 25% (0.3 ml) and was extracted with dichloromethane (6×10 ml). The combined organic layers were dried over magnesium sulfate and evaporated to dryness (368 mg crude, 67.5%). The crude product thus obtained was purified by phase-reversed chromatography (octadecylsilane 12 □m (100 g), buffer pH 3 1 methanol, 65:35). After removal of methanol in vacuo the resulting aqueous layer was alkalinized to pH 10 with ammonia 25% (0.4 ml) and extracted with dichloromethane (6×8 ml). The combined organic layers were dried over magnesium sulfate and evaporated to dryness to provide the expected compound (171 mg; 46.5%). The product thus obtained showed the following characteristics:

$^1$H NMR 400 MHz (CDCl$_3$) (δ ppm, J Hz): 6.62 (1H, s, H-17), 6.54 (1H, s, H-14), 5.99 (1H, d, J$_{3-4}$=9.5, H-3), 5.94 and 5.87 (2H, 2d, J$_{AB}$=1.5, OCH$_2$O), 5.05 (1H, s, H-1), 4.60 and 4.48 (2H, 2dq, J$_{AB}$=15.2, J=2.4, OCH$_2$), 3.77 (1H, d, J$_{4-3}$=9.8, H-4), 3.67 (3H, s, OCH$_3$), 3.51 (1H, s, 2'-OH), 3.09 (2H, m, H-11β+H-8α), 2.94 (1H, m, H-10α), 2.59 (2H, m, H-8β+H-10β), 2.38 (1H, dd, J$_{AB}$=13.9, J=6.7, H-11α), 2.30 and 1.88 (2H, 2d, J$_{AB}$=16.5, C$\underline{H}_2$CO$_2$), 2.02 (1H, m, H-6$_A$), 1.88 (1H, m, H-6$_B$), 1.86 (3H, t, J=2.4, C$\underline{H}_3$—C≡), 1.76 (2H, m, CH$_2$-7), 1.5–1.1 (6H, m, 3×CH$_2$), 1.19 (3H, s, CH$_3$), 1.18 (3H, s, CH$_3$).

EXAMPLE 43

Preparation of (2'R)-4'-(hexa-2,4-Dienyl)-4'-demethyl-homoharringtonine

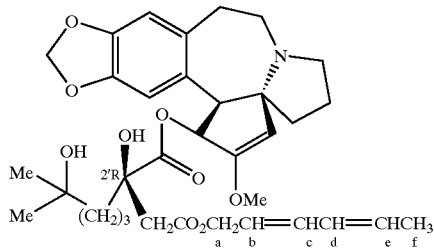

Sodium hydride 60% (8.8 mg, 0.22 mmol) was added to a solution of homoharringtonine (300 mg, 0.55 mmol) in (E,E)-hexa-1,4-dienol (3 ml) and the resulting mixture was stirred at 35° C. for 1 h 45 min under argon. After adjusting to pH 1.9 by addition of hydrochloric acid 0.1N (9 ml) the aqueous layer was washed with ether (3×6 ml). The resulting aqueous layer was alkalinized to pH 10 with ammonia 25% (0.3 ml) and was extracted with dichloromethane (4×6 ml). The combined organic layers were dried over magnesium sulfate and evaporated to dryness (224 mg crude, 67%). The crude product thus obtained was purified by phase-reversed chromatography (octadecylsilane 12 □m (100 g), buffer pH 3/methanol, 40:60). After removal of methanol in vacuo the resulting aqueous layer was washed with ether (10 ml), alkalinized to pH 9.5 with ammonia 25% (0.3 ml) and extracted with dichloromethane (6×8 ml). The combined organic layers were dried over magnesium sulfate and evaporated to dryness to provide the expected compound (175 mg; 43%). The product thus obtained showed the following characteristics:

$^1$H NMR 400 MHz (CDCl3) (δ ppm, J Hz): 6.62 (1H, s, H-17), 6.53 (1H, s, H-14), 6.22 (1H, dd, J$_{c-b}$=15.2, J$_{c-d}$=10.5, H-c), 6.06 (1H, ddd, J$_{d-e}$=15.0, J$_{d-c}$=10.6, J$_{d-f}$=1.4, H-d), 5.98 (1H, d, J$_{3-4}$=9.8, H-3), 5.84 and 5.83 (2H, 2d, J$_{AB}$=1.5, OCH$_2$O), 5.76 (1H, dq, J$_{e-d}$=15.0, J$_{e-f}$=6.8, H-e), 5.56 (1H, dt, J$_{b-c}$=15.3, J$_{b-a}$=6.6, H-b), 5.05 (1H, s, H-1), 4.53 and 4.42 (2H, 2dd, J$_{AB}$=12.8, J$_{a-b}$=6.6, CH$_2$-a), 3.70 (1H, d, J$_{4-3}$=9.8, H-4), 3.67 (3H, s, OCH$_3$), 3.52 (1H, s, 2'-OH), 3.09 (2H, m, H-11β+H-8α), 2.94 (1H, dt, J=11.5 and 6.9, H-10α), 2.58 (2H, m, H-8β+H-10β), 2.38 (1H, dd, J$_{AB}$=14.0, J=6.7, H-11α), 2.26 and 1.88 (2H, 2d, J$_{AB}$=16.4, C$\underline{H}_2$CO$_2$), 2.02 (1H, m, H-6$_A$), 1.90 (1H, m, H-6$_B$), 1.77 (3H, d, J~6, CH$_3$-f) and (2H, m, CH$_2$-7), 1.5–1.1 (6H, m, 3×CH$_2$), 1.28 (1H, s, 4"OH), 1.19 (3H, s, CH$_3$), 1.18 (3H, s, CH$_3$).

EXAMPLE 44

Preparation of (2'R)-4'-(Methylcyclopropyl)methyl-4'-demethyl-homoharringtonine

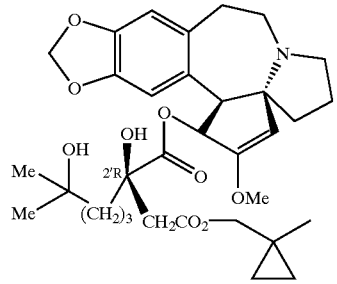

Sodium hydride 60% (3.8 mg, 0.095 mmol) was added to a solution of homoharringtonine (263 mg, 0.482 mmol) in (1-methylcyclopropyl)methanol (2.3 ml) and the resulting mixture was stirred at ambient temperature for 20 h under argon. After adjusting to pH 2 by addition of hydrochloric acid 0.1N (9 ml) the aqueous layer was washed with ether (3×10 ml). The resulting aqueous layer was alkalinized to pH 9.5 with ammonia 25% (0.3 ml) and was extracted with dichloromethane (6×8 ml). The combined organic layers were dried over magnesium sulfate and evaporated to dryness (231 mg crude, 80%). The crude product thus obtained was purified by phase-reversed chromatography (octadecylsilane 12 μm (100 g), buffer pH 3/methanol, 50:50). After removal of methanol in vacuo the resulting aqueous layer was alkalinized to pH 9.5 with ammonia 25% (0.4 ml) and extracted with dichloromethane (6×8 ml). The combined organic layers were dried over magnesium sulfate and evaporated to dryness to provide the expected compound (173 mg; 69%). The product thus obtained showed the following characteristics:

$^1$H NMR 400 MHz (CDCl3) (δ ppm, J Hz): 6.62 (1H, s, H-17), 6.55 (1H, s, H-14), 5.99 (1H, d, $J_{3-4}$=9.6, H-3), 5.86 (2H, s, OCH$_2$O), 5.06 (1H, s, H-1), 3.86 and 3.72 (2H, 2d, $J_{AB}$=11.2, CH$_2$-a), 3.78 (1H, d, $J_{4-3}$=9.6, H-4), 3.68 (3H, s, OCH$_3$), 3.53 (1H, s, 2'-OH), 3.10 (2H, m, H-11β+H-8α), 2.95 (1H, m, H-10α), 2.58 (2H, m, H-80β+H-10β), 2.39 (1H, dd, $J_{AB}$=14.0, J=6.7, H-11α), 2.28 and 1.95 (2H, 2d, $J_{AB}$=16.3, C$\underline{H}_2$CO$_2$), 2.02 (1H, m, H-6$_A$), 1.90 (1H, m, H-6$_B$), 1.76 (2H, m, CH$_2$-7), 1.5–1.1 (6H, m, 3×CH$_2$), 1.29 (1H, s, 4"-OH), 1.19 (6H, 2s, 2×CH$_3$), 1.09 (3H, s, CH$_3$-c), 0.44 and 0.35 (4H, 2m, CH$_2$-d,e).

EXAMPLE 45

Preparation of (−)-Cephalotaxyl(2'S)-2-(2,2,2-trifluoro-ethoxy)carbonylmethyl-6,6-dimethyl-2-tetrahydropyranecarboxylate or 4'-(2,2,2-Trifluoroethyl)-4'-demethyl-anhydro-epi-homoharringtonine

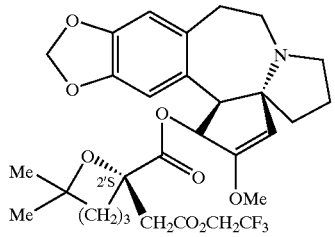

To a stirred mixture of 4'-demethyl-anhydro-epi-homoharringtonine (1 g, 1.947 mmol) in dry dichloromethane (10 ml) under argon was added at 0° C. triethylamine (dried over potassium hydroxide) (270 μl, 1.947 mmol) and 2,4,6-trichlorobenzoyl chloride (305 μl, 1.947 mmol) over a period of 10 minutes. After stirring at ambient temperature for 2.5 hours a solution of 4-dimethylaminopyridine (476 mg, 3.896 mmol) and 2,2,2-trifluoroethanol (280 μl, 3.899 mmol) in dry dichloromethane (3 ml) was added. After stirring at ambient temperature for 20 hours, the reaction mixture was diluted with dichloromethane (19 ml). The resulting organic layer was successively washed with water (27 ml), with saturated sodium hydrogen carbonate solution (27 ml), with brine (27 ml). After a last extraction of the combined aqueous layers with dichloromethane (27 ml) the combined organic layers were dried over magnesium sulfate and evaporated to dryness. The resulting crude product was purified by column chromatography (silica 15–40 μm (10 g), dichloromethane then dichloromethane/methanol, 99:1 to 80:20) to provide the expected compound (838 mg, 72%). The product thus obtained showed the following characteristics:

$^1$H NMR 400 MHz (CDCl$_3$) (δ ppm, J Hz): 6.61 (1H, s, H-14*), 6.57 (1H, s, H-17*), 5.83 (3H, m, H-3+OCH$_2$O), 5.02 (1H, s, H-1), 4.43 and 4.33 (2H, 2dq, $J_{AB}$=12.7, JH-F=8.6, OC$\underline{H}_2$CF$_3$), 3.78 (1H, d, $J_{4-3}$=9.7, H-4), 3.65 (3H, s, OCH$_3$), 3.23 (1H, m, H-11β), 3.09 (1H, m, H-8α), 2.94 (1H, dt, J=11.6 and 7.2, H-10α), 2.60 (2H, m, H-8β+H-10β), 2.39 (1H, m, H-11α), 2.18 and 1.84 (2H, 2d, $J_{AB}$=14.5, C$\underline{H}_2$CO$_2$), 2.01 (1H, m, H-6$_A$), 1.89 (1H, m, H-6$_B$), 1.74 (2H, m, CH$_2$-7), 1.5–1.2 (6H, m, 3×CH$_2$), 1.10 (3H, s, CH$_3$), 1.03 (3H, s, CH$_3$).

EXAMPLE 46

Preparation of (2'S)-4'-(2,2,2-Trifluoroethyl)-4'-demethyl-epi-homoharringtonine

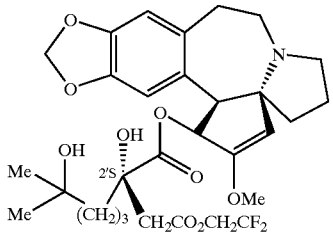

To a stirred solution of 4'-(2,2,2-trifluoroethyl)-4'-demethyl-anhydro-epi-homoharringtonine (300 mg, 0.504 mmol) resulting from Example 45 in dry dichloromethane (1.55 ml) under argon was added at −10° C. a commercial solution of hydrobromic acid in acetic acid (0.903 ml, 4.53 mmol, HBr 30% w/w). After stirring at −10° C. for 3 hours, was added water (14 ml) and the temperature was raised to 20° C. After stirring at 20° C. for 2.75 hours, was added a sodium carbonate solution (0.76 M, 25 ml) up to pH 8.7. The resulting aqueous layer, after saturation with sodium chloride, was extracted with dichloromethane (3×11.4 ml) and the combined organic layers were dried over magnesium sulfate and evaporated to dryness. The resulting crude product was purified by column chromatography (silica 15–40 μm (15 g), dichloromethane/methanol, 99:1 to 90:10) to provide the expected compound (211 mg, 68%). The product thus obtained showed the following characteristics:

$^1$H NMR 400 MHz (CDCl$_3$) (δ ppm, J Hz): 6.65 (1H, s, H-17*), 6.60 (1H, s, H-14*), 5.94 and 5.85 (2H, 2d, $J_{AB}$=1.3, OCH$_2$O), 5.93 (1H, d, H-3), 5.05 (1H, s, H-1), 4.53 and 4.32 (2H, 2dq, $J_{AB}$=12.6, JH-F=8.4, OC$\underline{H}_2$CF$_3$), 3.79 (1H, d, $J_{4-3}$=9.6, H-4), 3.65 (3H, s, OCH$_3$), 3.36 (1H, s, 2'-OH), 3.08 (2H, m, H-11β+H-8α), 2.93 (1H, m, H-10α), 2.70 and 2.64 (2H, 2d, $J_{AB}$=16.8, C$\underline{H}_2$CO$_2$), 2.57 (2H, m, H-8β+H-10β), 2.38 (1H, dd, $J_{AB}$=14.0, J=6.8, H-11α), 2.01 (1H, m, H-6$_A$), 1.89 (1H, m, H-6$_B$), 1.76 (2H, m, CH$_2$-7), 1.34 (1H, s, 4"-OH), 1.3–1.15 (3H, m, CH$_2$), 1.17 (3H, s, CH$_3$), 1.16 (3H, s, CH$_3$), 1.03 (1H, m, CH$_2$), 0.97 (1H, m, C$\underline{H}_2$), 0.70 (1H, m, C$\underline{H}_2$).

EXAMPLE 47

Preparation of (−)-Cephalotaxyl(2'R)-2-(2,2,2-trifluoro-ethoxy)carbonylmethyl-6,6-dimethyl-2-tetrahydropyranecarboxylate or 4'-(2,2,2-Trifluoroethyl)-4'-demethyl-anhydro-homoharringtonine

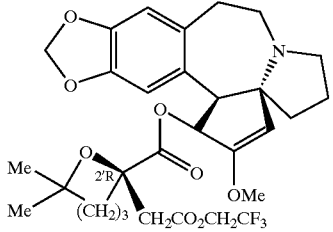

To a stirred mixture of 4'-demethyl-anhydro-homoharringtonine (723 mg, 1.407 mmol) in dry dichloromethane (5.1 ml) under argon was added at 0° C. triethylamine (dried over potassium hydroxide) (196 μl, 1.408 mmol) and 2,4,6-trichlorobenzoyl chloride (220 μl, 1.407 mmol) over a period of 10 minutes. After stirring at ambient temperature for 2.5 hours a solution of 4-dimethylaminopyridine (344 mg, 2.816 mmol) and 2,2,2-trifluoroethanol (202 μl, 2.813 mmol) in dry dichloromethane (2.2 ml) was added. After stirring at ambient temperature for 17 hours, the reaction mixture was diluted with dichloromethane (14 ml). The resulting organic layer was successively washed with water (19 ml), with saturated sodium hydrogen carbonate solution (19 ml), with brine (19 ml). After a last extraction of the combined aqueous layers with dichloromethane (19 ml) the combined organic layers were dried over magnesium sulfate and evaporated to dryness. The resulting crude product was purified by column chromatography (silica 15–40 □m (10 g), dichloromethane/methanol, 99:1 to 90:10) to provide the expected compound (523 mg, 77%). The product thus obtained showed the following characteristics:

$^1$H NMR 400 MHz (CDCl$_3$) (δ ppm, J Hz): 6.62 (1H, s, H-17), 6.58 (1H, s, H-14), 5.88 (1H, d, H-3), 5.86 and 5.79 (2H, 2d, $J_{AB}$=1.4, OCH$_2$O), 5.05 (1H, s, H-1), 4.41 and 4.35 (2H, 2m, OC$\underline{H}_2$CF$_3$), 3.80 (1H, d, $J_{4-3}$=9.7, H-4), 3.70 (3H, s, OCH$_3$), 3.12 (2H, m, H-11β)+H-8α), 2.96 (1H, m, H-10α), 2.60 (2H, m, H-8β+H-10β), 2.37 (1H, dd, J=14.1 and 6.7, H-11α), 2.20 and 1.68 (2H, 2d, $J_{AB}$=14.7, C$\underline{H}_2$CO$_2$), 2.01 (1H, m, H-6$_A$), 1.93 (1H, m, H-6$_B$), 1.76 (2H, m, CH$_2$-7), 1.7–1.2 (6H, m, 3×CH$_2$), 1.10 (3H, s, CH$_3$), 1.04 (3H, s, CH$_3$).

EXAMPLE 48

Preparation of (2'R)-4'-(2,2,2-Trifluoroethyl)-4'-demethyl-homoharringtonine

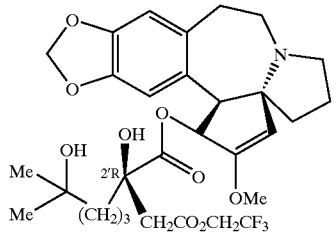

To a stirred solution of 4'-(2,2,2-trifluoroethyl)-4'-demethyl-anhydro-homoharringtonine (507 mg, 0.851 mmol) resulting from Example 47 in dry dichloromethane (2.6 ml) under argon was added at –10° C. a commercial solution of hydrobromic acid in acetic acid (1.525 ml, 7.659 mmol HBr 30% w/w). After stirring at –10° C. for 3 hours, was added water (24 ml) and the temperature was raised to 20° C. After stirring at 20° C. for 2.75 hours, was added a sodium carbonate solution (0.76 M, 44 ml) up to pH 8.5. The resulting aqueous layer, after saturation with sodium chloride, was extracted with dichloromethane (3×19 ml) and the combined organic layers were dried over magnesium sulfate and evaporated to dryness (508 mg crude, 97%). The crude product thus obtained was purified by phase-reversed chromatography (octadecylsilane 12 μm (100 g), buffer pH 3/methanol, 60:40 to 20:80). After removal of methanol in vacuo the resulting aqueous layer was alkalinized to pH 9.6 with ammonia 25% (0.4 ml) and extracted with dichloromethane (12×10 ml). The combined organic layers were dried over magnesium sulfate and evaporated to dryness to provide the expected compound (122 mg; 23%). The product thus obtained showed the following characteristics:

$^1$H NMR 400 MHz (CDCl$_3$) (δ ppm, J Hz): 6.62 (1H, s, H-17), 6.55 (1H, s, H-14), 5.99 (1H, d, $J_{3-4}$=9.7, H-3), 5.86 and 5.84 (2H, 2d, $J_{AB}$=1.2, OCH$_2$O), 4.42 and 4.26 (2H, 2dd, $J_{AB}$=12.7, $J_{H-F}$=8.4, OC$\underline{H}_2$CF$_3$), 5.05 (1H, s, H-1), 3.78 (1H, d, $J_{4-3}$=9.8, H-4), 3.68 (3H, s, OCH$_3$), 3.45 (1H, s, 2'-OH), 3.10 (2H, m, H-11β+H-8α), 2.96 (1H, m, H-10α), 2.60 (2H, m, H-8β+H-10β), 2.39 (1H, m, H-11α), 2.37 and 1.93 (2H, 2d, $J_{AB}$=16.5, C$\underline{H}_2$CO$_2$), 2.03 (1H, m, H-6$_A$), 1.92 (1H, m, H-6$_B$), 1.76 (2H, m, CH$_2$-7), 1.55–1.15 (6H, m, 3×CH$_2$), 1.25 (1H, s, 4"-OH), 1.19 (6H, 2s, 2×CH$_3$).

EXAMPLE 49

Preparation of (2'R)-4'-Cyclopropylmethyl-4'-demethyl-homoharringtonine

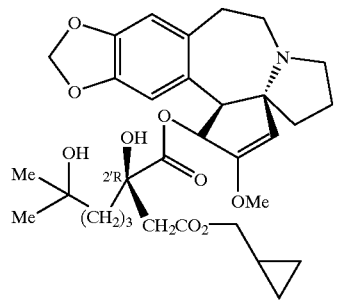

Sodium hydride 60% (3.2 mg, 0.08 mmol) was added to a solution of homoharringtonine (210 mg, 0.385 mmol) in cyclopropylmethanol (1.53 ml) and the resulting mixture was stirred at ambient temperature for 2.5 h under argon. After adjusting to pH 1.8 by addition of hydrochloric acid 0.1N (6 ml) the aqueous layer was washed with ether (3×5 ml). The resulting aqueous layer was alkalinized to pH 9.5 with ammonia 25% (0.3 ml) and was extracted with dichloromethane (6×5 ml). The combined organic layers were dried over magnesium sulfate and evaporated to dryness (175 mg crude, 78%). The crude product thus obtained was purified by phase-reversed chromatography (octadecylsilane 12 μm (100 g), buffer pH 3/methanol, 57:43). After removal of methanol in vacuo the resulting aqueous layer was alkalinized to pH 9.5 with ammonia 25% (0.4 ml) and extracted with dichloromethane (6×6 ml). The combined organic layers were dried over magnesium sulfate and evaporated to dryness to provide the expected compound (170 mg; 51%). The product thus obtained showed the following characteristics:

$^1$H NMR 400 MHz (CDCl3) (δ ppm, J Hz): 6.62 (1H, s, H-17), 6.55 (1H, s, H-14), 5.98 (1H, d, $J_{3-4}$=9.8, H-3), 5.87 and 5.86 (2H, 2d, $J_{AB}$=1.3, OCH$_2$O), 5.06 (1H, s, H-1), 3.83 and 3.77 (2H, 2dd, $J_{AB}$=11.4, $J_{a-b}$=1.3, CH$_2$-a), 3.78 (1H, d, $J_{4-3}$~10, H-4), 3.68 (3H, s, OCH$_3$), 3.55 (1H, s, 2'-OH), 3.10 (2H, m, H-11β+H-8α), 2.95 (1H, m, H-10α), 2.61 (2H, m, H-8β+H-10β), 2.39 (1H, dd, $J_{AB}$=14.1, J=6.8, H-11α), 2.27 and 1.93 (2H, 2d, $J_{AB}$=16.3, C$\underline{H}_2$CO$_2$), 2.03 (1H, m, H-6$_A$), 1.93 (1H, m, H-6$_B$), 1.76 (2H, m, CH$_2$-7), 1.5–1.1 (6H, m, 3×CH$_2$), 1.19 (3H, s, CH$_3$), 1.18 (3H, s, CH$_3$), 1.06 (1H, m, H-b), 0.55 and 0.24 (4H, 2m, CH$_2$-c,d).

EXAMPLE 50

Preparation of (2'R)-4'-Butyl-4'-demethyl-homoharringtonine

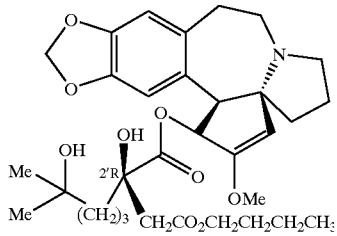

Sodium hydride 60% (4.95 mg, 0.124 mmol) was added to a solution of homoharringtonine (225 mg, 0.4125 mmol) in n-butanol (2.25 ml) and the resulting mixture was stirred at ambient temperature for 20 hours under argon. After adjusting to pH 1.9 by addition of hydrochloric acid 0.1N (6 ml) the aqueous layer was washed with ether (3×6 ml). The resulting aqueous layer was alkalinized to pH 10 with ammonia 25% (0.43 ml) and was extracted with dichloromethane (10×8 ml). The combined organic layers were dried over magnesium sulfate and evaporated to dryness (178 mg crude, 74%). The crude product thus obtained was purified by phase-reversed chromatography (octadecylsilane 12 lam (100 g), buffer pH 3/methanol, 50:50). After removal of methanol in vacuo the resulting aqueous layer was alkalinized to pH 9.5 with ammonia 25% (0.4 ml) and extracted with dichloromethane (8×10 ml). The combined organic layers were dried over magnesium sulfate and evaporated to dryness to provide the expected compound (107 mg; 44%). The product thus obtained showed the following characteristics:

$^1$H NMR 400 MHz (CDCl3) (δ ppm, J Hz): 6.62 (1H, s, H-17), 6.55 (1H, s, H-14), 5.98 (1H, d, $J_{3-4}$=9.7, H-3), 5.86 (2H, s, OCH$_2$O), 5.05 (1H, s, H-1), 4.02 and 3.92 (2H, 2dt, $J_{AB}$=10.8, $J_{a-b}$=6.8, CH$_2$-a), 3.78 (1H, d, $J_{4-3}$=9.8, H-4), 3.68 (3H, s, OCH$_3$), 3.52 (1H, s, 2'-OH), 3.11 (2H, m, H-11β+H-8α), 2.95 (1H, m, H-10α), 2.60 (2H, m, H-8β+H-10β), 2.39 (1H, dd, J=14.1 and 6.8, H-11α), 2.25 and 1.92 (2H, 2d, $J_{AB}$=16.3, CH$_2$CO$_2$), 2.03 (1H, m, H-6$_A$), 1.92 (1H, m, H-6$_B$), 1.76 (2H, m, CH$_2$-7), 1.55 (2H, m, CH$_2$-b), 1.45–1.15 (8H, m, CH$_2$-c and 3×CH$_2$), 1.19 (3H, s, CH$_3$), 1.18 (3H, s, CH$_3$), 0.92 (3H, t, J=7.3, CH$_3$-d).

EXAMPLE 51

Preparation of (2'R)-4'-Propyl-4'-demethyl-homoharringtonine

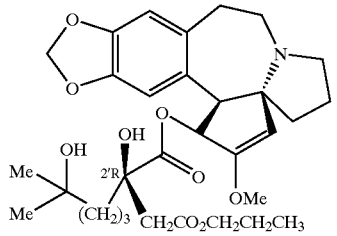

Sodium hydride 60% (8.9 mg, 0.223 mmol) was added to a solution of homoharringtonine (405 mg, 0.742 mmol) in n-propanol (4 ml) and the resulting mixture was stirred at ambient temperature for 1.5 h under argon. After adjusting to pH 1.9 by addition of hydrochloric acid 0.1N (12 ml) the aqueous layer was washed with ether (3×8 ml). The resulting aqueous layer was alkalinized to pH 9.6 with ammonia 25% (0.8 ml) and was extracted with dichloromethane (6×10 ml). The combined organic layers were dried over magnesium sulfate and evaporated to dryness (374 mg crude, 88%). The crude product thus obtained was purified by phase-reversed chromatography (octadecylsilane 12 μm (100 g), buffer pH 3/methanol, 62:38 to 50:50). After removal of methanol in vacuo the resulting aqueous layer was alkalinized to pH 9.5 with ammonia 25% (0.8 ml) and extracted with dichloromethane (6×10 ml). The combined organic layers were dried over magnesium sulfate and evaporated to dryness to provide the expected compound (244 mg; 57%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, $J_{3-4}$=9.7, H-3), 5.86 (2H, s, OCH$_2$O), 5.05 (1H, s, H-1), 3.97 and 3.89 (2H, 2dt, $J_{AB}$=10.6, $J_{a-b}$=6.8, CH$_2$-a), 3.78 (1H, d, $J_{4-3}$=9.8, H-4), 3.68 (3H, s, OCH$_3$), 3.52 (1H, s, 2'-OH), 3.10 (2H, m, H-11β+H-8α), 2.94 (1H, m, H-10α), 2.60 (2H, m, H-8β+H-10β), 2.38 (1H, dd, J=14.0 and 6.7, H-11α), 2.25 and 1.92 (2H, 2d, $J_{AB}$=16.3, CH$_2$CO$_2$), 2.02 (1H, m, H-6$_A$), 1.90 (1H, m, H-6$_B$), 1.76 (2H, m, CH$_2$-7), 1.60 (2H, m, CH$_2$-b), 1.5–1.1 (6H, m, 3×CH$_2$), 1.19 (3H, s, CH$_3$), 1.18 (3H, s, CH$_3$), 0.91 (3H, t, J=7.4, CH$_3$-c)

EXAMPLE 52

Preparation of (2'R)-4'-Isobutyl-4'-demethyl-homoharringtonine

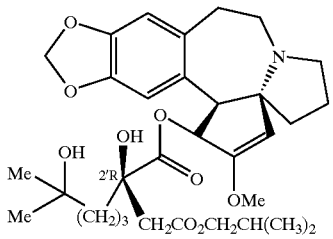

Sodium hydride 60% (8.8 mg, 0.220 mmol) was added to a solution of homoharringtonine (3975 mg, 0.7282 mmol) in iso-butanol (4 ml) and the resulting mixture was stirred at ambient temperature for 1.5 h under argon. After adjusting to pH 1.8 by addition of hydrochloric acid 0.1N (11 ml) the aqueous layer was washed with ether (3×8 ml). The resulting aqueous layer was alkalinized to pH 9.7 with ammonia 25% and was extracted with dichloromethane (6×10 ml). The combined organic layers were dried over magnesium sulfate and evaporated to dryness (316 mg crude, 768%). The crude product thus obtained was purified by phase-reversed chromatography (octadecylsilane 12 μm (135 g), buffer pH 3/5 methanol, 50:50). After removal of methanol in vacuo the resulting aqueous layer was alkalinized to pH 9.5 with ammonia 25% and extracted with dichloromethane (6×10 ml). The combined organic layers were dried over magnesium sulfate and evaporated to dryness to provide the expected compound (254 mg; 61%). The product thus obtained showed the following characteristics:

$^1$H NMR 400 MHz (CDCl$_3$) (δ ppm, J Hz): 6.62 (1H, s, H-17), 6.55 (1H, s, H-14), 5.98 (1H, d, $J_{3-4}$=9.5, H-3), 5.86 (2H, s, OCH$_2$O), 5.06 (1H, s, H-1), 3.81 and 3.71 (2H, 2dt, $J_{AB}$=10.7, $J_{a-b}$=6.7, CH$_2$-a), 3.78 (1H, d, $J_{4-3}$=9.5, H-4), 3.68 (3H, s, OCH$_3$), 3.52 (1H, s, 2'-OH), 3.11 (2H, m, 15

H-11βH-8α), 2.94 (1H, m, H-10a), 2.60 (2H, m, H-8β+H-10α), 2.38 (1H, dd, J=14.1 and 6.8, H-11α), 2.26 and 1.94 (2H, 2d, J$_{AB}$=16.3, C$\underline{H}_2$CO$_2$), 2.04 (1H, m, H-6$_A$), 1.90 (1H, m, H-6B), 1.85 (1H, m, H-b), 1.76 (2H, m, CH$_2$-7), 1.5–1.15 (6H, m, 3×CH$_2$), 1.19 (6H, 2s, 2×CH$_3$), 0.91 (3H, d, J$_{c-b}$=6.8, CH$_3$-c), 0.90 (3H, d, J$_{d-b}$=6.8, CH$_3$-d).

EXAMPLE 53

Preparation of (2'R)-4'-(hex-4-Enyl)-4'-demethyl-homoharringtonine

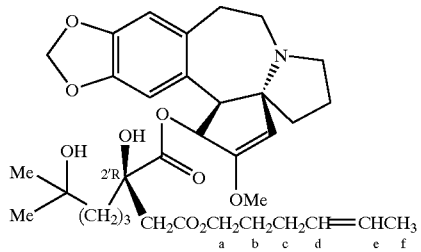

Sodium hydride 60% (10.96 mg, 0.274 mmol) was added to a solution of homoharringtonine (374 mg, 0.685 mmol) in 4-hexenol (4 ml) and the resulting mixture was stirred at ambient temperature for 45 min under argon. After adjusting to pH 1.9 by addition of hydrochloric acid 0.1N (12 ml) the aqueous layer was washed with ether (3×8 ml). The resulting aqueous layer was alkalinized to pH 10 with ammonia 25% and was extracted with dichloromethane (6×10 ml). The combined organic layers were dried over magnesium sulfate and evaporated to dryness (358 mg crude, 85%). The crude product thus obtained was purified by phase-reversed chromatography (octadecylsilane 12 μm (135 g), buffer pH 3/methanol, 30:70). After removal of methanol in vacuo the resulting aqueous layer was washed with ether (5 ml), dichloromethane (5 ml), alkalinized to pH 9.5 with ammonia 25% (0.8 ml) and extracted with dichloromethane (6×10 ml). The combined organic layers were dried over magnesium sulfate and evaporated to dryness to provide the expected compound (226 mg; 54%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.7, H-3), 5.85 (2H, s, OCH$_2$O), 5.42 (2H, m, H-e,d), 5.05 (1H, s, H-1), 3.99 and 3.92 (2H, 2m, CH$_2$-a), 3.78 (1H, d, J$_{4-3}$=9.7, H-4), 3.68 (3H, s, OCH$_3$), 3.52 (1H, s, 2'-OH), 3.10 (2H, m, H-11β+H-8α), 2.94 (1H, m, H-10α), 2.59 (2H, m, H-8β+H-10α), 2.38 (1H, dd, J=14.0 and 6.7, H-11α), 2.24 and 1.92 (2H, 2d, J$_{AB}$=16.2, C$\underline{H}_2$CO$_2$), 2.0 (3H, m, H-6A and CH$_2$-c), 1.92 (1H, m, H-6B), 1.76 (2H, m, CH$_2$-7), 1.63 (5H, m, CH$_2$-b and CH$_3$-f), 1.5–1.1 (6H, m, 3×CH$_2$), 1.18 (6H, 2s, 2×CH$_3$).

EXAMPLE 54

Preparation of (2'R)-4'-Hexyl-4'-demethyl-homoharringtonine

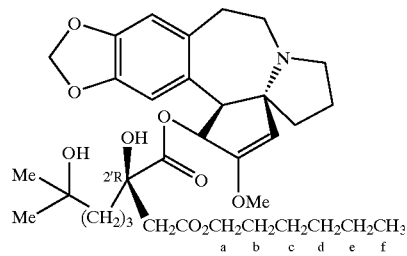

Sodium hydride 60% (6.6 mg, 0.16 mmol) was added to a solution of homoharringtonine (300 mg, 0.55 mmol) in n-hexanol (3 ml) and the resulting mixture was stirred at ambient temperature for 1.5 hours under argon. After adjusting to pH 1.9 by addition of hydrochloric acid 0.1N (5 ml) the aqueous layer was washed with ether (3×10 ml). The resulting aqueous layer was alkalinized to pH 9.5 with ammonia 25% and was extracted with dichloromethane (6×10 ml). The combined organic layers were dried over magnesium sulfate and evaporated to dryness. The crude product thus obtained was purified by phase-reversed chromatography (octadecylsilane 12 μm (135 g), buffer pH 3/methanol, 30:70). After removal of methanol in vacuo and ajusting to pH 1.9 by addition of hydrochloric acid 0.1N (5 ml), the resulting aqueous layer was washed with ether (3×5 ml), alkalinized to pH 9.5 with ammonia 25% and extracted with dichloromethane (6×10 ml). The combined organic layers were dried over magnesium sulfate and evaporated to dryness to provide the expected compound (158 mg; 47%). The product thus obtained showed the following characteristics:

$^1$H NMR 400 MHz (CDCl$_3$) (δ ppm, J Hz): 6.62 (1H, s, H-17), 6.55 (1H, s, H-14), 5.98 (1H, d, J$_{3-4}$=9.8, H-3), 5.86 (2H, s, OCH$_2$O), 5.05 (1H, s, H-1), 4.0 and 3.91 (2H, 2m, C$\underline{H}_2$-a), 3.78 (1H, d, J$_{4-3}$=9.9, H-4), 3.68 (3H, s, OCH$_3$), 3.52 (1H, s, 2'-OH), 3.10 (2H, m, H-11β+H-8α), 2.94 (1H, m, H-10α), 2.60 (2H, m, H-8β+H-10α), 2.39 (1H, dd, J=13.8 and 6.7, H-11α), 2.25 and 1.92 (2H, 2d, J$_{AB}$=16.2, C$\underline{H}_2$CO$_2$), 2.17 (1H, m, H-6$_A$), 1.92 (1H, m, H-68), 1.76 (2H, m, CH$_2$-7), 1.56 (2H, m, CH$_2$-b), 1.5–1.1 (12H, m, CH$_2$-c,d,e and 3×CH$_2$), 1.19 (3H, s, CH$_3$), 1.18 (3H, s, CH$_3$), 0.89 (3H, t, J=6.83, CH$_3$-f).

EXAMPLE 55

Preparation of (2'R)-4'-(but-2-Enyl)-4'-demethyl-harringtonine

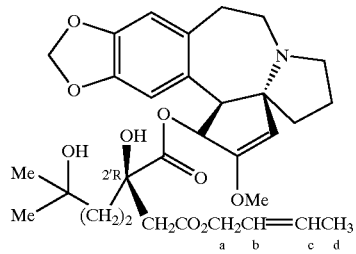

Sodium hydride 60% (7.4 mg, 0.188 mmol) was added to a solution of harringtonine (250 mg, 0.471 mmol) in crotyl alcohol (2.5 ml) and the resulting mixture was stirred at ambient temperature for 2.5 hours. After adjusting to pH 4 by addition of hydrochloric acid 1 N the aqueous layer was washed with ether (3×10 ml). The resulting aqueous layer was alkalinized with ammonia 25% and was extracted with dichloromethane (3×10 ml). The combined organic layers were dried over magnesium sulfate and evaporated to dryness (268 mg crude, 99.50%). The crude product thus obtained was purified by phase-reversed chromatography (octadecylsilane 12 μm (100 g), buffer pH 3/methanol, 65:35 to 60:40). After removal of methanol in vacuo the resulting aqueous layer was alkalinized to pH 9.2 with ammonia 25% and extracted with dichloromethane (6×15 ml). The combined organic layers were dried over magnesium sulfate and evaporated to dryness to provide the expected compound, 157 mg; 58.5%). The product thus obtained showed the following characteristics:

$^1$H NMR 400 MHz (CDCl$_3$) (δ ppm, J Hz): 6.62 (1H, s, H-17), 6.55 (1H, s, H-14), 5.98 (1H, d, J$_{3-4}$=9.7, H-3), 5.85 (2H, s, OCH$_2$O), 5.75 (1H, dq, J$_{c-b}$=15.3, J$_{c-d}$=6.4, H-c), 5.55 (1H, dtq, J$_{b-c}$=15.3, J$_{b-a}$=6.4, J$_{b-d}$=1.7, H-b), 5.07 (1H, s, H-1), 4.47 and 4.35 (2H, 2dd, J$_{AB}$=12.3, J$_{a-b}$=6.5, CH$_2$-a), 3.78 (1H, d, J$_{4-3}$=9.6, H-4), 3.70 (3H, s, OCH$_3$), 3.63 (1H, s, 2'-OH), 3.10 (2H, m, H-11β+H-8α), 2.95 (1H, m, H-10α), 2.58 (2H, m, H-8β+H-10α), 2.398 (1H, m, H-11α), 2.28 and 1.89 (2H, 2d, J$_{AB}$=16.4, CH$_2$CO$_2$), 2.01 (1H, m, H-6$_A$), 1.89 (1H, m, H-6B), 1.76 (2H, m, CH$_2$-7), 1.72 (3H, dd, J$_{d-c}$=6.6, J$_{d-b}$=1.2, CH$_3$-d), 1.60 (3H, m, CH$_2$), 1.25 (1H, m, CH$_2$), 1.17 (3H, s, CH$_3$), 1.14 (3H, s, CH$_3$).

EXAMPLE 56

Preparation of 4-(2-Butenyl)(2R)-2-hydroxy-2-(4-hydroxy-4-methylpentyl)succinate of (−)-Drupacine

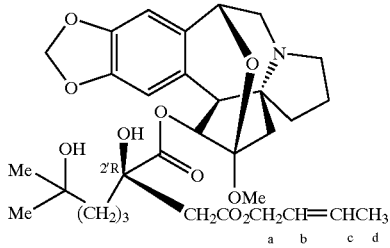

Sodium hydride 60% (14 mg, 0.358 mmol) was added to a solution of 4-methyl (2R)-2-hydroxy-2-(4-hydroxy-4-methylpentyl)succinate of (−)-drupacine (500 mg, 0.8 mmol) in crotyl alcohol (4.5 ml) and the resulting mixture was stirred at ambient temperature for 2.5 hours. After adjusting to pH 4' by addition of hydrochloric acid 1 N the aqueous layer was washed with ether (3×10 ml). The resulting aqueous layer was alkalinized with ammonia 25% and was extracted with dichloromethane (3×10 ml). The combined organic layers were dried over magnesium sulfate and evaporated to dryness (366 mg crude, 74%). The crude product thus obtained was purified by phase-reversed chromatography (octadecylsilane 12 μm (100 g), buffer pH 3/methanol, 57:43). After removal of methanol in vacuo the resulting aqueous layer was alkalinized to pH 10.6 with ammonia 25% and extracted with dichloromethane (6×10 ml). The combined organic layers were dried over magnesium sulfate and evaporated to dryness to provide the expected compound (132 mg; 27%). The product thus obtained showed the following characteristics:

$^1$H NMR 400 MHz (CDCl$_3$) (δ ppm, J Hz): 6.65 (1H, s, H-17*), 6.46 (1H, s, H-14*), 5.90 and 5.87 (2H, 2d, J$_{AB}$=1.5, OCH$_2$O), 5.79 (1H, m, H-c), 5.57 (1H, m, H-b), 5.23 (1H, d, J$_{3-4}$=9.6, H-3), 4.86 (1H, d, J$_{11-10A}$=4.3, H-11), 4.56 and 4.45 (2H, 2dd, J$_{AB}$=12.3, J$_{a-b}$=6.6, CH$_2$-a), 3.56 (1H, d, J$_{4-3}$=9.6, H-4), 3.51 (1H, s, 2'-OH), 3.41 (3H, s, OCH$_3$), 3.12 (1H, dd, J$_{AB}$=13.2, J$_{10A-11}$=4.9, H-10$_A$), 3.08 (1H, m, H-8α), 2.97 (1H, d, J$_{AB}$=13.1, H-10$_B$), 2.67 (1H, d, J$_{AB}$=14.0, H-1A), 2.40 (1H, ~q, J=8.7, H-8α), 2.29 and 1.96 (2H, 2d, J$_{AB}$=16.4, CH$_2$CO$_2$), 2.19 (1H, m, H-6$_A$), 2.04 (1H, m, H-6B), 1.9–1.1 (8H, m, CH$_2$-7 and 3×CH$_2$), 1.73 (3H, dd, J$_{d-c}$=6.5, J$_{d-b}$=1.1, CH$_3$-d), 1.55 (1H, d, J$_{AB}$=14.0, H-1$_B$) 1.18 (3H, s, CH$_3$), 1.16 (3H, s, CH$_3$).

EXAMPLE 57

Preparation of 4-(hexa-2,4Dienyl) (2R)-2-hydroxy-2-(4-hydroxy-4-methylpentyl)succinate of (−)-Drupacine

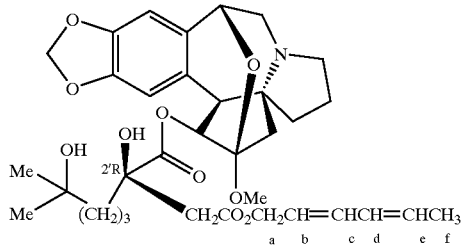

Sodium hydride 60% (6.8 mg, 0.272 mmol) was added to a solution of 4-methyl (2R)-2-hydroxy-2-(4-hydroxy-4-methylpentyl)succinate of (−)-drupacine (200 mg, 0.34 mmol) in hexa-2,4-dienol (2 ml) and the resulting mixture was stirred at ambient temperature for 2 hours. After adjusting to pH 1.5 by addition of hydrochloric acid 1 N (7 ml) the aqueous layer was washed with ether (3×10 ml). The resulting aqueous layer was alkalinized to pH 9.5 with ammonia 25% and was extracted with dichloromethane (5×10 ml). The combined organic layers were dried over magnesium sulfate and evaporated to dryness (182 mg crude, 86%). The crude product thus obtained was purified by phase-reversed chromatography (octadecylsilane 12 μm (100 g), buffer pH 3/methanol, 40:60). After removal of methanol in vacuo the resulting aqueous layer was adjusted to pH 1.5 with hydrochloric acid 1N, washed with ether (3×10 ml), alkalinized to pH 10.6 with ammonia 25% and extracted with dichloromethane (5×10 ml). The combined organic layers were dried over magnesium sulfate and evaporated to dryness to provide the expected compound (50 mg; 23.5%). The product thus obtained showed the following characteristics:

$^1$H NMR 400 MHz (CDCl$_3$) (δ ppm, J Hz): 6.65 (1H, s, H-17*), 6.46 (1H, s, H-14*), 6.26 (1H, dd, J$_{c-b}$=15.2, J$_{c-d}$=10.5, H-c), 6.05 (1H, m, H-d) 5.88 and 5.85 (2H, 2d, J$_{AB}$=1.3, OCH$_2$O), 5.76 (1H, m, H-e), 5.60 (1H, m, H-b), 5.23 (1H, d, J$_{3-4}$=9.6, H-3), 4.86 (1H, d, J$_{11-10A}$=4.3, H-11), 4.63 and 4.52 (2H, 2dd, J$_{AB}$=12.9, J$_{a-b}$=6.6, CH$_2$-a), 3.55 (1H, d, J$_{4-3}$=9.6, H4), 3.51 (1H, s, 2'-OH), 3.41 (3H, s, OCH$_3$), 3.11 (1H, dd, J$_{AB}$=13.3, J$_{11A-11}$=4.9, H-10$_A$), 3.06 (1H, m, H-8α), 2.96 (1H, d, J$_{AB}$=13.1, H-10$_B$), 2.66 (1H, d, J$_{AB}$=14.0, H-1A), 2.42 (1H, m, H-8α), 2.30 and 1.96 (2H, 2d, J$_{AB}$=16.5, CH$_2$CO$_2$), 2.19 (1H, m, H-6$_A$), 2.05 (1H, m, H-6$_B$), 1.77 (2H, m, CH$_2$-7) and (3H, d, J$_{f-e}$=6.2, CH$_3$-f), 1.6–1.1 (6H, m, 3×CH$_2$), 1.55 (1H, d, J$_{AB}$=14.0, H-1$_B$), 1.17 (3H, s, CH$_3$), 1.16 (3H, s, CH$_3$).

EXAMPLE 58

Preparation of (2'R)-4"-Fluoro-4"-deoxy-homoharringtonine

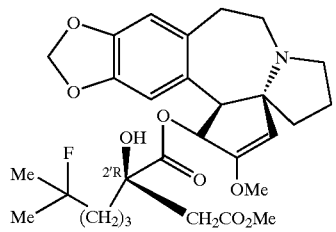

To a stirred solution of homoharringtonine (20 mg, 0.037 mmol) in dry dichloromethane (1.5 ml) under nitrogen was slowly added DAST (25 µl, 0.185 mmol) at −40° C. After stirring at −20° C. for 3 hours, was added a saturated sodium hydrogen carbonate solution (2 ml), the resulting aqueous layer was extracted with dichloromethane (3×5 ml) and the combined organic layers were washed with water (5 ml), with brine (5ml), were dried over magnesium sulfate and evaporated to dryness. The resulting crude product (13 mg) was purified by column chromatography (silica 15–40 µm (0.2 g), dichloromethane then dichloromethane/methanol, 98:2) to provide the expected compound (4 mg, 20%). The product thus obtained showed the following characteristics:

$^1$H NMR 400 MHz (CDCl$_3$) (δ ppm, J Hz): 6.63 (1H, s, H-17), 6.54 (1H, s, H-14), 6.08 (1H, d, J$_{3-4}$=9.3, H-3), 5.87 and 5.86 (2H, 2d J$_{AB}$=1.4, OCH$_2$O), 5.04 (1H, s, H-1), 3.77 (1H, d, J$_{4-3}$=9.8, H-4), 3.67 (3H, s, OCH$_3$), 3.57 (3H, s, OCH$_3$), 3.39 (1H, s, 2'-OH), 3.10 (2H, m, H-11βH-8α), 2.94 (1H, m, H-10α), 2.60 (2H, m, H-8β+H-10β), 2.38 (1H, m, J=14 and 6.8, H-11α), 2.26 and 1.89 (2H, 2d, J$_{AB}$=16.4, CH$_2$CO$_2$), 2.02 (1H, m, H-6$_A$), 1.91 (1H, m, H-6B), 1.75 (2H, m, CH$_2$-7), 1.6–1.2 (6H, m, 3×CH$_2$), 1.34 (3H, d, J$_{H-F}$=21.4, CH$_3$), 1.28 (3H, d, J$_{H-F}$=21.4, CH$_3$).

EXAMPLE 59

Preparation of (2'R)-3"-Fluoro-3"-deoxy-harringtonine

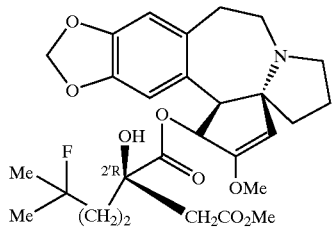

To a stirred solution of harringtonine (50 mg, 0.094 mmol) in dry dichloromethane (3.5 ml) under nitrogen was slowly added DAST (62 µl, 0.47 mmol) at −40° C. After stirring at −20° C. for 3 hours, was added a saturated sodium hydrogen carbonate solution (5 ml), the resulting aqueous layer was extracted with dichloromethane (3×5 ml). The combined organic layers were washed with water (5 ml), with brine (5ml), dried over magnesium sulfate and evaporated to dryness. The crude product thus obtained was purified by phase-reversed chromatography (octadecylsilane 12 µm (135 g), buffer pH 3/methanol, 45–65). After removal of methanol in vacuo the resulting aqueous layer was adjusted to pH 8.6 with ammonia 25% and extracted with dichloromethane (5×10 ml). The combined organic layers were dried over magnesium sulfate and evaporated to dryness to provide the expected compound (11 mg; 22%). The product thus obtained showed the following characteristics:

$^1$H NMR 400 MHz (CDCl$_3$) (δ ppm, J Hz): 6.63 (1H, s, H-17), 6.54 (1H, s, H-14), 6.01 (1H, d, J$_{3-4}$=9.8, H-3), 5.87 and 5.856 (2H, 2d J$_{AB}$=1.4, OCH$_2$O), 5.05 (1H, s, H-1), 3.77 (1H, d, J$_{4-3}$=9.8, H-4), 3.67 (3H, s, OCH$_3$), 3.57 (3H, s, OCH$_3$), 3.54 (1H, s, 2'-OH), 3.10 (2H, m, H-11β+H-8α), 2.94 (1H, m, H-10α), 2.60 (2H, m, H-8β+H-10α), 2.38 (1H, m, J=14 and 6.8, H-11α), 2.29 and 1.90 (2H, 2d, J$_{AB}$=16.6, CH$_2$CO$_2$), 2.03 (1H, m, H-6$_A$), 1.91 (1H, m, H-6$_B$), 1.75 (2H, m, CH$_2$-7), 1.7–1.1 (4H, m, 2×CH$_2$), 1.30 (3H, d, J$_{H-F}$=21.4, CH$_3$), 1.29 (3H, d, J$_{H-F}$=21.4, CH$_3$).

EXAMPLE 60

Preparation of (2'S)-4"-Chloro-4"-deoxy-epi-homoharringtonine

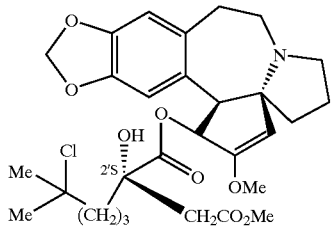

To a stirred solution of epi-homoharringtonine (100 mg, 0.18 mmol) in dry chloroform (2 ml) under nitrogen was added SOCl2 (131 µl, 1.8 mmol). After stirring at ambient temperature for 2 hours, was added a saturated sodium hydrogen carbonate solution (5 ml), the resulting aqueous layer was extracted with dichloromethane (3×5 ml) and the combined organic layers were dried over magnesium sulfate and evaporated to dryness to provide the expected compound (104 mg crude, 100%). The product thus obtained showed the following characteristics:

$^1$H NMR 400 MHz (CDCl$_3$) (δ ppm, J Hz): 6.64 (1H, s, H-17), 6.59 (1H, s, H-14), 5.95 and 5.87 (2H, 2d J$_{AB}$=1.2, OCH$_2$O), 5.94 (1H, d, J$_{3-4}$=9.8, H-3), 5.04 (1H, s, H-1), 3.78 (1H, d, J$_{4-3}$=9.7, H-4), 3.67 (3H, s, OCH$_3$), 3.66 (3H, s, OCH$_3$), 3.58 (1H, s, 2'-OH), 3.11 (2H, m, H-11µ+H-8α), 2.93 (1H, m, H-10α), 2.62 and 2.54 (2H, 2d, J$_{AB}$=16.5, CH$_2$CO$_2$), 2.60 (2H, m, H-8α+H-10α), 2.39 (1H, m, J=13.9 and 6.6, H-11α), 2.02 (1H, m, H-6$_A$), 1.90 (1H, m, H-6$_B$), 1.76 (2H, m, CH$_2$-7), 1.7–0.7 (6H, m, 3×CH$_2$), 1.53 (3H, s, CH$_3$), 1.52 (3H, s, CH$_3$).

EXAMPLE 61

Preparation of 4-Methyl (2R)-2-hydroxy-2-(4-methyl-pent-3-enyl)succinate of (−)-Cephalotaxine

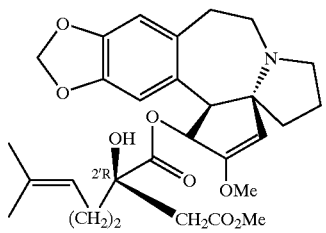

To a stirred solution of homoharringtonine (100 mg, 0.18 mmol) in dry pyridine (2 ml) under nitrogen was added POCl3 (170 µl, 1.8 mmol) at −5° C. After stirring at −5° C. for 20 hours and adjusting to pH 0.5 by addition of hydrochloric acid 50% (9 ml) the aqueous layer was washed with ether (3×10 ml). The resulting aqueous layer was alkalinized to pH 9.5 with ammonia 25% and was extracted with dichloromethane (5×10 ml). The combined organic layers were dried over magnesium sulfate and evaporated to dryness. The crude product thus obtained was purified by phase-reversed chromatography (octadecylsilane 12 µm (100 g), buffer pH 3/methanol, 45:55). After removal of methanol in vacuo the resulting aqueous layer was adjusted to pH 1.5 with hydrochloric acid 1N, washed with ether (3×10 ml), alkalinized to pH 10.6 with ammonia 25% and extracted with dichloromethane (5×10 ml). The combined organic layers were dried over magnesium sulfate and evaporated to dryness to provide the expected compound (20 mg; 21%). The product thus obtained showed the following characteristics:

$^1$H NMR 400 MHz (CDCl$_3$) (δ ppm, J Hz): 6.62 (1H, s, H-17), 6.54 (1H, s, H-14), 6.0 (1H, d, J$_{3-4}$=9:8, H-3), 5.88 and 5.83 (2H, 2d J$_{AB}$=1.4, OCH$_2$O), 5.06 (1H, s, H-1), 5.01 (1H, m, =CH), 3.78 (1H, d, J$_{4-3}$=9.8, H-4), 3.68 (3H, s, OCH$_3$), 3.58 (3H, s, OCH$_3$), 3.51 (1H, s, 2'-OH), 3.14 (2H, m, H-11β+H-8α), 2.96 (1H, m, H-10α), 2.39 (2H, m, H-8µ+H-10β), 2.39 (1H, m, J=14.1 and 6.7, H-11α), 2.27 and 1.89 (2H, 2d, J$_{AB}$=16.4, CH$_2$CO$_2$), 2.1–1.9 (3H, m, CH$_2$-6+CH$_2$), 2.1–1.9 (3H, m, CH$_2$-7+CH$_2$), 1.66 (3H, s, CH$_3$), 1.56 (3H, s, CH$_3$), 1.42 (2H, m, CH$_2$).

EXAMPLE 62

Preparation of (2'R)-4'-(4-Pentenyl)-4'-demethyl-homoharringtonine

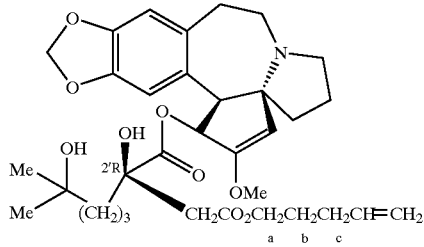

Sodium hydride 60% (7.1 mg, 0.177 mmol) was added to a solution of homoharringtonine (322 mg, 0.590 mmol) in 4-penten-1-ol (3.2 ml) and the resulting mixture was stirred at ambient temperature for 2 hours under argon. After adjusting to pH 1.9 by addition of hydrochloric acid 0.1N (11 ml), the aqueous layer was washed with ether (3×6 ml). The resulting aqueous layer was alkalinized with ammonia 25% (five drops) and was extracted with dichloromethane (6×10 ml). The combined organic layers were dried over magnesium sulfate and evaporated to dryness (230 mg crude, 65%). The crude product thus obtained was purified by phase-reversed chromatography (octadecylsilane 12 µm (135 g), buffer pH 3/methanol, 50:50). After removal of methanol in vacuo the resulting aqueous layer was washed with ether (10 ml) and alkalinized to pH 9.5 with ammonia 25% (five drops) and extracted with dichloromethane (6×10 ml). The combined organic layers were dried over magnesium sulfate and evaporated to dryness to provide the expected compound (149 mg; 42%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, J$_{3-4}$=9.8, H-3), 5.85 (2H, s, OCH$_2$O), 5.80 (1H, m, CH=), 5.05 (1H, s, H-1), 5.03 (2H, m, =CH2), 3.98 (2H, m, CH$_2$-a), 3.77 (1H, d, J$_{4-3}$=9.8, H-4), 3.68 (3H, s, OCH$_3$), 3.52 (1H, s, 2'-OH), 3.12 (2H, m, H-11β+H-8α), 2.94 (1H, dt, J=11.2 and 6.9, H-10), 2.58 (2H, m, H-8µ+H-10β), 2.38 (1H, dd, J$_{AB}$=14.0, J=6.7, H-11α), 2.25 and 1.92 (2H, 2d, J$_{AB}$=16.3, CH$_2$CO$_2$), 2.09 (2H, q, J=7.2, CH$_2$-c), 2.03 (1H, m, H-6A), 1.90 (1H, m, H-6$_B$), 1.75 (2H, m, CH$_2$-7), 1.67 (2H, qt, J=7.4, CH$_2$-b), 1.50–1.30 (6H, m, 3×CH$_2$), 1.29 (1H, s, 4"-OH), 1.18 and 1.19 (6H, 2s, 2×CH$_3$).

EXAMPLE 63

Preparation of (2'R)-4'-(Dimethylamino-ethyl)-4'-demethyl-homoharring-tonine

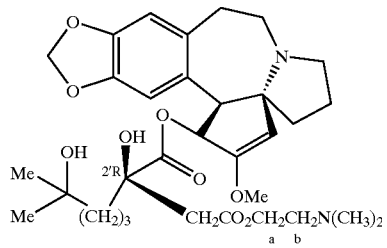

Sodium hydride 60% (5.8 mg, 0.145 mmol) was added to a solution of homoharringtonine (400 mg, 0.733 mmol) in N,N-dimethylethanol (4 ml) and the resulting mixture was stirred at ambient temperature for 2 hours under argon. After adjusting to pH 1.5 by addition of hydrochloric acid 0.1N (20 ml), the aqueous layer was washed with ether (3×8 ml). The resulting aqueous layer was alkalinized with ammonia 25% (pH=8–9) and was extracted with dichloromethane (6×10 ml). The combined organic layers were dried over magnesium sulfate and evaporated to dryness (quantitative). The crude product thus obtained was purified by phase-reversed chromatography (octadecylsilane 12 µm (135 g), buffer pH 3/methanol, 100:0 then 95:5; 90:10; 80:20). After removal of methanol in vacuo the resulting aqueous layer was washed with ether (10 ml) and alkalinized to pH 9.5 with ammonia 25% and extracted wits dichloromethane (6×10 ml). The combined organic layers were dried over magnesium sulfate and evaporated to dryness to provide the expected compound (266 mg; 60%). The product thus obtained showed the following characteristics:

$^1$H NMR 400 MHz (CDCl$_3$) (δ ppm, J Hz): 6.60 (1H, s, H-17), 6.54 (1H, s, H-14), 6.02 (1H, d, J$_{3-4}$=9.8, H-3), 5.84 (2H, s, OCH$_2$O), 5.04 (1H, s, H-1), 4.43 (1H, ddd, J=11.8, J=8.0, J=4.0, H-act), 3.79 (1H, d, J$_{4-3}$=9.8, H4), 3.74 (1H, m, H-aβ), 3.67 (3H, s, OCH$_3$), 3.12 (2H, m, H-11β+H-8α), 2.94 (1H, dt, J=11.2 and 6.9, H-10□), 2.58 (2H, m, H-8□+H-10□), 2.49 (1H, ddd, J=12.6, J=8.0, J=4.3, H-b□), 2.37 (1H, dd, J$_{AB}$=14.3, J=6.7, H-11α), 2.34 (1H, m, H-6$_A$), 2.22 (6H, s, N(CH$_3$)$_2$), 2.22 and 2.11 (2H, 2d, J$_{AB}$=15.5, CH$_2$CO$_2$), 2.03 (1H, m, H-6$_B$), 1.89 (1H, ddd, J=12.1, J=7.7, J=4.3, H-bβ), 1.75 (2H, m, CH$_2$-7), 1.50–1.20 (7H, m, 3×CH$_2$ and 4"-OH), 1.19 and 1.18 (6H, 2s, 2×CH$_3$).

EXAMPLE 64

Preparation of (2'R)-4'-Nonyl-4'-demethyl-homoharringtonine

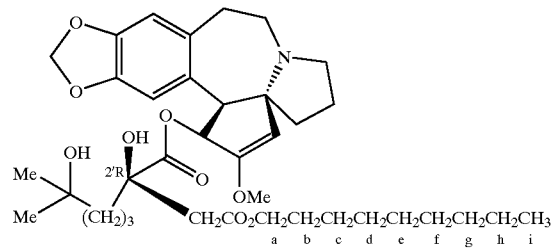

Sodium hydride 60% (8.9 mg, 0.223 mmol) was added to a solution of homoharringtonine (405 mg, 0.742 mmol) in n-nonanol (4 ml) and the resulting mixture was stirred at ambient temperature for 3 hours under argon. After adjusting to pH 1.3 by addition of hydrochloric acid 0.1N (13 ml), the aqueous layer was washed with petroleum ether (8 ml) and the resulting organic layer was extracted with hydrochloric acid 0.1 N (5 ml). This was repeated an other time. The combined aqueous layers were washed with ether (8 ml) then were alkalinized to pH 9.6 with ammonia 25% (fifteen drops) and were extracted with dichloromethane (6×8 ml). The combined organic layers were dried over magnesium sulfate and evaporated to dryness (400 mg crude, 82%). The crude product thus obtained was purified by phase-reversed chromatography (octadecylsilane 12 μm (135 g), buffer pH 3/methanol, 20:80). After removal of methanol in vacuo the resulting aqueous layer was alkalinized to pH 9.7 with ammonia 25% and extracted with dichloromethane (6×10 ml). The combined organic layers were dried over magnesium sulfate and evaporated to dryness to provide the expected compound (256 mg; 52%). The product thus obtained showed the following characteristics:

$^1$H NMR 400 MHz (CDCl$_3$) (δ ppm, J Hz): 6.62 (1H, s, H-17), 6.54 (1H, s, H-14), 5.98 (1H, d, $J_{3-4}$=9.8, H-3), 5.86 (2H, s, OCH$_2$O), 5.05 (1H, s, H-1), 4.00 and 3.91 (2H, 2m, $\underline{CH}_2$-a), 3.78 (1H, d, $J_{4-3}$=9.8, H-4), 3.68 (3H, s, OCH$_3$), 3.52 (1H, s, 2'-OH), 3.10 (2H, m, H-11β+H-8α), 2.95 (1H, m, H-10α), 2.60 (2H, m, H-8β+H-10β), 2.38 (1H, dd, J=14.1 and 6.7, H-11α), 2.24 and 1.92 (2H, 2d, $J_{AB}$=16.3, $\underline{CH}_2$CO$_2$), 2.03 (1H, m, H-6$_A$), 1.92 (1H, m, H-6$_B$), 1.77 (2H, m, CH$_2$-7), 1.56 (2H, m, CH$_2$-b), 1.50–1.22 (16H, m, CH$_2$-c, d, e, f, g, h and 3×CH$_2$), 1.19 (6H, s, 2×CH$_3$), 0.88 (3H, t, J=6.8, CH$_3$-i).

EXAMPLE 65

Preparation of (2'R)-4'-Pentyl-4'-demethyl-homoharringtonine

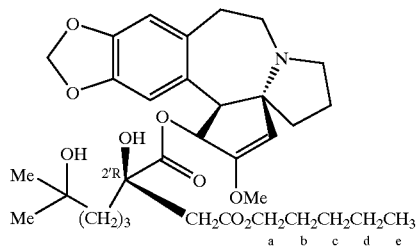

Sodium hydride 60% (10.0 mg, 0.250 mmol) was added to a solution of homoharringtonine (416 mg, 0.762 mmol) in n-pentanol (4.2 ml) and the resulting mixture was stirred at ambient temperature for 2 hours under argon. After adjusting to pH 1.8 by addition of hydrochloric acid 0.1N (14 ml), the aqueous layer was washed with ether (3×8 ml). The resulting aqueous layer was alkalinized with ammonia 25% (pH=9.5) and was extracted with dichloromethane (6×10 ml). The combined organic layers were dried over magnesium sulfate and evaporated to dryness (339 mg crude, 74%). The crude product thus obtained was purified by phase-reversed chromatography (octadecylsilane 12 μm (130 g), buffer pH 3/methanol, 40:60). After removal of methanol in vacuo the resulting aqueous layer was alkalinized to pH 9.7 with ammonia 25% and extracted with dichloromethane (6×10 ml). The combined organic layers were dried over magnesium sulfate and evaporated to dryness to provide the expected compound (274 mg, 60%). The product thus obtained showed the following characteristics:

$^1$H NMR 400 MHz (CDCl3) (δ ppm, J Hz): 6.62 (1H, S, H-17), 6.55 (1H, S, H-14), (1H, d, $J_{3-4}$=9.7, H-3), 5.86 (2H, S, OCH$_2$O), 5.05 (1H, S, H-1), 4.00 and 3.92 (2H, 2m, $\underline{CH}_2$-a), 3.78 (1H, d, $J_{4-3}$=9.2, H4), 3.68 (3H, S, OCH$_3$), 3.53 (1H, S, 2'-OH), 3.12 (2H, m, H-11β+H-8α), 2.96 (1H, m, H-10α), 2.61 (2H, m, H-8μ+H-10α), 2.41 (1H, m, H-11α), 2.25 and 1.95 (2H, 2d, $J_{AB}$=16.2, $\underline{CH}_2$CO$_2$), 2.03 (1H, m, H-6$_A$), 1.92 (1H, m, H-6$_B$), 1.78 (2H, m, CH$_2$-7), 1.57 (2H, m, CH$_2$-b), 1.50–1.22 (10H, m, CH$_2$-c, d and 3×CH$_2$), 1.19 (6H, s, 2×CH$_3$), 0.90 (3H, t, J=6.9, CH$_3$-e).

Biological Data

1—Materials and Methods

Structural analogues of harringtonines described in this invention were tested on K562 cell line, derived from chronic myeloid leukemia cells in blastic transformation (bcr-abl positive). The cell line was purchased from ATCC (American Tissue Culture Collection) and grown in RPMI medium supplemented with 10% heat-inactivated fetal calf serum, 2 mmol/L glutamine, 50 IU/mol penicillin and 50 IU/mol streptomycin. All tested products were initially dissolved in 2N HCl (pH=2), supplemented with ultrasound treatment during 1 h. Working concentrations were made by dilution in culture medium (pH around 7). Cells in exponential growth phase were placed into 96-microwell plates in concentration 3×10$^4$/mL (total volume 200 μL/well) and incubated with drugs for 72 h at 37° C. in 5% CO$_2$ humidified atmosphere. Following incubation, 28 μL of MTT solution (Sigma, St. Louis, Mo.) was added to each well. During the following 6 h of incubation at 37° C., the purple formazan product was formed by conversion of the yellow MTT salt in the mitochondria of the viable cells. The resulting precipitate was dissolved in DMSO and the amount of converted MTT was quantified in an ELISA reader (MR 5000, Dynatech). Each product was tested in triplicate (3×8 wells). Every test contained at least one plate with HHT as control, added in the same concentration as the tested products.

2—Results

The following table represents the results of some examples of the compounds according to the present invention in K562 cell line compared to the homoharringtonine, the harringtonine and the cephalotaxine.

| NAME | EXAMPLE. # | IC$_{50}$ |
| --- | --- | --- |
| O-HEXADIENYL-DMHO[1] | 43 | 3.5 |
| O-HEXYL-DMHO | 54 | 5 |
| O-METALLYL-DMHO | 41 | 8.5 |
| O-HEXENYL-DMHO | 53 | 8.5 |
| O-HEXADIENYL-DMHD | 57 | 9 |
| O-BUTYNYL-DMHO | 42 | 10.5 |
| O-CROTYL-DMHO | 37 | 12.5 |
| O-BUTYL-DMHO | 50 | 1.3 |
| O-CROTYL-DMHD[2] | 56 | 13.5 |
| FLUORODESOXYHARRINGTONINE | 59 | 13.5 |
| O-CROTYL-DMHA[3] | 55 | 14 |
| HOMOHARRINGTONINE | | 14 |
| O-ALLYL-DMHO | 40 | 14.5 |
| DESHYDRO-HHT | 61 | 17.5 |
| THIOTERBUTYL-DMHO | 36 | 20 |
| O-PROPYL-DMHO | 51 | 22.5 |
| O-ISOBUTYL-DMHO | 52 | 24 |
| O-SENECYL-DMHO | 39 | 28 |
| HARRINGTONINE (HHT)[4] | | 30 |
| O-ETHYL-DMHO | 25 | 41 |
| THIOISOPROPYL-DMHO | 34 | 50 |
| THIOMETHYL-DMHO | 30 | 50 |

-continued

| NAME | EXAMPLE. # | $IC_{50}$ |
|---|---|---|
| O-METHYLCYCLOPROPYL-DMHO | 49 | 70 |
| O-ISOPROPYL-DMHO | 27 | 80 |
| THJOETHYL-DMHO | 32 | 80 |
| O-TRIFLUOROETHYL-DMHO | 48 | 100 |
| CEPHALOTAXINE (CTX)[5] | | 2000 |

[1]DMHO means 4'-demethyl-homoharringtonine
[2]DMHD means 4'-demethyl-4"-hydroxydrupangtonine
[3]DMHA means 4'-demethyl-harringtonine
[4]HHT means homoharringtonine (natural or semi-synthetic source)
[5]CTX means cephalotaxines (natural source)

The same method as above was used to test the O-hexadienyl-DMHO (example 43) on $K562_{MRP}$, a subline of K562 line exhibiting a strong resistance to 50 ng/mL of homoharringtonine. The $IC_{50}$ of the O-hexadienyl-DMHO (example 43) was 16 ng/mL, i.e. a value not significantly different from homoharringtonine itself in non resistant version of K562 line (cf. above table)

What is claimed is:

1. A compound selected from the group consisting of a compound of formula (I)

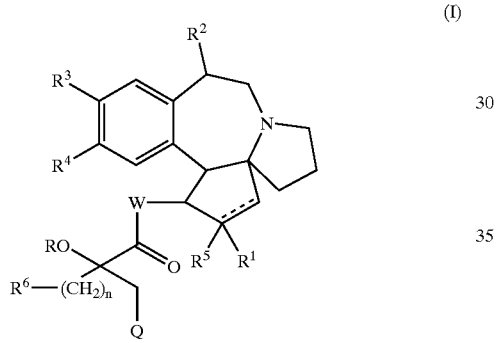

(I)

wherein,
W=O or NH,
Q=COZ—$R^8$,
Z=O, S, or NH, and

when W represents O, the dotted line forms a double bond, $R^1$ is null, $R^2$ is H, $R^3$ and $R^4$ represent —O—$CH_2$—O—, $R^5$=OMe, Z=O, R=H, $R^6$=—(C—Y)$Me_2$, Y=OH and n=3, or

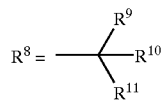

or Z—$R^8$ is $NR^{12}R^{13}$, $R^{12}$ and $R^{13}$ representing respectively $R^9$ and $R^{10}$, wherein $R^9$ and $R^{10}$ are independently H, unsubstituted $C_1$–$C_{30}$ alkyl, unsubstituted $C_3$–$C_{30}$ cycloalkyl, unsubstituted aryl, unsubstituted aryl-($C_1$–$C_{30}$)-alkyl, unsubstituted $C_2$–$C_{30}$ alkenyl, unsubstituted $C_2$–$C_{30}$ alkynyl, unsubstituted $C_1$–$C_{30}$ trihalogenoalkyl, unsubstituted $C_1$–$C_{30}$ alkylamino-($C_1$–$C_{30}$)alkyl, unsubstituted $C_1$–$C_{30}$ dialkylamino ($C_1$–$C_{30}$)-alkyl, or unsubstituted amino-($C_1$–$C_{30}$)-alkyl, or

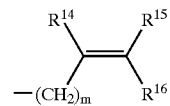

where $R^{14}$, $R^{15}$ and $R^{16}$ are independently H, halogen, unsubstituted $C_1$–$C_{30}$ alkyl, unsubstituted $C_3$–$C_{30}$ cycloalkyl, unsubstituted aryl, unsubstituted aryl-($C_1$–$C_{30}$)-alkyl, unsubstituted $C_2$–$C_{30}$ alkenyl or unsubstituted $C_2$–$C_{30}$ alkynyl, unsubstituted $C_1$–$C_{30}$ trihalogenoalkyl, m is 0 to 4, and $R^{11}$ is unsubstituted $C_2$–$C_{30}$ alkyl, unsubstituted $C_3$–$C_{30}$ cycloalkyl, unsubstituted aryl, unsubstituted aryl-($C_1$–$C_{30}$)-alkyl, unsubstituted $C_2$–$C_{30}$ alkenyl, unsubstituted $C_2$–$C_{30}$ alkynyl, unsubstituted $C_1$–$C_{30}$ trihalogenoalkyl, unsubstituted $C_1$–$C_{30}$ alkylamino-($C_1$–$C_{30}$)alkyl, unsubstituted $C_1$–$C_{30}$ dialkylamino ($C_1$–$C_{30}$)-alkyl, or unsubstituted amino-($C_1$–$C_{30}$)-alkyl, or

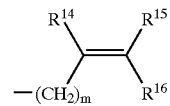

where $R^{14}$, $R^{15}$ and $R^{16}$ are independently H, halogen, unsubstituted $C_1$–$C_{30}$ alkyl, unsubstituted $C_3$–$C_{30}$ cycloalkyl, unsubstituted aryl, unsubstituted aryl-($C_1$–$C_{30}$)-alkyl, unsubstituted $C_2$–$C_{30}$ alkenyl or unsubstituted $C_2$–$C_{30}$ alkynyl, unsubstituted $C_1$–$C_{30}$ trihalogenoalkyl, m is 0 to 4, and wherein $R^{11}$ may be $CH_3$ when $R^9$ and $R^{10}$ are as stated above and Z represents S or NH and $R^9$, $R^{10}$ and $R^{11}$ may simultaneously be H when Z represents S or NH and, $R^1$ is H, OH, OMe, unsubstituted O-($C_1$–$C_{30}$)-alkyl, unsubstituted O-aryl-($C_1$–$C_{30}$)-alkyl, unsubstituted O-($C_2$–$C_{30}$)-alkenyl, unsubstituted O-($C_3$–$C_{30}$)-cycloalkyl or null, $R^2$ is H or OH, or $R^1$ and $R^2$ form together —O—, $R^3$=$R^4$=OMe or $R^3$ and $R^4$ form together —$OCH_2O$—, R is H, unsubstituted $C_1$–$C_{30}$alkyl or O-protecting group, $R^6$=—(C—Y)$Me_2$, —CH=$CMe_2$, or an unsubstituted aryl group or R and $R^6$ form together —$CMe_2$—, Y=H, OH or halogen, n is 0 to 8, $R^5$ is H, OH, OMe, unsubstituted O-($C_1$–$C_{30}$)-alkyl, unsubstituted O-aryl-($C_1$–$C_{30}$)-alkyl, unsubstituted O-($C_2$–$C_{30}$)-alkenyl, unsubstituted O-($C_3$–$C_{30}$)-cycloalkyl or unsubstituted O-aryl, the dotted line is null or forms a double bond depending on the meaning of $R^1$, and a compound according to the following formulae:

1
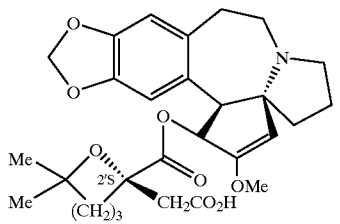

2
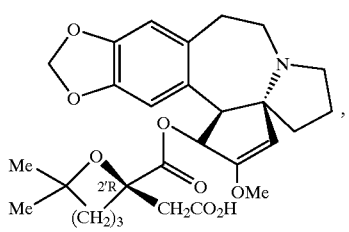

3
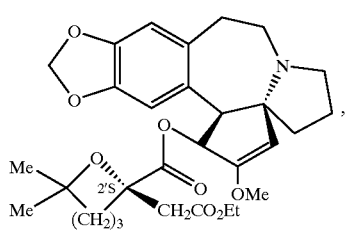

4
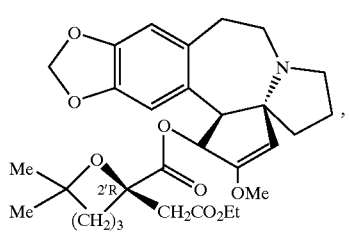

5
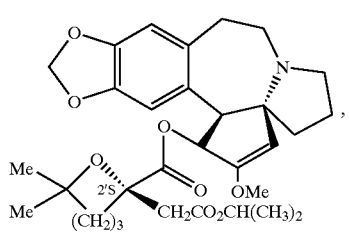

6
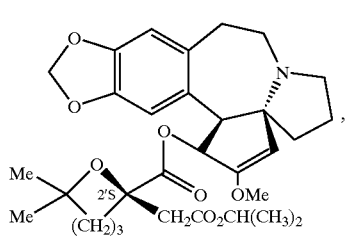

26
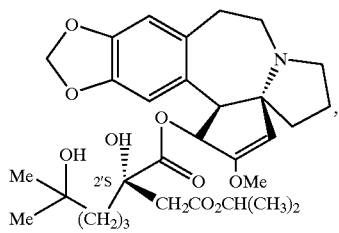

27
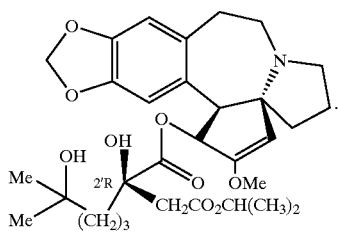

2. A compound of formula (I) according to claim 1 wherein the dotted line forms a double bond, $R^1$ is null, $R^2$ is H, $R^3$ and $R^4$ represent —O—CH$_2$—O—, and $R^5$ is OMe.

3. A compound of formula (I) according to claim 1 wherein the dotted line is null, $R^1$ and $R^2$ represent —O—, $R^3$ and $R^4$ represent —O—CH$_2$—O—, and $R^5$ is OMe.

4. A compound of formula (I) according to claim 2 wherein n=1 to 3.

5. A compound of formula (I) according to claim 1 wherein W represents O.

6. A compound selected from the group consisting of the following compounds 1–21, 26–57 and 62–65:

1
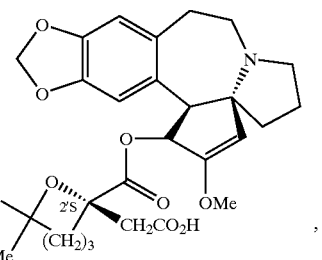

2
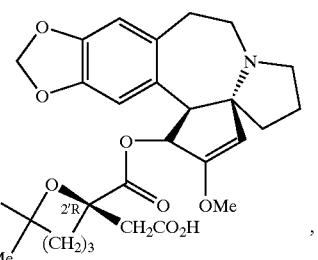

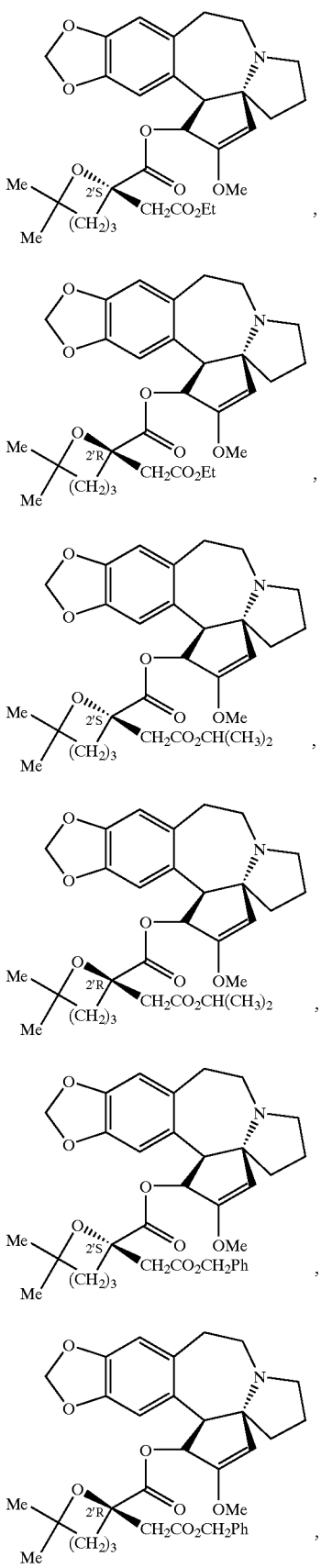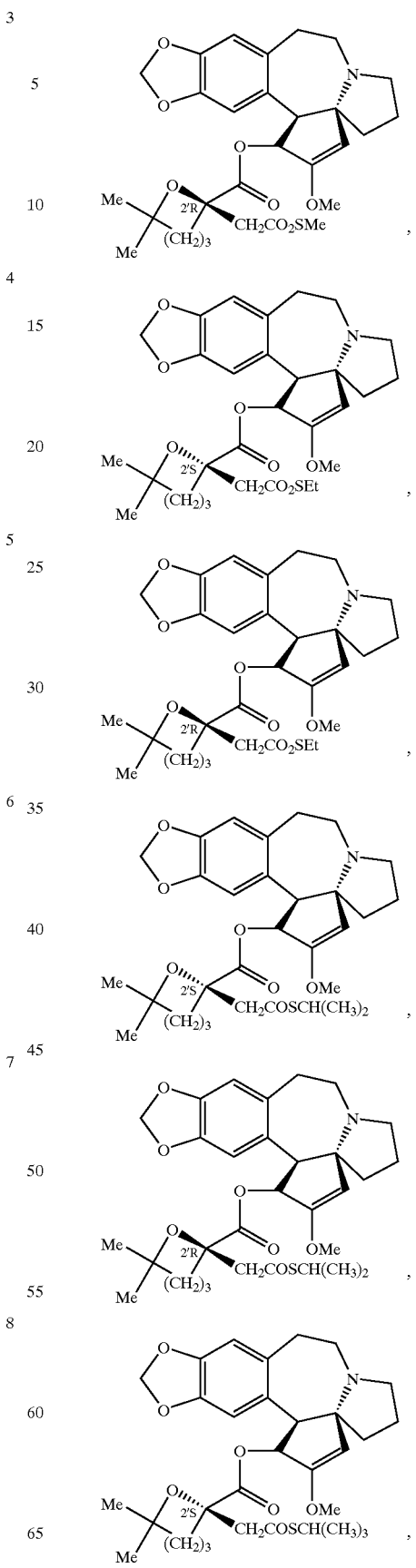

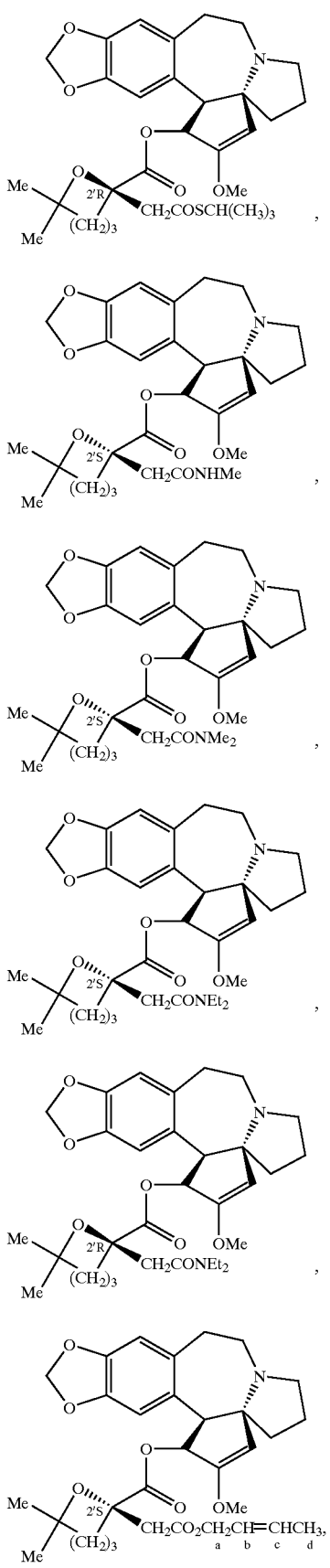
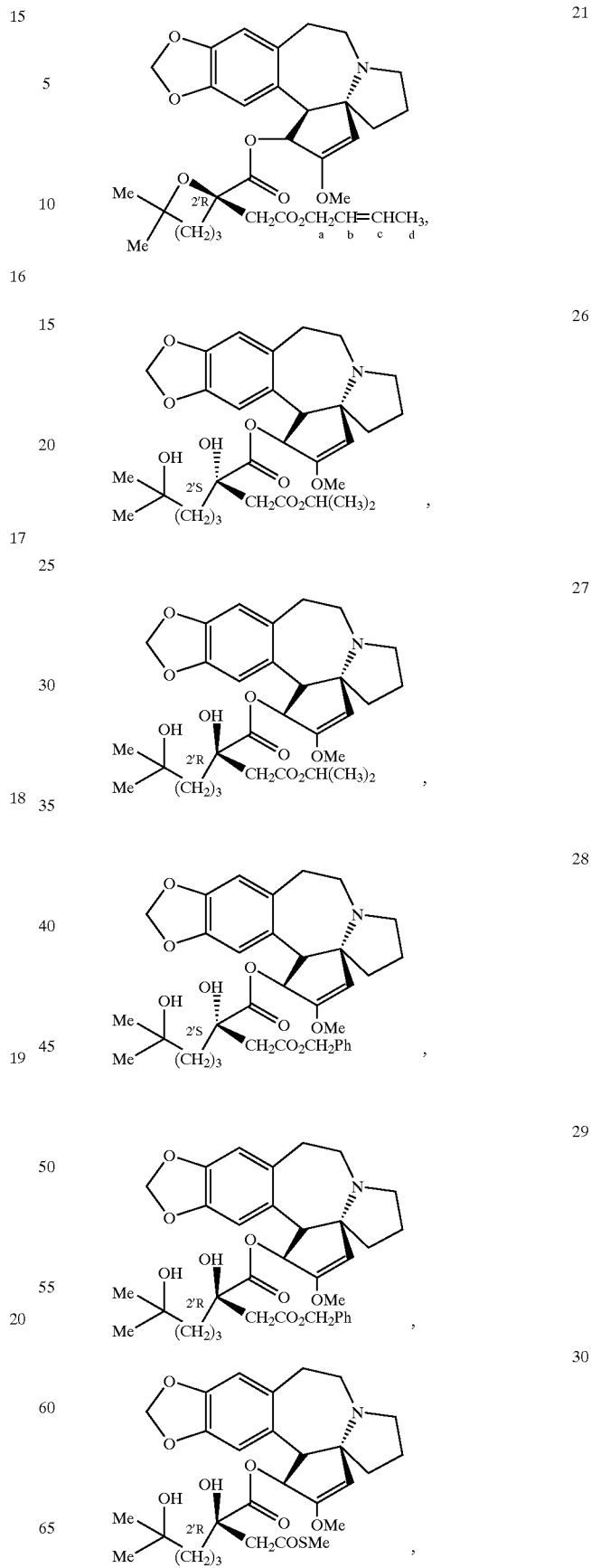

-continued

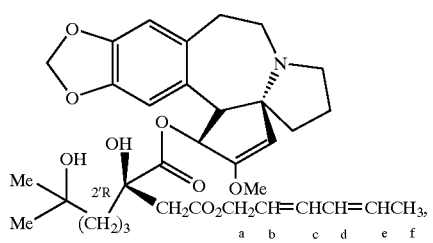
43
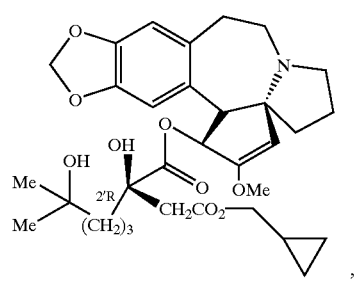
49
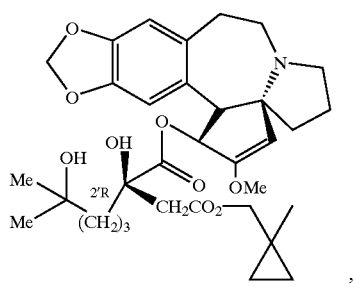
44
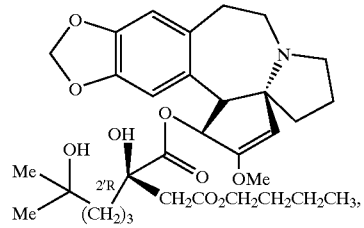
50
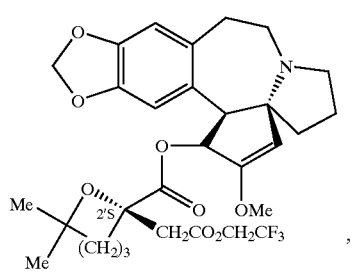
45
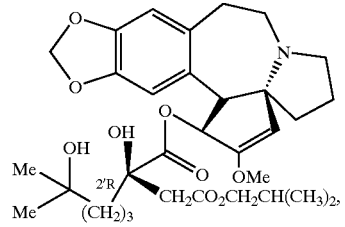
51
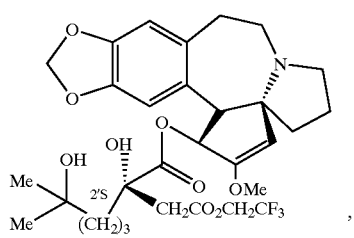
46
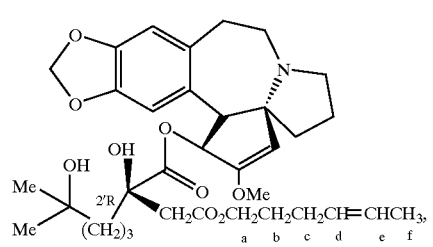
52
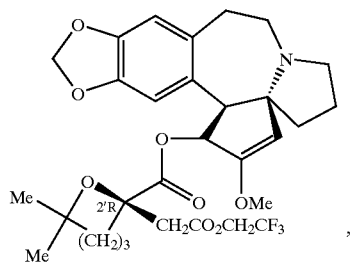
47
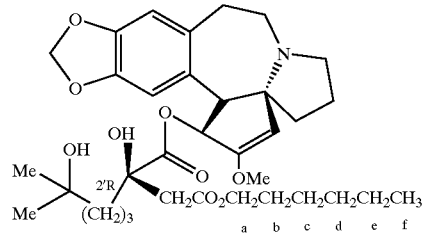
53
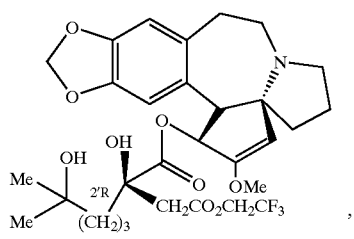
48
54

81
-continued

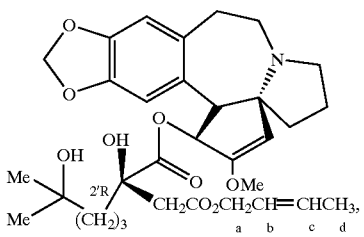

56

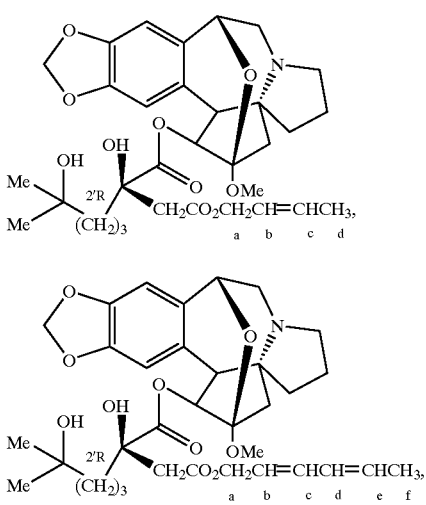

57

62

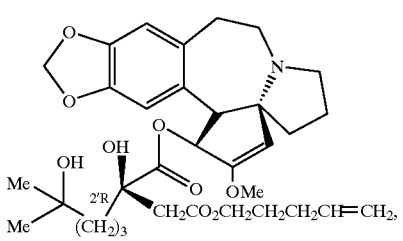

63

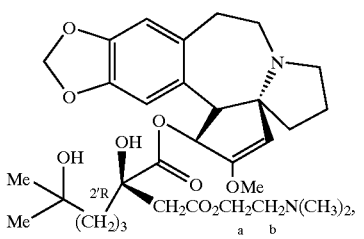

64

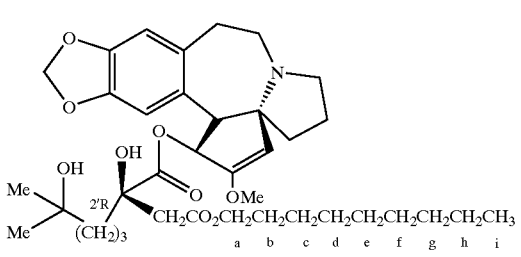

and

82
-continued

65

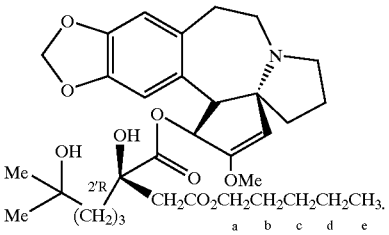

7. A process for preparing a compound of formula (I) according to claim 1 where W represents O, comprising the following steps i) then ii), i) hydrolyzing selectively the compound of formula (II)

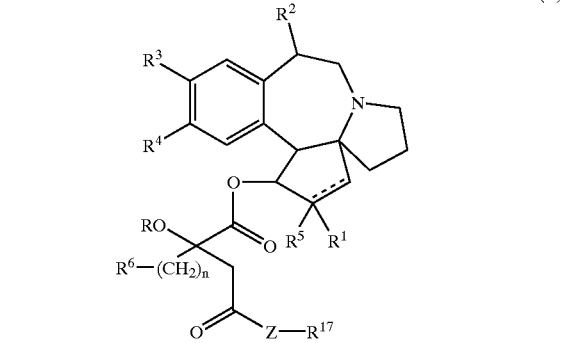

(II)

wherein, $R^1$ is H, OH, OMe, unsubstituted O-($C_1$–$C_{30}$)-alkyl, unsubstituted O-aryl-($C_1$–$C_{30}$)-alkyl, unsubstituted O-($C_2$–$C_{30}$)-alkenyl, unsubstituted O-($C_3$–$C_{30}$)-cycloalkyl or null, $R^2$ is H or OH, or $R^1$ and $R^2$ form together —O—, $R^3$=$R^4$=OMe or $R^3$ and $R^4$ form together —OCH$_2$O—, R is H, unsubstituted $C_1$–$C_{30}$alkyl or O-protecting group;

$R^6$=—(C—Y)Me$_2$, —CH=CMe$_2$, or an unsubstituted aryl group or R and $R^6$ form together —CMe$_2$—, Y=H, OH or halogen, n is 0 to 8, $R^5$ is H, OH, OMe, unsubstituted O-($C_1$–$C_{30}$)-alkyl, unsubstituted O-aryl-($C_1$–$C_{30}$)-alkyl, unsubstituted O-($C_2$–$C_{30}$)-alkenyl, unsubstituted O-($C_3$–$C_{30}$)-cycloalkyl or unsubstituted O-aryl, the dotted line is null or forms a double bond depending on the meaning of $R^1$, Z=O or S, and $R^{17}$ is unsubstituted $C_1$–$C_{30}$ alkyl, unsubstituted $C_2$–$C_{30}$ alkenyl, unsubstituted $C_3$–$C_{30}$ cycloalkyl, unsubstituted $C_2$–$C_{30}$ alkynyl, unsubstituted aryl-($C_1$–$C_{30}$)-alkyl or unsubstituted aryl, with an agent comprising mineral hydroxide, lithium, potassium or sodium hydroxide, in hydro-organic solvent mixture to give as reaction product, ampho-teric acid of formula (III)

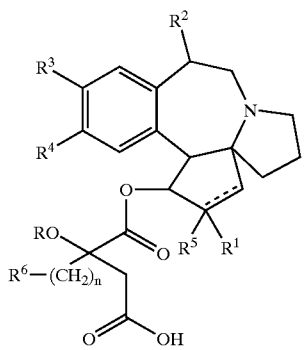

(III)

wherein R¹ to R⁵, R and R⁶ are defined as above, ii) performing the esterification of the above obtained amphoteric acid of formula (III) with an esterification agent and a compound of formula R⁸—ZH, and wherein the steps i) and ii) are carried out successively or simultaneously.

8. The process as described in claim 7 wherein the esterification agent is a lewis acid or a protonic acid.

9. The process as described in claim 8 wherein the amphoteric acid of formula (III) is activated with an imide or by formation of a mixed anhydride or an acid chloride.

10. The process as described in claim 9 wherein the imide is dicyclohexylcarbodi-imide or diisopropylcarbodiimide.

11. The process as described in claim 9 wherein the mixed anhydride is formed with 2,4,6-trichlorobenzoic acid by contact with 2,4,6-trichlorobenzoyl chloride in the presence of a base.

12. The process as described in claim 7 wherein the steps i) and ii) are carried out simultaneously, without isolation of the amphoteric acid of formula (III), via a reaction of transesterification performed in presence of an acidic or basic catalyst.

13. The process as described in claim 12 wherein the catalyst is a base.

14. The process as described in claim 12 wherein the catalyst is a lewis acid or a protonic acid.

15. The process as described in claim 7 wherein Z is O and $R^{17}$ is methyl.

16. A pharmaceutical composition which comprises a therapeutically effective amount of at least one compound of claim 1 associated with one or more pharmaceutically acceptable carriers.

17. A method for inhibiting mammalian parasites, for treating leukemia or leukemic cell lines exhibiting resistance to other agents which comprises administering to a mammal in need of such treatment a therapeutically effective amount of at least one compound of claim 1.

* * * * *

UNITED STATES PATENT AND TRADEMARK OFFICE
CERTIFICATE OF CORRECTION

PATENT NO. : 6,579,869 B1 Page 1 of 1
DATED : June 17, 2003
INVENTOR(S) : Jean-Pierre Robin et al.

It is certified that error appears in the above-identified patent and that said Letters Patent is hereby corrected as shown below:

<u>Column 69,</u>
Lines 45 and 50, change the formula from

to:

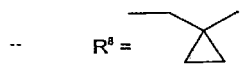

Signed and Sealed this

Eleventh Day of November, 2003

JAMES E. ROGAN
*Director of the United States Patent and Trademark Office*